(12) United States Patent
Rogers et al.

(10) Patent No.: US 10,143,086 B2
(45) Date of Patent: *Nov. 27, 2018

(54) TRANSIENT ELECTRONIC DEVICES COMPRISING INORGANIC OR HYBRID INORGANIC AND ORGANIC SUBSTRATES AND ENCAPSULATES

(71) Applicant: The Board of Trustees of the University of Illinois, Urbana, IL (US)

(72) Inventors: John A. Rogers, Champaign, IL (US); Seung-Kyun Kang, Urbana, IL (US); SukWon Hwang, Urbana, IL (US); Jianjun Cheng, Champaign, IL (US); Yanfeng Zhang, Urbana, IL (US); Hanze Ying, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/351,234

(22) Filed: Nov. 14, 2016

(65) Prior Publication Data

US 2017/0164482 A1    Jun. 8, 2017

Related U.S. Application Data

(63) Continuation of application No. 14/250,671, filed on Apr. 11, 2014, now Pat. No. 9,496,229.
(Continued)

(51) Int. Cl.
*H01L 21/70* (2006.01)
*H01L 21/56* (2006.01)
(Continued)

(52) U.S. Cl.
CPC ............ *H05K 1/185* (2013.01); *A61B 5/686* (2013.01); *A61M 5/44* (2013.01);
(Continued)

(58) Field of Classification Search
CPC .............. H01L 21/56; H01L 21/02274; H01L 23/49894; H01L 23/3192; H01L 23/3121;
(Continued)

(56) References Cited

U.S. PATENT DOCUMENTS 7,192,997 B2    3/2007    Papathomas
7,195,733 B2    3/2007    Rogers et al.
(Continued)

FOREIGN PATENT DOCUMENTS

EP    2422821    2/2012
JP    S53-133575 U    10/1978
(Continued)

OTHER PUBLICATIONS

U.S. Appl. No. 11/001,689, filed Dec. 1, 2004, 2006/0286488, Dec. 21, 2006, U.S. Pat. No. 7,704,684, Apr. 27, 2010.
(Continued)

*Primary Examiner* — Victor A Mandala
(74) *Attorney, Agent, or Firm* — Leydig, Voit & Mayer, Ltd.

(57) ABSTRACT

The invention provides transient devices, including active and passive devices that physically, chemically and/or electrically transform upon application of at least one internal and/or external stimulus. Incorporation of degradable device components, degradable substrates and/or degradable encapsulating materials each having a programmable, controllable and/or selectable degradation rate provides a means of transforming the device. In some embodiments, for example, transient devices of the invention combine degradable high performance single crystalline inorganic materials with selectively removable substrates and/or encapsulants.

30 Claims, 43 Drawing Sheets

Related U.S. Application Data

(60) Provisional application No. 61/811,603, filed on Apr. 12, 2013, provisional application No. 61/828,935, filed on May 30, 2013, provisional application No. 61/829,028, filed on May 30, 2013.

(51) Int. Cl.

| | | |
|---|---|---|
| *H01L 23/29* | (2006.01) | |
| *H01L 23/32* | (2006.01) | |
| *A61B 5/00* | (2006.01) | |
| *H05K 1/02* | (2006.01) | |
| *H05K 5/06* | (2006.01) | |
| *H05K 1/18* | (2006.01) | |
| *H05K 13/00* | (2006.01) | |
| *A61M 5/44* | (2006.01) | |
| *G06K 19/077* | (2006.01) | |
| *H05K 1/03* | (2006.01) | |
| *H05K 3/22* | (2006.01) | |
| *H05K 3/28* | (2006.01) | |
| *H01L 21/02* | (2006.01) | |
| *H01L 21/311* | (2006.01) | |
| *H01L 23/31* | (2006.01) | |
| *H01L 23/498* | (2006.01) | |
| *H01L 25/065* | (2006.01) | |

(52) U.S. Cl.
CPC ...... *G06K 19/0775* (2013.01); *H01L 21/0217* (2013.01); *H01L 21/0228* (2013.01); *H01L 21/02164* (2013.01); *H01L 21/02274* (2013.01); *H01L 21/31111* (2013.01); *H01L 21/31133* (2013.01); *H01L 21/56* (2013.01); *H01L 23/291* (2013.01); *H01L 23/3121* (2013.01); *H01L 23/3192* (2013.01); *H01L 23/49894* (2013.01); *H01L 25/0655* (2013.01); *H05K 1/0275* (2013.01); *H05K 1/0286* (2013.01); *H05K 1/0306* (2013.01); *H05K 3/22* (2013.01); *H05K 3/285* (2013.01); *H05K 3/288* (2013.01); *H05K 5/069* (2013.01); *H05K 13/0023* (2013.01); *A61B 2562/125* (2013.01); *H01L 2924/0002* (2013.01); *H05K 3/287* (2013.01); *H05K 2201/10151* (2013.01); *H05K 2201/10196* (2013.01); *H05K 2201/10212* (2013.01); *H05K 2203/0271* (2013.01); *H05K 2203/0292* (2013.01); *H05K 2203/0769* (2013.01); *H05K 2203/0776* (2013.01); *H05K 2203/0786* (2013.01); *H05K 2203/17* (2013.01); *H05K 2203/175* (2013.01); *H05K 2203/178* (2013.01); *Y10T 29/49124* (2015.01); *Y10T 137/0318* (2015.04); *Y10T 428/239* (2015.01)

(58) Field of Classification Search
CPC ............ H01L 23/291; H01L 21/31133; H01L 21/31111; H01L 21/0228; H01L 21/0217; H01L 25/0655; H01L 21/02164; H05K 1/0286; Y10T 137/0318; Y10T 29/49124; Y10T 428/239; A61B 2562/125; A61B 5/686; G06K 19/0775; A61M 5/44
See application file for complete search history.

(56) References Cited

U.S. PATENT DOCUMENTS

| | | | |
|---|---|---|---|
| 7,521,292 B2 | 4/2009 | Rogers et al. | |
| 7,557,367 B2 | 7/2009 | Rogers et al. | |
| 7,604,663 B1 * | 10/2009 | Reimink | A61L 27/40 623/1.1 |
| 7,605,062 B2 | 10/2009 | Kahen | |
| 7,622,367 B1 | 11/2009 | Nuzzo et al. | |
| 7,704,684 B2 | 4/2010 | Rogers et al. | |
| 7,705,280 B2 | 4/2010 | Nuzzo et al. | |
| 7,799,699 B2 | 9/2010 | Nuzzo et al. | |
| 7,932,123 B2 | 4/2011 | Rogers et al. | |
| 7,943,491 B2 | 5/2011 | Nuzzo et al. | |
| 7,972,875 B2 | 7/2011 | Rogers et al. | |
| 7,982,296 B2 | 7/2011 | Nuzzo et al. | |
| 8,039,847 B2 | 10/2011 | Nuzzo et al. | |
| 8,198,621 B2 | 6/2012 | Rogers et al. | |
| 8,217,381 B2 | 7/2012 | Rogers et al. | |
| 8,367,035 B2 | 2/2013 | Rogers et al. | |
| 8,394,706 B2 | 3/2013 | Nuzzo et al. | |
| 8,440,546 B2 | 5/2013 | Nuzzo et al. | |
| 8,470,701 B2 | 6/2013 | Rogers et al. | |
| 8,552,299 B2 | 10/2013 | Rogers et al. | |
| 8,562,095 B2 | 10/2013 | Alleyne et al. | |
| 8,664,699 B2 | 3/2014 | Nuzzo et al. | |
| 8,666,471 B2 | 3/2014 | Rogers et al. | |
| 8,679,888 B2 | 3/2014 | Rogers et al. | |
| 8,722,458 B2 | 5/2014 | Rogers et al. | |
| 8,729,524 B2 | 5/2014 | Rogers et al. | |
| 8,754,396 B2 | 6/2014 | Rogers et al. | |
| 8,865,489 B2 | 10/2014 | Rogers et al. | |
| 8,946,683 B2 | 2/2015 | Rogers et al. | |
| 9,061,494 B2 | 6/2015 | Rogers et al. | |
| 2003/0010808 A1 | 1/2003 | Uhland et al. | |
| 2006/0038182 A1 | 2/2006 | Rogers et al. | |
| 2006/0286785 A1 | 12/2006 | Rogers et al. | |
| 2007/0032089 A1 | 2/2007 | Nuzzo et al. | |
| 2008/0055581 A1 | 3/2008 | Rogers et al. | |
| 2008/0090097 A1 * | 4/2008 | Shaw | A61L 27/04 428/686 |
| 2008/0108171 A1 | 5/2008 | Rogers et al. | |
| 2008/0157235 A1 | 7/2008 | Rogers et al. | |
| 2008/0212102 A1 | 9/2008 | Nuzzo et al. | |
| 2008/0306359 A1 | 12/2008 | Zdeblick et al. | |
| 2009/0199960 A1 | 8/2009 | Nuzzo et al. | |
| 2009/0294803 A1 | 12/2009 | Nuzzo et al. | |
| 2010/0002402 A1 | 1/2010 | Rogers et al. | |
| 2010/0049165 A1 | 2/2010 | Sutherland et al. | |
| 2010/0059863 A1 | 3/2010 | Rogers et al. | |
| 2010/0072577 A1 | 3/2010 | Nuzzo et al. | |
| 2010/0283069 A1 | 11/2010 | Rogers et al. | |
| 2010/0289124 A1 | 11/2010 | Nuzzo et al. | |
| 2010/0317132 A1 | 12/2010 | Rogers et al. | |
| 2011/0147715 A1 | 6/2011 | Rogers et al. | |
| 2011/0170225 A1 | 7/2011 | Rogers et al. | |
| 2011/0171813 A1 | 7/2011 | Rogers et al. | |
| 2011/0187798 A1 | 8/2011 | Rogers et al. | |
| 2011/0220890 A1 | 9/2011 | Nuzzo et al. | |
| 2011/0230747 A1 * | 9/2011 | Rogers | A61B 5/05 600/377 |
| 2011/0266561 A1 | 11/2011 | Rogers et al. | |
| 2011/0277813 A1 | 11/2011 | Rogers et al. | |
| 2011/0316120 A1 | 12/2011 | Rogers et al. | |
| 2012/0083099 A1 | 4/2012 | Nuzzo et al. | |
| 2012/0105528 A1 | 5/2012 | Alleyne et al. | |
| 2012/0157804 A1 | 6/2012 | Rogers et al. | |
| 2012/0165759 A1 | 6/2012 | Rogers et al. | |
| 2012/0223293 A1 * | 9/2012 | Borenstein | B82Y 10/00 257/40 |
| 2012/0261551 A1 | 10/2012 | Rogers | |
| 2012/0320581 A1 | 12/2012 | Rogers et al. | |
| 2012/0321785 A1 | 12/2012 | Rogers et al. | |
| 2012/0327608 A1 | 12/2012 | Rogers et al. | |
| 2013/0036928 A1 | 2/2013 | Rogers et al. | |
| 2013/0041235 A1 | 2/2013 | Rogers et al. | |
| 2013/0072775 A1 | 3/2013 | Rogers et al. | |
| 2013/0100618 A1 | 4/2013 | Rogers et al. | |
| 2013/0140649 A1 * | 6/2013 | Rogers | H01L 29/66 257/414 |
| 2013/0320503 A1 | 12/2013 | Nuzzo et al. | |
| 2013/0333094 A1 | 12/2013 | Rogers et al. | |
| 2014/0092158 A1 | 4/2014 | Alleyne et al. | |
| 2014/0140020 A1 | 5/2014 | Rogers et al. | |
| 2014/0163390 A1 * | 6/2014 | Rogers | A61B 5/05 600/476 |

(56) References Cited

U.S. PATENT DOCUMENTS

| | | |
|---|---|---|
| 2014/0191236 A1 | 7/2014 | Nuzzo et al. |
| 2014/0216524 A1 | 8/2014 | Rogers et al. |
| 2014/0220422 A1 | 8/2014 | Rogers et al. |
| 2014/0305900 A1 | 10/2014 | Rogers et al. |
| 2014/0323968 A1 | 10/2014 | Rogers et al. |
| 2014/0361409 A1 | 12/2014 | Rogers et al. |
| 2014/0373898 A1 | 12/2014 | Rogers et al. |
| 2014/0374872 A1 | 12/2014 | Rogers et al. |
| 2015/0001462 A1 | 1/2015 | Rogers et al. |
| 2015/0080695 A1 | 3/2015 | Rogers et al. |
| 2015/0132873 A1 | 5/2015 | Rogers et al. |
| 2015/0141767 A1 | 5/2015 | Rogers et al. |
| 2015/0181700 A1 | 6/2015 | Rogers et al. |
| 2015/0207012 A1 | 7/2015 | Rogers et al. |
| 2015/0237711 A1 | 8/2015 | Rogers et al. |
| 2015/0290938 A1 | 10/2015 | Rogers et al. |
| 2015/0373831 A1 | 12/2015 | Rogers et al. |
| 2015/0380355 A1 | 12/2015 | Rogers et al. |
| 2016/0005700 A1 | 1/2016 | Rogers et al. |
| 2016/0027737 A1 | 1/2016 | Rogers et al. |
| 2016/0050750 A1 | 2/2016 | Rogers et al. |
| 2016/0066789 A1 | 3/2016 | Rogers et al. |
| 2016/0072027 A1 | 3/2016 | Rogers et al. |
| 2016/0133843 A1 | 5/2016 | Rogers et al. |
| 2016/0136877 A1 | 5/2016 | Rogers et al. |
| 2016/0284544 A1 | 9/2016 | Nuzzo et al. |
| 2016/0293794 A1 | 10/2016 | Nuzzo et al. |
| 2016/0381789 A1 | 12/2016 | Rogers et al. |
| 2017/0020402 A1 | 1/2017 | Rogers et al. |

FOREIGN PATENT DOCUMENTS

| | | |
|---|---|---|
| JP | S59-155151 A | 9/1984 |
| JP | 2010-086994 | 4/2010 |
| JP | 2010-205771 A | 9/2010 |
| WO | WO1998000107 | 1/1998 |
| WO | WO2004000915 | 12/2003 |
| WO | WO2004062697 | 7/2004 |
| WO | WO2005012606 | 2/2005 |
| WO | WO2005122285 | 12/2005 |
| WO | WO2005123114 | 12/2005 |
| WO | WO2007016524 | 2/2007 |
| WO | WO2008030960 | 3/2008 |
| WO | WO2008085904 | 7/2008 |
| WO | WO2008108838 | 9/2008 |
| WO | WO2013089867 | 6/2013 |
| WO | WO2014124044 | 8/2014 |
| WO | WO2014124049 | 8/2014 |
| WO | WO2014126927 | 8/2014 |
| WO | WO2014138465 | 9/2014 |
| WO | WO2014165686 | 10/2014 |

OTHER PUBLICATIONS

U.S. Appl. No. 11/115,954, filed Apr. 27, 2005, 2005/0238967, Oct. 27, 2005, U.S. Pat. No. 7,195,733 Mar. 27, 2007.
U.S. Appl. No. 11/145,542, filed Jun. 2, 2005, 2006/0038182, Feb. 23, 2006, U.S. Pat. No. 7,557,367, Jul. 7, 2009.
U.S. Appl. No. 11/145,574, filed Jun. 2, 2005, 2009/0294803, Dec. 3, 2009, U.S. Pat. No. 7,622,367, Nov. 24, 2009.
U.S. Appl. No. 11/421,654, filed Jun. 1, 2006, 2007/0032089, Feb. 8, 2007, U.S. Pat. No. 7,799,699, Sep. 21, 2010.
U.S. Appl. No. 11/423,192, filed Jun. 9, 2006, 2009/0199960, Aug. 13, 2009, U.S. Pat. No. 7,943,491, May 17, 2011.
U.S. Appl. No. 11/423,287, filed Jun. 9, 2006, 2006/0286785, Dec. 21, 2006, U.S. Pat. No. 7,521,292, Apr. 21, 2009.
U.S. Appl. No. 11/465,317, filed Aug. 17, 2006.
U.S. Appl. No. 11/675,659, filed Feb. 16, 2007, 2008/0055581.
U.S. Appl. No. 11/782,799, filed Jul. 25, 2007, 2008/0212102, Sep. 4, 2008, U.S. Pat. No. 7,705,280, Apr. 27, 2010.
U.S. Appl. No. 12/669,287, filed Aug. 30, 2007, 2011/0187798, Aug. 4, 2011, U.S. Pat. No. 9,061,494, Jun. 23, 2015.
U.S. Appl. No. 11/851,182, filed Sep. 6, 2007, 2008/0157235, Jul. 3, 2008, U.S. Pat. No. 8,217,381, Jul. 10, 2012.
U.S. Appl. No. 11/858,788, filed Sep. 20, 2007, 2008/0108171, May 8, 2008, U.S. Pat. No. 7,932,123, Apr. 26, 2011.
U.S. Appl. No. 11/981,380, filed Oct. 31, 2007, 2010/0283069, Nov. 11, 2010, U.S. Pat. No. 7,972,875, Jul. 5, 2011.
U.S. Appl. No. 12/372,605, filed Feb. 17, 2009.
U.S. Appl. No. 12/398,811, filed Mar. 5, 2009, 2010/0002402, Jan. 7, 2010, U.S. Pat. No. 8,552,299, Oct. 8, 2013.
U.S. Appl. No. 12/405,475, filed Mar. 17, 2009, 2010/0059863, Mar. 11, 2010, U.S. Pat. No. 8,198,621, Jun. 12, 2012.
U.S. Appl. No. 12/996,924, filed Jun. 16, 2009, 2011/0147715, Jun. 23, 2011, U.S. Pat. No. 8,946,683, Feb. 3, 2015.
U.S. Appl. No. 12/522,582, filed Jul. 9, 2009.
U.S. Appl. No. 12/564,566, filed Sep. 22, 2009, 2010/0072577, Mar. 25, 2010, U.S. Pat. No. 7,982,296, Jul. 19, 2011.
U.S. Appl. No. 13/120,486, filed Sep. 24, 2009, 2011/0277813, Nov. 17, 2011, U.S. Pat. No. 8,679,888, Mar. 25, 2014.
U.S. Appl. No. 12/778,588, filed May 12, 2010, 2010/0317132, Dec. 16, 2010, U.S. Pat. No. 8,865,489, Oct. 21, 2014.
U.S. Appl. No. 12/844,492, filed Jul. 27, 2010, 2010/0289124, Nov. 18, 2010, U.S. Pat. No. 8,039,847, Oct. 18, 2011.
U.S. Appl. No. 12/892,001, filed Sep. 28, 2010, 2011/0230747, Sep. 22, 2011, U.S. Pat. No. 8,666,471, Mar. 4, 2014.
U.S. Appl. No. 12/916,934, filed Nov. 1, 2010, 2012/0105528, May 3, 2012, U.S. Pat. No. 8,562,095, Oct. 22, 2013.
U.S. Appl. No. 12/947,120, filed Nov. 16, 2010, 2011/0170225, Jul. 14, 2011, U.S. Pat. No. 9,057,994, Jun. 16, 2015.
U.S. Appl. No. 12/968,637, filed Dec. 15, 2010, 2012/0157804, Jun. 21, 2012.
U.S. Appl. No. 13/046,191, filed Mar. 11, 2011, 2012/0165759, Jun. 28, 2012.
U.S. Appl. No. 13/071,027, filed Mar. 24, 2011, 2011/0171813, Jul. 14, 2011, U.S. Pat. No. 8,895,406, Nov. 25, 2014.
U.S. Appl. No. 13/095,502, filed Apr. 27, 2011.
U.S. Appl. No. 13/100,774, filed May 4, 2011, 2011/0266561, Nov. 3, 2011, U.S. Pat. No. 8,722,458, May 13, 2014.
U.S. Appl. No. 13/113,504, filed May 23, 2011, 2011/0220890, Sep. 15, 2011, U.S. Pat. No. 8,440,546, May 14, 2013.
U.S. Appl. No. 13/228,041, filed Sep. 8, 2011, 2011/0316120, Dec. 29, 2011.
U.S. Appl. No. 13/270,954, Oct. 11, 2011, 2012/0083099, Apr. 5, 2012, U.S. Pat. No. 8,394,706, Mar. 12, 2013.
U.S. Appl. No. 13/349,336, filed Jan. 12, 2012, 2012/0261551, Oct. 18, 2012, U.S. Pat. No. 9,442,285, Sep. 13, 2016.
U.S. Appl. No. 13/441,598, filed Apr. 6, 2012, 2012/0327608, Dec. 27, 2012, U.S. Pat. No. 8,729,524, May 20, 2014.
U.S. Appl. No. 13/441,618, filed Apr. 6, 2012, 2013/0100618, Apr. 25, 2013, U.S. Pat. No. 8,754,396, Jun. 17, 2014.
U.S. Appl. No. 13/472,165, filed May 15, 2012, 2012/0320581, Dec. 20, 2012.
U.S. Appl. No. 13/486,726, filed Jun. 1, 2012, 2013/0072775, Mar. 21, 2013, U.S. Pat. No. 8,934,965, Jan. 13, 2015.
U.S. Appl. No. 13/492,636, filed Jun. 8, 2012, 2013/0041235, Feb. 14, 2013.
U.S. Appl. No. 13/549,291, filed Jul. 13, 2012, 2013/0036928, Feb. 14, 2013, 9,555,644, Jan. 31, 2017.
U.S. Appl. No. 13/596,343, filed Aug. 28, 2012, 2012/0321785, Dec. 20, 2012, U.S. Pat. No. 8,367,035, Feb. 5, 2013.
U.S. Appl. No. 13/624,096, filed Sep. 21, 2012, 2013/0140649, Jun. 6, 2013.
U.S. Appl. No. 13/801,868, filed Mar. 13, 2013, 2013/0320503, Dec. 5, 2013, U.S. Pat. No. 8,664,699, Mar. 4, 2014.
U.S. Appl. No. 13/835,284, filed Mar. 15, 2013, 2014/0220422, Aug. 7, 2014.
U.S. Appl. No. 13/853,770, filed Mar. 29, 2013, 2013/0333094, Dec. 19, 2013, U.S. Pat. No. 9,554,484, Jan. 24, 2017.
U.S. Appl. No. 13/974,963, filed Aug. 23, 2013, 2014/0140020, May 22, 2014, U.S. Pat. No. 8,905,772, Dec. 9, 2014.
U.S. Appl. No. 14/033,765, filed Sep. 23, 2013, 2014/0092158, Apr. 3, 2014, U.S. Pat. No. 9,278,522, Mar. 8, 2016.
U.S. Appl. No. 14/140,299, filed Dec. 24, 2013, 2014/0163390, Jun. 12, 2014.

(56) References Cited

OTHER PUBLICATIONS

U.S. Appl. No. 14/155,010, filed Jan. 14, 2014, 2014/0191236, Jul. 10, 2014, U.S. Pat. No. 9,450,043, Sep. 20, 2016.
U.S. Appl. No. 14/173,525, filed Feb. 5, 2014, 2014/0216524, Aug. 7, 2014, U.S. Pat. No. 9,105,782, Aug. 11, 2015.
U.S. Appl. No. 14/766,301, filed Feb. 5, 2014, 2015/0373831, Dec. 24, 2015.
U.S. Appl. No. 14/766,333, filed Feb. 5, 2014, 2015/0380355, Dec. 31, 2015.
U.S. Appl. No. 14/766,926, filed Feb. 11, 2014, 2016/0066789, Mar. 10, 2016.
U.S. Appl. No. 14/772,354, filed Mar. 6, 2014, 2016/0005700, Jan. 7, 2016.
U.S. Appl. No. 14/209,481, filed Mar. 13, 2014, 2014/0373898, Dec. 25, 2014, U.S. Pat. No. 9,117,940, Aug. 25, 2015.
U.S. Appl. No. 14/220,910, filed Mar. 20, 2014, 2014/0374872, Dec. 25, 2014, U.S. Pat. No. 9,324,733, Apr. 26, 2016.
U.S. Appl. No. 14/220,923, filed Mar. 20, 2014, 2015/0001462, Jan. 1, 2015, U.S. Pat. No. 9,105,555, Aug. 11, 2015.
U.S. Appl. No. 14/772,312, filed Apr. 3, 2014, 2016/0133843, May 12, 2016.
U.S. Appl. No. 14/246,962, filed Apr. 7, 2014, 2014/0361409, Dec. 11, 2014, U.S. Pat. No. 9,349,900, May 24, 2016.
U.S. Appl. No. 14/250,671, filed Apr. 11, 2014, 2014/0305900, Oct. 16, 2014, U.S. Pat. No. 9,496,229, Nov. 15, 2016.
U.S. Appl. No. 14/251,259, filed Apr. 11, 2014, 2014/0323968, Oct. 30, 2014.
U.S. Appl. No. 14/479,100, filed Sep. 5, 2014, 2015/0132873, May 14, 2015.
U.S. Appl. No. 14/504,736, filed Oct. 2, 2014, 2015/0141767, May 21, 2015.
U.S. Appl. No. 14/521,319, filed Oct. 22, 2014, 2015/0181700, Jun. 25, 2015.
U.S. Appl. No. 14/532,687, filed Nov. 4, 2014, 2015/0080695, Mar. 19, 2015.
U.S. Appl. No. 14/599,290, filed Jan. 16, 2015, 2015/0207012, Jul. 23, 2015.
U.S. Appl. No. 14/686,304, filed Apr. 14, 2015, 2015/0290938, Oct. 15, 2015, U.S. Pat. No. 9,487,002, Nov. 8, 2016.
U.S. Appl. No. 14/706,733, filed May 7, 2015, 2015/0237711, Aug. 20, 2015.
U.S. Appl. No. 14/789,645, filed Jul. 1, 2015, 2016/0027737, Jan. 28, 2016, U.S. Pat. No. 9,515,025, Dec. 6, 2016.
U.S. Appl. No. 14/800,363, filed Jul. 15, 2015, 2016/0072027, Mar. 10, 2016.
U.S. Appl. No. 14/818,109, filed Aug. 4, 2015, 2016/0050750, Feb. 18, 2016.
U.S. Appl. No. 15/501,364, filed Aug. 11, 2015.
U.S. Appl. No. 15/501,373, filed Aug. 11, 2015.
U.S. Appl. No. 15/501,379, filed Aug. 11, 2015.
U.S. Appl. No. 14/944,039, filed Nov. 17, 2015, 2016/0136877, May 19, 2016.
U.S. Appl. No. 15/084,091, filed Mar. 29, 2016, 2016/0284544, Sep. 29, 2016.
U.S. Appl. No. 15/084,112, filed Mar. 29, 2016, 2016/0381789, Dec. 29, 2016.
U.S. Appl. No. 15/084,211, filed Mar. 29, 2016, 2016/0293794, Oct. 6, 2016.
U.S. Appl. No. 15/146,629, filed May 4, 2016, 2017/0020402, Jan. 26, 2017.
U.S. Appl. No. 15/339,338, filed Oct. 31, 2016.
U.S. Appl. No. 15/349,525, filed Nov. 11, 2016.
U.S. Appl. No. 15/351,234, filed Nov. 14, 2016.
U.S. Appl. No. 15/354,951, filed Nov. 17, 2016.
U.S. Appl. No. 15/374,926, filed Dec. 9, 2016.
U.S. Appl. No. 15/375,514, filed Dec. 12, 2016.
U.S. Appl. No. 15/402,684, filed Jan. 10, 2017.
U.S. Appl. No. 15/402,718, filed Jan. 10, 2017.
U.S. Appl. No. 15/402,723, filed Jan. 10, 2017.
PCT/US16/40717, Jul. 1, 2016, WO 2017/004531, Jan. 5, 2017.
PCT/US16/40814, Jul. 1, 2016, WO 2017/004576, Jan. 5, 2017.
PCT/US16/35336, Jun. 1, 2016, WO 2016/196675, Dec. 8, 2016.
PCT/US16/35331, filed Jun. 1, 2016, WO 2016-196673, filed Dec. 8, 2016.
PCT/US15/53452, Oct. 1, 2015, WO 2016/054348, Apr. 7, 2016.
Allam et al. (Jan. 1968) "The structure of evaporated silicon oxide films and its effect on the electrical and optical properties," Thin Solid Films. 1(4):245-254.
Babcock et al. (May 2001) "Analog characteristics of metal-insulator-metal capacitors using PECVD nitride dielectrics," IEEE Electron Device Lett. 22(5):230-232.
Bergstrom et al. (1990) "Surface chemistry of silicon nitride powders: Electrokinetic behaviour and ESCA studies," Colloid Surf. 49:183-197.
Bettinger et al. (2010) "Biomaterial-based organic electronic devices," Poly. Int. 59(5):563-576.
Bettinger et al. (Nov. 4, 2009) "Organic Thin-Film Transistors Fabricated on Resorbable Biomaterial Substrates," Adv. Mater. 22(5):651-655.
Ceiler et al. (1995) "Plasma-Enhanced Chemical Vapor Deposition of Silicon Dioxide Deposited at Low Temperatures," J. Electrochem. Soc. 142(6):2067-2071.
Dagdeviren et al. (Oct. 25, 2013) "Transient, Biocompatible Electronics and Energy Harvesters Based on ZnO," Small. 9(20):3398-3404.
Dameron et al. (Mar. 5, 2008) "Gas Diffusion Barriers on Polymers Using Multilayers Fabricated by Al2O3 and Rapid SiO2 Atomic Layer Deposition," J. Phys. Chem. C. 112(12):4573-4580.
Dove (Nov. 1999) "The dissolution kinetics of quartz in aqueous mixed cation solutions," Geochim. Cosmochim. Acta. 63(22):3715-3727.
Dove et al. (Aug. 1997) "The influence of the alkaline earth cations, magnesium, calcium, and barium on the dissolution kinetics of quartz," Geochim. Cosmochim. Acta. 61(16):3329-3340.
Hierlemann (Sep. 2005) "Integrated chemical microsensor systems in CMOS technology," LabPlus international. 19(4).
House et al. (1992) "Dissolution kinetics of silica between 5 and 35° C. Application of a titrimetric method," J. Chem. Soc., Faraday Trans. 88(14):2021-2026.
Hwang et al. (Jul. 12, 2013) "Materials for Bioresorbable Radio Frequency Electronics," Adv. Mater. 25(26):3526-3531.
Hwang et al. (Sep. 28, 2012) "A Physically Transient Form of Silicon Electronics," Science. 337(6102)1640-1644.
Hwang et al. (Sep. 6, 2013) "Materials and Fabrication Processes for Transient and Bioresorbable High-Performance Electronics," Adv. Funct. Mater. 23(33):4087-4093.
Icenhower et al. (Dec. 15, 2000) "The dissolution kinetics of amorphous silica into sodium chloride solutions: effects of temperature and ionic strength," Geochim. Cosmochim. Acta. 64(24):4193-4203.
International Search Report with Written Opinion corresponding to International Patent Application No. PCT/US2014/033732, dated Aug. 27, 2014.
Irimia-Vladu (2010) "Environmentally sustainable organic field effect transistors," Organic Electronics. 11:1974-1990.
Irimia-Vladu et al. (Dec. 8, 2010) "Biocompatible and Biodegradable Materials for Organic Field-Effect Transistors," Adv. Funct. Mater. 20(23):4069-4076.
Kim et al. (2009) "Silicon electronics on silk as a path to bioresorbable, implantable devices," Appl. Phys. Lett. 95:133701.
Kim et al. (Apr. 18, 2010) "Dissolvable films of silk fibroin for ultrathin conformal bio-integrated electronics," Nat. Mater. 9:511-517.
Knauss et al. (Jan. 1988) "The dissolution kinetics of quartz as a function of pH and time at 70° C.," Geochimica et Cosmochimica Acta. 52(1):43-53.
Kozicki et al. (2005) "Programmable metallization cell memory based on Ag—Ge—S and Cu—Ge—S solid electrolytes," NonVolatile Memory Technology Symposium. 83-89.
Laarz et al. (Oct. 2000) "Dissolution and Deagglomeration of Silicon Nitride in Aqueous Medium," J. Am. Ceram. Soc. 83(10):2394-2400.

(56) References Cited

OTHER PUBLICATIONS

Legnani et al. (Dec. 1, 2008) "Bacterial cellulose membrane as flexible substrate for organic light emitting devices," Thin Solid Films. 517(3):1016-1020.
Li et al. (Jun. 25, 2013) "An Analytical Model of Reactive Diffusion for Transient Electronics," Adv. Funct. Mater. 23(24):3106-3114.
Lin et al. (Jun. 27, 2012) "Optimizing the Organic/Inorganic Barrier Structure for Flexible Plastic Substrate Encapsulation," International Journal of Engineering and Technology Innovation. 2(3)184-194.
Meyer et al. (May 11, 2009) "Al2O3/ZrO2 Nanolaminates as Ultrahigh Gas-Diffusion Barriers—A Strategy for Reliable Encapsulation of Organic Electronics," Adv. Mater. 21(18):1845-1849.
Notice of Allowance corresponding to U.S. Appl. No. 14/250,671, dated Jul. 13, 2016.
Park et al. (Dec. 2013) "Inorganic/organic multilayer passivation incorporating alternating stacks of organic/inorganic multilayers for long-term air-stable organic light-emitting diodes," Org. Electron. 14(12):3385-3391.
Restriction Requirement corresponding to U.S. Appl. No. 14/250,671, dated Jun. 9, 2015.
Robertson (Dec. 2004) "High dielectric constant oxides," Eur. Phys. J. Appl. Phys. 28:265-291.
Rosink et al. (May 2005) "34.1: Ultra-Thin Encapsulation for Large-Area OLED Displays," SID Digest of Technical Papers. 36(1):1272-1275.
Sang et al. (2011) Int. Cont. Electronic Packaging Technology & High Density Packaging, Shanghai, China.
Seidel et al. (1990) "Anisotropic Etching of Crystalline Silicon in Alkaline Solutions: I. Orientation Dependence and Behavior of Passivation Layers," J. Electrochem. Soc. 137(11):3612-3626.
Supplementary European Search Report corresponding to European Patent Application No. EP14782878.4, dated Dec. 1, 2016.
Toxicological Profile for Ammonia, published by the U.S. Department of Health and Human Services, ATSDR (2004).
University of Illinois (Sep. 27, 2012) "Biocompatible Electronic Devices Dissolve in the Body Environment," Phys.org. http://www.phys.org/news/2012-09-transientelectronics-biocompatible-electronic-devices.html. [Last accessed Jul. 30, 2014].
University of Illinois (Sep. 27, 2012) "Transient Electronics: UI Researcher demonstrates transient electronics," Youtube.com. http://www.youtube.com/watch?=NnmHZXvJhlk. [Last accessed Jul. 30, 2014].
Van Assche et al. (May 2004) "P-111: A Thin Film Encapsulation Stack for PLED and OLED Displays," SID Digest of Technical Papers. 35(1):695-697.
Worley (1994) "Dissolution kinetics and mechanisms in quartz- and granite-water systems," Ph. D. Thesis, Massachusetts Institute of Technology. 231-240.
Yin et al. (Feb. 5, 2014) "Dissolvable Metals for Transient Electronics," Adv. Funct. Mater. 24(5):645-658.
Zhmud et al. (Oct. 15, 1999) "Dissolution Kinetics of Silicon Nitride in Aqueous Suspension," J. Colloid Interface Sci. 218(2):582-584.
Australian Patent Office, Examination Report in Australian Patent Application No. 2014250839 (May 12, 2017).
Japanese Patent Offce, Notice of Reasons for Refusal in Japanese Patent Application No. 2016-507672 (Feb. 22, 2018).

\* cited by examiner

\*\* pH dependency

\*\* Film property dependency

** pH dependency

** Film property dependency

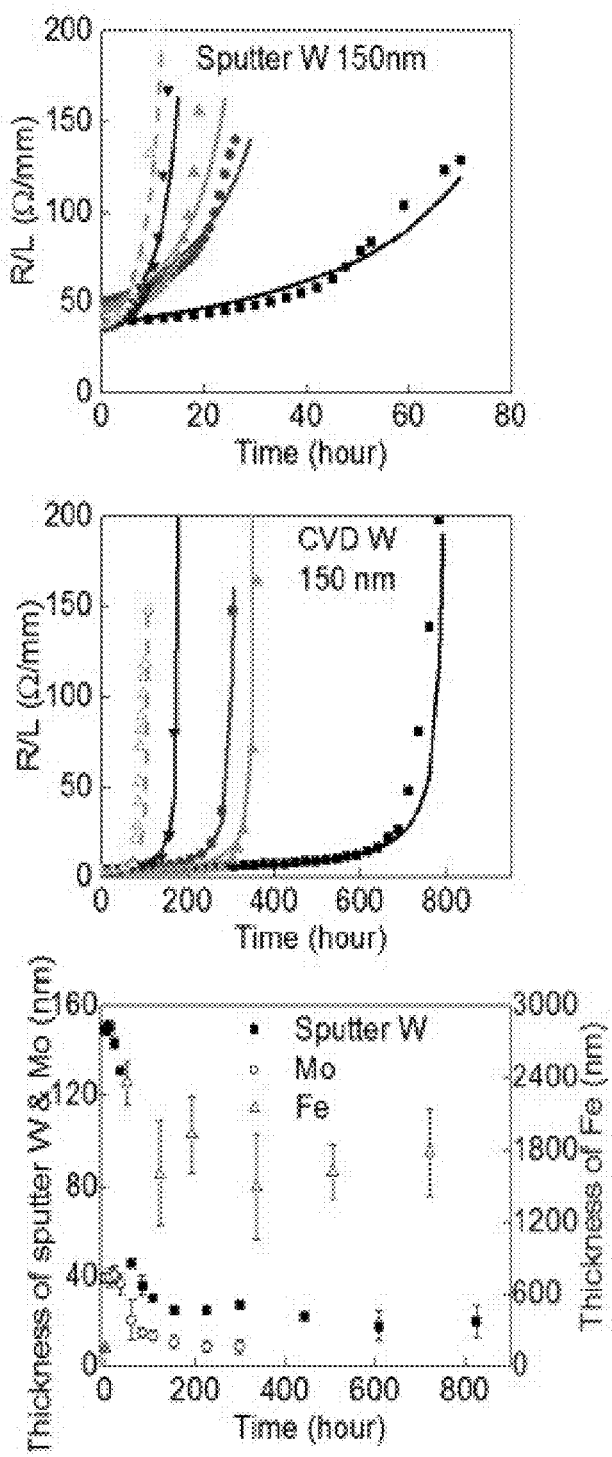
Figure 13 (con't)

4 pentanoic anhydride

Degradable chain

1,3,5 triallyl-1,35 triazene-2,4,6 (1H, 3H, 5H) trione

1,4 butane dithiol

\* Component ratio
| | Anhydride | Trione | Dithiol |
|---|---|---|---|
| A1T1 | 1 | 1 | 2.5 |
| A1T2 | 1 | 2 | 4 |
| A1T4 | 1 | 4 | 7 |
Degradation rate
Hydrophobic
Figure 39B
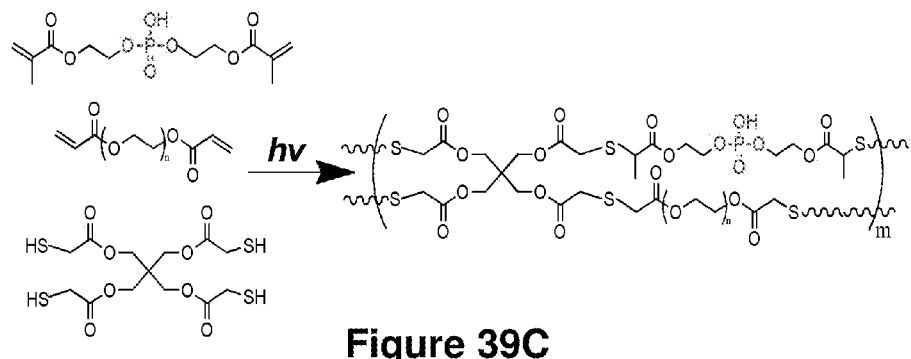
Figure 39C
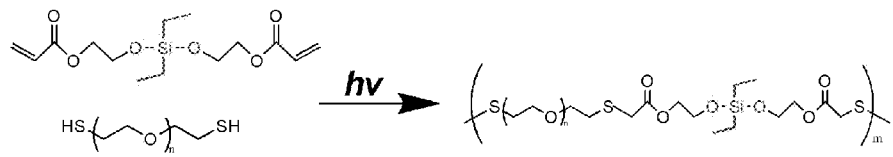
Figure 39D

TRANSIENT ELECTRONIC DEVICES COMPRISING INORGANIC OR HYBRID INORGANIC AND ORGANIC SUBSTRATES AND ENCAPSULATES

CROSS-REFERENCE TO RELATED APPLICATIONS

This application is a continuation of U.S. application Ser. No. 14/250,671, filed Apr. 11, 2014, which is a U.S. application which claims the benefit of priority to U.S. Provisional Patent Application No. 61/811,603, filed Apr. 12, 2013, U.S. Provisional Patent Application No. 61/828,935, filed May 30, 2013, and U.S. Provisional Patent Application No. 61/829,028, filed May 30, 2013, each of which are hereby incorporated by reference in their entireties.

STATEMENT REGARDING FEDERALLY SPONSORED RESEARCH OR DEVELOPMENT

This invention was made, at least in part, with United States governmental support awarded by the National Science Foundation award no. 1242240 and the Defense Advanced Research Projects Agency award no. W911NF-11-1-0254. The United States Government has certain rights in this invention.

BACKGROUND OF INVENTION

This invention is in the field of transient devices, and relates generally to passive and active devices designed to programmably transform.

Transient devices have potential for a range of important applications. For example, eco-degradable environmental sensors avoid the need for device collection and bioresorbable medical devices that degrade and are cleared from the body avoid toxicity and inflammation. Strategically, military devices that degrade after a preselected time or upon application of a triggered stimulus avoid transferring knowledge or materials to enemies. All of these envisioned applications are important, but implementation of transient devices is dependent upon design strategies. Design strategies for transient devices must (i) support device fabrication using degradable device component materials and degradable substrates, (ii) provide for accurate control of the useful lifetime of the device, and (iii) utilize materials that are compatible with and perform adequately for a given application within a target environment.

Recently, a number of patents and publications have disclosed devices with transient properties. For example, Kim et al., "Silicon electronics on silk as a path to bioresorbable implantable devices", Appl. Phys. Lett. 95, 133701 (2009); U.S. Patent Application Publication 2011/0230747; and International Patent Application Publication WO 2008/085904 disclose biodegradable electronic devices that may include a biodegradable semiconducting material and a biodegradable substrate. Bettinger et al., "Organic thin film transistors fabricated on resorbable biomaterial substrates", Adv. Mater., 22(5), 651-655 (2010); Bettinger et al., "Biomaterial-based organic electronic devices", Poly. Int. 59(5), 563-576 (2010); and Irimai-Vladu, "Environmentally sustainable organic field effect transistors", Organic Electronics, 11, 1974-1990 (2010) disclose biodegradable electronic devices that may include a biodegradable organic conducting material and a biodegradable substrate. International Patent Application Publication WO 2008/108838 discloses biodegradable devices for delivering fluids and/or biological material to tissue. U.S. Patent Application Publication 2008/0306359 discloses ingestible devices for diagnostic and therapeutic applications. Kozicki et al., "Programmable metallization cell memory based on Ag—Ge—S and Cu—Ge—S solid electrolytes", NonVolatile Memory Technology Symposium, 83-89 (2005) discloses memory devices where metal ions within an electrolyte may be reduced or oxidized to form or remove solid metal interconnects.

SUMMARY OF THE INVENTION

The invention provides transient devices, including active and passive devices that physically, chemically and/or electrically transform upon application of at least one internal and/or external stimulus. Incorporation of degradable device components, degradable substrates and/or degradable encapsulating materials each having a programmable, controllable and/or selectable degradation rate provide a means of transforming the device. In some embodiments, for example, transient devices of the invention combine degradable high performance single crystalline inorganic materials with selectively removable substrates and/or encapsulants.

This description presents a set of materials, modeling tools, manufacturing approaches, device designs and system level examples of transient electronics. The present invention is directed to transient electronic devices incorporating inorganic materials, for example, for structure device components including substrates and encapsulants. Incorporation of inorganic materials in some transient devices of the invention provides a means of engineering overall device properties to achieve a range of performance benefits. In some embodiments, for example, inorganic device materials provide structural components, such as substrates and encapsulant layers, capable of precisely defined and preselected transience properties, such as transience profiles having well-defined temporal and physical properties useful for a range of applications. In some embodiments, for example, inorganic device materials provide structural components, such as substrates and encapsulant layers, that are effective electronic insulating and/or barrier layers prior to a pre-engineered transient device transformation. In some embodiments, for example, inorganic device materials provide structural components, such as substrates and encapsulant layers, that undergo small dimensional changes prior to a pre-engineered transient device transformation, for example, in response to environmental conditions, e.g., exposure to water, biological fluid or other solvent, or in response to a user initiated trigger signal. In some embodiments, for example, inorganic device materials of the invention are compatible with processing approaches and materials strategies capable of achieving precisely controlled physical and chemical properties supporting a range of device applications.

In an embodiment, for example, the invention provides a transient electronic device comprising: (i) a substrate; (ii) one or more active or passive electronic device components supported by said substrate; wherein said active or passive electronic device components independently comprise a selectively transformable material; and (iii) an encapsulant layer at least partially encapsulating said one or more active or passive electronic device components; wherein said substrate, said encapsulant layer or both independently comprise a selectively removable inorganic material responsive to an external or internal stimulus; wherein at least partial removal of said substrate, said encapsulant layer or both in response to said external or internal stimulus initiates at least partial transformation of said one or more active or passive electronic device components providing a programmable transformation of the transient electronic device in response to said external or internal stimulus at a pre-selected time or at a pre-selected rate, wherein said programmable transformation provides a change in function of the transient electronic device from a first condition to a second condition. In an embodiment, for example, said one or more active or passive electronic device components comprise one or more inorganic semiconductor components, one or more metallic conductor components or one or more inorganic semiconductor components and one or more metallic conductor components.

The invention of this aspect includes transient devices wherein the substrate or encapsulant layer comprising a selectively removable inorganic material is completely removed during device transformation or only partially removed (e.g., at least 20%, 30%, 50%, 70% or 90% by weight, volume or area removed) during device transformation. Transient electronic devices of this aspect include passive transient devices and actively triggered transient devices.

In an embodiment, for example, the substrate, the encapsulant layer or both independently comprises an entirely inorganic structure. For example, an entirely inorganic structure may include one or more of $SiO_2$, spin-on-glass, Mg, Mg alloys, Fe, W, Zn, Mo, Si, SiGe, $Si_3N_4$ and MgO. Alternatively, the invention includes transient devices wherein the substrate, the encapsulant layer or both independently comprises a composite inorganic and organic structure, for example, having a multilayer geometry combining one or more layers of an inorganic material and one or more layers of an organic material, such as a polymer material. For example, a composite inorganic and organic structure may comprise an inorganic layer having a first surface adjacent the active or passive electronic device components and a second surface adjacent an organic layer or a composite inorganic and organic structure may comprise an organic layer having a first surface adjacent the active or passive electronic device components and a second surface adjacent the inorganic layer. In an embodiment, the inorganic layer comprises one or more of $SiO_2$, spin-on-glass, Mg, Mg alloys, Fe, W, Zn, Mo, Si, SiGe, $Si_3N_4$ and MgO and the organic layer comprises one or more of a polyanhydride and poly(dimethyl siloxane) (PDMS).

In an embodiment, transient devices of the invention include entirely inorganic devices comprising all inorganic device components, for example, wherein said active or passive electronic device components, said substrate and said encapsulant layer each are independently entirely composed of one or more inorganic materials. Transient devices of the invention include hybrid inorganic—organic devices comprising a combination of one or more inorganic device components comprising metals, ceramics, metal oxides or glasses, and one or more organic device components, for example, comprising a polymer material.

In an embodiment, for example, the substrate, the encapsulant layer or both independently has a preselected transience profile in response to an external or internal stimulus. A range of processing approaches and materials strategies are useful in the present invention for achieving an inorganic substrate and/or encapsulant layer having a preselected transience profile including selection of chemical composition, physical properties, morphology and control of synthesis, growth and/or deposition processes.

Selection of the composition of substrates and encapsulant layers comprising a selectively removable inorganic material is an important aspect for achieving transience properties useful for supporting a range of device functionalities. In an embodiment, the composition of the substrate and/or encapsulant layer is selected to achieve useful electronic, physical and/or transience properties. In an embodiment, for example, the selectively removable inorganic material of the substrate, the encapsulant layer or both independently comprises a metal, a metal oxide, a ceramic or a combination of these. In an embodiment, for example, the selectively removable inorganic material of the substrate or the encapsulant layer independently comprises a crystalline material, an amorphous material or a combination thereof. In an embodiment, for example, the selectively removable inorganic material of the substrate, the encapsulant layer or both independently comprises a single crystalline material, polycrystalline material or doped crystalline material. In an embodiment, for example, the selectively removable inorganic material of the substrate, the encapsulant layer or both independently comprises a glass, such as a spin-on-glass.

In an embodiment, for example, the selectively removable inorganic material of the substrate, the encapsulant layer or both independently comprises a thin film, a coating, a foil or any combination of these. In an embodiment, for example, the selectively removable inorganic material of the substrate, the encapsulant layer or both independently comprises a nanofilm having a thickness ranging from 1 nm to 100 nm or a microfilm having a thickness ranging from 1 μm to 100 μm. In an embodiment, for example, the substrate, the encapsulant layer or both independently comprises a nanostructured layer or a microstructured layer, for example a layer having one or more perforations, cavities and/or channels provided on an external or internal surface of the substrate or encapsulant layer or provided within the substrate or encapsulant layer. In an embodiment, an encapsulation layer entirely encapsulates at least a portion, and optionally all, of the underlying active or passive electronic device components, such as underlying semiconductor components and/or metallic conductor components. In an embodiment, an encapsulation layer encapsulates only a portion of the underlying active or passive electronic device components, such as underlying semiconductor components and/or metallic conductor components (e.g., 90% or less, 70% or less, 30% or less, etc.).

In an embodiment, for example, the selectively removable inorganic material of the substrate, the encapsulant layer or both independently comprises Mg, W, Mo, Fe, Zn, or an alloy thereof. In an embodiment, for example, the selectively removable inorganic material of the substrate, the encapsulant layer or both independently comprises $SiO_2$, MgO, $N_4Si_3$, SiC or any combination of these. In an embodiment, for example, the selectively removable inorganic material of the substrate, the encapsulant layer or both independently comprises a spin-on-glass or solution processable glass. In an embodiment, for example, the selectively removable inorganic material of the substrate, the encapsulant layer or both independently comprises a biocompatible material, a bioinert material or a combination of biocompatible and bioinert materials.

Substrate and encapsulation layers of the present transient electronic devices include multilayer structures, for example, multilayer structures comprising one or more inorganic device component layers and one or more organic device component layers. In an embodiment, for example, a multilayer substrate and encapsulation layers comprise an inorganic layer having a first side in contact (e.g., physical contact or electrical contact) with an organic layer. In an embodiment, for example, a multilayer substrate and encapsulation layers comprise an inorganic layer provided between, and optionally in physical contact with, a plurality of organic layers. Use of multilayer substrate and encapsulation layers having both organic and inorganic layers allows for components having precisely selectable chemical, physical and electronic properties, for example, resistance, inertness, permeability to water, resistance to swelling, chemical stability, optical transmission, etc. In an embodiment, for example, a multilayer substrate or encapsulation layer comprises 2 to 100 layers, and optionally for some applications 5 to 20 layers.

In an embodiment, for example, the substrate, the encapsulant layer or both independently comprises a multilayer structure comprising one or more of a thin film, coating, or foil comprising the selectively removable inorganic material. In an embodiment, for example, the multilayer structure comprises a stack of layers including the one or more thin films, coatings, or foils comprising the selectively removable inorganic material and further including one or more additional layers, such as layers comprising an organic material, such as a polymer layer, or an insulating ceramic material, such as $SiO_2$. Incorporation of organic layers (e.g. polymer layers) or an insulating ceramic material, such as $SiO_2$, into multilayer substrates and encapsulating layers of the invention is beneficial for providing electrical insulation between a conductive component (e.g., metal) of the substrate or encapsulant layer and underlying device components. In addition, incorporation of organic layers (e.g. polymer layers) or an insulating ceramic material, such as $SiO_2$, into multilayer substrates and encapsulating layers of the invention is beneficial for providing a useful overall permeability of the substrate or encapsulating layer, for example, to prevent volume changes via swelling. In an embodiment, for example, a multilayer substrate or encapsulation layer comprises 2 to 100 inorganic layers and 2 to 100 organic layers, optionally where at least a portion of the organic layers are disposed between inorganic layers.

In an embodiment, for example, the multilayer structure of the present substrate or encapsulant layer further comprises one or more electrically insulating layers, barrier layers or any combinations thereof. In some embodiments, a barrier layer of the invention adjusts the permeability of a device component, for example, by decreasing the overall permeability of the component to water, solvent or environmental fluid. In an embodiment, for example, one or more electrically insulating layers or barrier layers are provided in physical contact, electrical contact or both with the one or more thin films, coatings, or foils. In an embodiment, for example, the one or more electrically insulating layers or barrier layers comprises an exterior layer of the multilayer structure. In an embodiment, for example, the one or more electrically insulating layers or barrier layers comprises an interior layer of the multilayer structure in physical contact or electrical contact with the one or more active or passive electronic device components, such as one or more inorganic semiconductor components, one or more metallic conductor components or both. In an embodiment, for example, the one or more electrically insulating layers or barrier layers comprises a polymer, an insulating ceramic, a glass, $SiO_2$, spin-on-glass, MgO or any combination of these.

In an embodiment, for example, the multilayer structure of the present substrate and/or encapsulant layer comprises a metal foil or thin metal film having a first side in physical contact with a first electronically insulating layer or barrier layer. In an embodiment, for example, the first electronically insulating layer or barrier layer is an exterior layer of the multilayer structure or the first electronically insulating layer or barrier layer is an interior layer of the multilayer structure in physical contact or electrical contact with the one or more active or passive electronic device components, such as one or more inorganic semiconductor components, one or more metallic conductor components or both. In an embodiment, for example, the first electronically insulating layer or barrier layer comprises a polymer or insulating ceramic layer or coating, a metal oxide layer or coating, a glass layer or coating or any combination of these. In an embodiment, for example, the multilayer structure comprises the metal foil or thin metal film having a second side coated in contact with a second electronically insulating layer or barrier layer; wherein the metal foil or thin metal film is provided between the first electronically insulating layer or barrier layer and the second electronically insulating layer or barrier layer.

Substrates and encapsulants of certain embodiments comprise selectively removal materials exhibiting a transience profile useful for a particular device application. In an embodiment, for example, at least partial removal of the substrate, the encapsulant layer or both exposes the one or more active or passive electronic device components, such as one or more inorganic semiconductor components or one or more metallic conductor components, to the external or internal stimulus, thereby initiating the at least partial transformation of the one or more active or passive electronic device components, such as one or more inorganic semiconductor components or the one or more metallic conductor components. In an embodiment, for example, at least partial removal of the substrate, the encapsulant layer or both in response to the internal or external stimulus occurs via a phase change, dissolution, hydrolysis, bioresorption, etching, corrosion, a photochemical reaction, an electrochemical reaction or any combination of these processes.

In an embodiment, at least partial removal of the substrate, encapsulant layer or both occurs by a process other than bioresorption. In another embodiment, at least partial removal of the substrate, encapsulant layer or both occurs via at least partial dissolution of the selectively removable inorganic material in a solvent. The solvent may be an aqueous solvent or a nonaqueous solvent. An "aqueous solvent" is a liquid at 298 K that predominantly comprises water, i.e., greater than 50% v/v water, whereas a "nonaqueous solvent" is a liquid at 298 K that predominantly comprises liquid(s) other than water, i.e., less than 50% v/v water. Exemplary aqueous solvents include water, water-based solutions, bodily fluids, and the like. Exemplary nonaqueous solvents include organic solvents (e.g., alcohols, esters, ethers, alkanes, ketones) and ionic liquids. In another embodiment, at least partial removal of the substrate, encapsulant layer or both occurs via at least partial hydrolysis of the selectively removable inorganic material. In another embodiment, at least partial removal of the substrate, encapsulant layer or both occurs via at least partial etching or corrosion of the selectively removable inorganic material. In another embodiment, at least partial removal of the substrate, encapsulant layer or both occurs by a photochemical reaction wherein at least a portion of the selectively removable inorganic material absorbs electromagnetic radiation and undergoes an at least partial chemical or physical change. In an embodiment, the photochemical reaction is a photodecomposition process. In another embodiment, at least partial removal of the substrate, encapsulant layer or both occurs by an electrochemical reaction. For example, the electrochemical reaction may be at least partial anodic dissolution of the selectively removable inorganic material of the substrate, encapsulant layer or both.

In an embodiment, for example, the substrate, the encapsulant layer or both independently have a preselected transience profile characterized by a removal of 0.01% to 100% by weight of the substrate or the encapsulant layer over a time interval selected from the range of 1 ms to 5 years, or 1 ms to 2 years, or 1 ms to 1 year, or 1 ms to 6 months, or 1 ms to 1 month, or 1 ms to 1 day, or 1 ms to 1 hour, or 1 second to 10 minutes. In an embodiment, for example, the substrate, the encapsulant layer or both independently have a preselected transience profile characterized by a decrease in average thickness of the substrate or the encapsulant layer at a rate selected over the range of 0.01 nm/day to 100 microns $s^{-1}$, or 0.01 nm/day to 10 microns $s^{-1}$, or 0.1 nm/day to 1 micron $s^{-1}$, or 1 nm/day to 0.5 micron $s^{-1}$. In an embodiment, for example, the substrate or the encapsulant layer or both independently has a porosity selected from the range of 0.01% to 99.9% prior to the at least partial removal of the substrate, the encapsulant layer or both in response to the external or internal stimulus.

The physical properties of substrates and encapsulation layers comprising a selectively removable inorganic material may be selected to achieve desired transience properties. In an embodiment, for example, the substrate, the encapsulant layer or both independently has an extent of crystallinity selected from the range of 0.1% to 100%, or 0.1% to 99.9%, or 1% to 90%, or 5% to 80%, or 10% to 60%, or 15% to 40% prior to the at least partial removal of the substrate, the encapsulant layer or both in response to the external or internal stimulus. In an embodiment, for example, the encapsulant layer or both independently has a density selected from the range of 0.1% to 100%, or 0.1% to 99.9%, or 1% to 90%, or 5% to 80%, or 10% to 60%, or 15% to 40% compared to bulk prior to the at least partial removal of the substrate, the encapsulant layer or both in response to the external or internal stimulus. In an embodiment, for example, a time for a thickness of the selectively removable material to reach zero is provided by the expression:

$$t_c = \frac{4\rho_m M(H_2O)}{kw_0 M(m)} \frac{\sqrt{\frac{kh_0^2}{D}}}{\tanh\sqrt{\frac{kh_0^2}{D}}};$$ (EX1);

where $t_c$ is the critical time, $\rho_m$ is the mass density of the material, $M(H_2O)$ is the molar mass of water, $M(m)$ is the molar mass of the material, $h_0$ is the initial thickness of the material, $D$ is the diffusivity of water, $k$ is the reaction constant for the dissolution reaction, and $w_0$ is the initial concentration of water; wherein k has a value selected from the range of $1\times10^5$ $S^{-1}$ to $1\times10^{-10}$ $s^{-1}$.

Substrates and encapsulant layers comprising a selectively removable inorganic material may have a range of physical, electronic and chemical properties useful for a particular application. In an embodiment, for example, the substrate, the encapsulant layer or both are substantially impermeable to water prior to the at least partial removal of the substrate, the encapsulant layer or both in response to the external or internal stimulus. In an embodiment, for example, the substrate, the encapsulant layer or both limit a net leakage current to the surroundings to 0.1 µA/cm² or less prior to the at least partial removal of the substrate, the encapsulant layer or both in response to the external or internal stimulus. In an embodiment, for example, the substrate, the encapsulant layer or both undergo an increase in volume equal to or less than 10%, or equal to or less than 5%, or equal to or less than 3%, or equal to or less than 1% upon exposure to an aqueous or nonaqueous solvent prior to the at least partial removal of the substrate, the encapsulant layer or both in response to the external or internal stimulus. In an embodiment, for example, a thin film, coating, or foil of the substrate or encapsulant layer has an average thickness over or underneath of the one or more active or passive electronic device components, such as one or more inorganic semiconductor components or one or more metallic conductor components, less than or equal to 1000 µm, or less than or equal to 500 µm, or less than or equal to 250 µm, or less than or equal to 100 µm, or less than or equal to 50 µm prior to the at least partial removal of the substrate, the encapsulant layer or both in response to the external or internal stimulus. In an embodiment, for example, the substrate, the encapsulant layer or both independently has a thickness selected from the range of 0.1 µm to 1000 µm, or of 1 µm to 500 µm, or of 5 µm to 100 µm, or of 10 µm to 50 µm prior to the at least partial removal of the substrate, the encapsulant layer or both in response to the external or internal stimulus. In an embodiment, for example, the substrate, the encapsulant layer or both independently has an average modulus selected over the range of 0.5 KPa to 10 TPa, or of 5 KPa to 1 TPa, or of 50 KPa to 1 TPa, or of 5 GPa to 500 GPa. In an embodiment, for example, the substrate, the encapsulant layer or both independently has a net flexural rigidity less than or equal to $1\times10^{-4}$ Nm. In an embodiment, for example, the substrate, the encapsulant layer or both independently has a net bending stiffness less than or equal to $1\times10^8$ GPa µm⁴, or less than or equal to $1\times10^6$ GPa µm⁴, or less than or equal to $1\times10^5$ GPa µm⁴, or less than or equal to $1\times10^3$ GPa µm⁴. In an embodiment, for example, the substrate, the encapsulant layer or both are at least partially optically transparent in the visible or infrared regions of the electromagnetic spectrum.

Useful substrates and encapsulating layers comprising a selectively removable inorganic material may be fabricated via a range of processing approaches, including deposition techniques, solution processing and spin casting. In an embodiment, for example, the substrate, the encapsulant layer or both is generated via physical vapor deposition, chemical vapor deposition, sputtering, atomic layer deposition, electrochemical deposition, spin casting, electrohydrodynamic jet printing, screen printing or any combination of these. In an embodiment, for example, the substrate, the encapsulant layer or both covers or supports a percentage of an exterior area or volume or an interior area or volume of the one or more active or passive electronic device components, such as one or more inorganic semiconductor components, one or more metallic conductor components or both, selected from the range of 1% to 100%, optionally selected over the range of 10 to 50%. In an embodiment, for example, the substrate, the encapsulant layer or both covers or supports 10% or more, optionally 30% or more, of an exterior area or an interior area of the one or more inorganic semiconductor components, one or more metallic conductor components or both.

In an embodiment, the one or more active or passive electronic device components comprise one or more one or more inorganic semiconductor components. In an embodiment, for example, the one or more inorganic semiconductor components comprise a polycrystalline semiconductor material, a single crystalline semiconductor material or a doped polycrystalline or single crystalline semiconductor material. In an embodiment, for example, the one or more inorganic semiconductor components comprise Si, Ga, GaAs, ZnO or any combination of these. In an embodiment, the one or more active or passive electronic device components comprise one or more one or more metallic conductor components. In an embodiment, for example, the one or more metallic conductor components comprise Mg, W, Mo, Fe, Zn or an alloy thereof. In an embodiment, for example, the one or more active or passive electronic device components comprise a component of an electronic device selected from the group consisting of a transistor, a diode, an amplifier, a multiplexer, a light emitting diode, a laser, a photodiode, an integrated circuit, a sensor, a temperature sensor, an electrochemical cell, a thermistor, a heater, a resistive heater, an antenna, a nanoelectromechanical system or a microelectromechanical system, an actuator and arrays thereof.

In an embodiment, for example, the device is a communication system, a photonic device, a sensor, an optoelectronic device, a biomedical device, a temperature sensor, a photodetector, a photovoltaic device, a strain gauge, and imaging system, a wireless transmitter, an electrochemical cell, an antenna, a nanoelectromechanical system, an energy storage system, an actuator or a microelectromechanical system.

In an embodiment, a transient electronic device has a preselected transience profile characterized by the transformation of the one or more active or passive electronic device components, such as one or more inorganic semiconductor components or the one or more metallic conductor components, occurring over a time interval selected from the range of 1 ms to 2 years, or 1 ms to 1 year, or 1 ms to 6 months, or 1 ms to 1 month, or 1 ms to 1 day, or 1 ms to 1 hour, or 1 second to 10 minutes, thereby providing the programmable transformation of the passive transient electronic device. In an embodiment, the preselected transience profile is characterized by a transformation of 0.01% to 100%, or 0.1% to 70%, or 0.5% to 50%, or 1% to 20% or 1% to 10% of the one or more active or passive electronic device components, such as one or more inorganic semiconductor components or the one or more metallic conductor components, over a time interval selected from the range of 1 ms to 2 years, or 1 ms to 1 year, or 1 ms to 6 months, or 1 ms to 1 month, or 1 ms to 1 day, or 1 ms to 1 hour, or 1 second to 10 minutes, thereby providing the programmable transformation of the passive transient electronic device. In an embodiment, the preselected transience profile is characterized by a decrease in the average thickness of the one or more active or passive electronic device components, such as one or more inorganic semiconductor components or the one or more metallic conductor components, at a rate selected over the range of 0.01 nm/day to 10 microns $s^{-1}$, or 0.1 nm/day to 1 micron $s^{-1}$, or 1 nm/day to 0.5 micron $s^{-1}$. In an embodiment, the preselected transience profile is characterized by a decrease in the mass of the one or more active or passive electronic device components, such as one or more inorganic semiconductor components or the one or more metallic conductor components, at a rate selected over the range of 0.01 nm/day to 10 microns $s^{-1}$, or 0.1 nm/day to 1 micron $s^{-1}$, or 1 nm/day to 0.5 micron $s^{-1}$. In an embodiment, the preselected transience profile is characterized by a decrease in the electrical conductivity of the one or more active or passive electronic device components, such as one or more inorganic semiconductor components or the one or more metallic conductor components, at a rate selected over the range of $10^{10}$ S·m$^{-1}$ s$^{-1}$ to 1 S·m$^{-1}$ s$^{-1}$, or $10^8$ S·m$^{-1}$ s$^{-1}$ to 10 S·m$^{-1}$ s$^{-1}$, or $10^5$ S·m$^{-1}$ s$^{-1}$ to 100 S·m$^{-1}$ s$^{-1}$.

The physical dimensions and shape of the device, and components thereof, are important parameters, particularly with respect to preselection of a desired transience profile. Use of thin electronic device components, such as inorganic semiconductor components, metallic conductor components and/or dielectric components (e.g., thickness less than or equal to 100 microns, optionally thickness less than or equal to 10 microns, optionally thickness less than or equal to 1 micron, optionally thickness less than or equal to 500 nanometers, and optionally thickness less than or equal to 100 nanometers) is beneficial for providing a preselected transience for a given device application and/or providing useful mechanical properties such as a flexible or otherwise deformable device. In some embodiments, inorganic semiconductor components, metallic conductor components and/or dielectric components independently comprise one or more thin film structures, which may for example be deposited or grown by molecular epitaxy, atomic layer deposition, physical or chemical vapor deposition, or other methods known in the art. In some embodiments, one or more inorganic semiconductor components, metallic conductor components and/or dielectric components independently comprise a biocompatible, bioresorbable, bioinert or eco-compatible material. In some embodiments, at least some of, and optionally all of, the inorganic semiconductor components, metallic conductor components and/or dielectric components of the electronic device have a thickness less than or equal to 100 microns, and for some applications have a thickness less than or equal to 10 microns, and for some applications have a thickness less than or equal to 1 micron, and for some applications have a thickness less than or equal to 500 nanometers, and for some applications have a thickness less than or equal to 100 nanometers, and for some applications have a thickness less than or equal to 20 nanometers. In some embodiments, at least some of, and optionally all of, the inorganic semiconductor components, metallic conductor components and/or dielectric components of the device independently have a thickness selected from a range of 10 nm to 100 μm, optionally for some applications selected from a range of 50 nm to 10 μm, and optionally for some applications selected from a range of 100 nm to 1000 nm. In an embodiment, for example, a device of the invention comprises one or more inorganic semiconductor components each independently having a thickness selected over the range of 10 nm to 1000 nm, optionally for some applications 10 nm to 100 nm and optionally for some applications 10 nm to 30 nm. In some embodiments, at least some of, and optionally all of, the inorganic semiconductor components, metallic conductor components and/or dielectric components of the device independently have lateral physical dimensions (e.g., length, width, diameter, etc.) less than or equal to 10000 μm, and for some applications have lateral physical dimensions less than or equal to 1000 μm, and for some applications have lateral physical dimensions less than or equal to 100 μm, and for some applications have lateral physical dimensions less than or equal to 1 μm. In some embodiments, at least some of, and optionally all of, the inorganic semiconductor components, metallic conductor components and/or dielectric components of the device independently have lateral physical dimensions selected from the range of 10 nm to 10 cm, optionally for some applications selected from a range of 100 nm to 10000 μm, optionally for some applications selected from a range of 500 nm to 1000 μm, optionally for some applications selected from a range of 500 nm to 100 μm, and optionally for some applications selected from a range of 500 nm to 10 μm.

The physical properties of the semiconductor components, metallic conductor components and/or selectively removable inorganic material components (e.g., Young's modulus, net bending stiffness, toughness, conductivity, resistance, etc.) impact the performance and transience of the device. In some embodiments, for example, at least a portion, and optionally all, of the semiconductor components, metallic conductor components and/or selectively removable inorganic material components of the device independently have a Young's modulus less than or equal to 10 GPa, optionally for some applications less than or equal to 100 MPa, optionally for some applications less than or equal to 10 MPa. In some embodiments, for example, at least a portion, and optionally all, of the semiconductor components, metallic conductor components and/or selectively removable inorganic material components of the device have a Young's modulus selected over the range of 0.5 MPa and 10 GPa, and optionally for some applications selected over the range of 0.5 MPa and 100 MPa, and optionally for some applications selected over the range of 0.5 MPa and 10 MPa. In some embodiments, at least a portion, and optionally all, of the semiconductor components, metallic conductor components and/or selectively removable inorganic material components of the device have a net bending stiffness less than or equal to $1\times10^8$ GPa $\mu m^4$, optionally for some applications less than or equal to $5\times10^5$ GPa $\mu m^4$ and optionally for some applications less than or equal to $1\times10^5$ GPa $\mu m^4$. In some embodiments, at least a portion, and optionally all, of the semiconductor components, metallic conductor components and/or selectively removable inorganic material components of the device have a net bending stiffness selected over the range of $0.1\times10^4$ GPa $\mu m^4$ and $1\times10^8$ GPa $\mu m^4$, and optionally for some applications between $0.1\times10$ GPa $\mu m^4$ and $5\times10^5$ GPa $\mu m^4$.

Useful materials for the inorganic semiconductor components include high quality semiconductor materials such as single crystalline semiconductor materials including pure and doped single crystalline semiconductor materials. In an embodiment, all of the inorganic semiconductor components comprise a single crystalline semiconductor material and/or a single crystalline doped semiconductor material, for example, single crystalline silicon and/or doped single crystalline silicon derived from high temperature foundry processing. Integration of single crystalline semiconductor materials into a transient device is particularly beneficial for providing devices exhibiting very good electronic properties. In an embodiment, the semiconductor components comprise a material selected from the group consisting of Si, Ge, Se, diamond, fullerenes, SiC, SiGe, SiO, $SiO_2$, SiN, AlSb, AlAs, AlIn, AlN, AlP, AlS, BN, BP, BAs, $As_2S_3$, GaSb, GaAs, GaN, GaP, GaSe, InSb, InAs, InN, InP, CsSe, CdS, CdSe, CdTe, $Cd_3P_2$, $Cd_3As_2$, $Cd_3Sb_2$, ZnO, ZnSe, ZnS, ZnTe, $Zn_3P_2$, $Zn_3As_2$, $Zn_3Sb_2$, $ZnSiP_2$, CuCl, PbS, PbSe, PbTe, FeO, $FeS_2$, NiO, EuO, EuS, PtSi, TlBr, $CrBr_3$, SnS, SnTe, $PbI_2$, $MoS_2$, GaSe, CuO, $Cu_2O$, HgS, HgSe, HgTe, $HgI_2$, MgS, MgSe, MgTe, CaS, CaSe, SrS, SrTe, BaS, BaSe, BaTe, $SnO_2$, TiO, $TiO_2$, $Bi_2S_3$, $Bi_2O_3$, $Bi_2Te_3$, $BiI_3$, $UO_2$, $UO_3$, $AgGaS_2$, $PbMnTe$, $BaTiO_3$, $SrTiO_3$, $LiNbO_3$, $La_2CuO_4$, $La_{0.7}Ca_{0.3}MnO_3$, CdZnTe, CdMnTe, $CuInSe_2$, copper indium gallium selenide (CIGS), HgCdTe, HgZnTe, HgZnSe, PbSnTe, $Tl_2SnTe_5$, $Tl_2GeTe_5$, AlGaAs, AlGaN, AlGaP, AlInAs, AlInSb, AlInP, AlInAsP, AlGaAsN, GaAsP, GaAsN, GaMnAs, GaAsSbN, GaInAs, GaInP, AlGaAsSb, AlGaAsP, AlGaInP, GaInAsP, InGaAs, InGaP, InGaN, InAsSb, InGaSb, InMnAs, InGaAsP, InGaAsN, InAlAsN, GaInNAsSb, GaInAsSbP, and any combination of these. In some embodiments, the inorganic semiconductor components include a material selected from the group consisting of Si, SiC, SiGe, SiO, $SiO_2$, SiN, and any combination of these. In some embodiments, the inorganic semiconductor components independently comprise single crystalline silicon, porous silicon and/or polycrystalline silicon. In some embodiments, the inorganic semiconductor components independently comprise a polycrystalline semiconductor material, single crystalline semiconductor material or doped polycrystalline or single crystalline semiconductor material. In some embodiments, the inorganic semiconductor component is a transformable material. Useful materials for a transformable, inorganic semiconductor component include, but are not limited to, porous silicon, polycrystalline silicon, and any combination of these.

In some embodiments, electronic devices comprise one or more interconnected island and bridge structures. For example, an island structure may comprise one or more semiconductor circuit components of the transient device. A bridge structure may comprise one or more flexible and/or stretchable electrical interconnections providing electrical communication between elements, for example between different island structures. In this manner, electronic devices of the present invention may comprise stretchable electronic devices having a plurality of electrically interconnected inorganic semiconductor components comprising one or more island structures and one or more flexible and/or stretchable bridge structures providing electrical interconnection; e.g., stretchable electronic interconnects.

In some embodiments, the transient device, or components thereof, are assembled on the substrate via a printing-based or molding-based process, for example, by transfer printing, dry contact transfer printing, solution-based printing, soft lithography printing, replica molding, imprint lithography, etc. In some of these embodiments, therefore, the device, or components thereof, comprise printable semiconductor materials and/or devices. Integration of the device and substrate components via a printing-based technique is beneficial in some embodiments, as it allows for independent processing of semiconductor devices/materials and processing for the substrate. For example, the printing-based assembly approach allows semiconductor devices/materials to be processed via techniques that would not be compatible with some substrates. In some embodiments, for example, the semiconductor devices/materials are first processed via high temperature processing, physical and chemical deposition processing, etching and/or aqueous processing (e.g. developing, etc.), and then subsequently assembled on the substrate via a printing-based technique. An advantage of this approach is that it avoids processing of the semiconductor devices/materials on the substrate in a manner that could negatively impact the chemical and/or physical properties of the substrate, for example, by negatively impacting biocompatibility, toxicity and/or the degradation properties (e.g., degradation rate, etc.) of the transformable substrate. In some embodiments, for example, this approach allows for effective fabrication of the device without exposing the substrate to aqueous processing, for example, processing involving exposure of the transformable substrate to an etchant, a stripper or a developer.

In some embodiments, the transient device may include one or more additional device components selected from the group consisting of an electrode, a dielectric layer, a chemical or biological sensor element, a pH sensor, an optical sensor, an optical source, a temperature sensor, and a capacitive sensor. The additional device component may comprise a bioinert material, a degradable material or a transformable material. Useful bioinert materials include, but are not limited to, titanium, gold, silver, platinum and any combination of these. Useful degradable or transformable materials include, but are not limited to, iron, magnesium, tungsten and any combination of these.

In an aspect, the invention provides a method of using a transient electronic device, the method comprising the steps of: (i) providing the transient electronic device comprising: (1) a substrate; (2) one or more active or passive electronic device components supported by said substrate; wherein said active or passive electronic device components independently comprise a selectively transformable material; and (3) an encapsulant layer at least partially encapsulating said one or more active or passive electronic device components; wherein said substrate, said encapsulant layer or both independently comprise a selectively removable inorganic material responsive to an external or internal stimulus; wherein at least partial removal of said substrate, said encapsulant layer or both in response to said external or internal stimulus initiates at least partial transformation of said one or more active or passive electronic device components providing a programmable transformation of the transient electronic device in response to said external or internal stimulus at a pre-selected time or at a pre-selected rate, wherein said programmable transformation provides a change in function of the transient electronic device from a first condition to a second condition; and (ii) exposing said transient electronic device to said external or internal stimulus resulting in said at least partial removal of said substrate or encapsulant layer to expose said one or more active or passive electronic device components to said external or internal stimulus, thereby providing said programmable transformation of the transient electronic device. In an embodiment of this aspect, for example, said one or more active or passive electronic device components comprise one or more inorganic semiconductor components, one or more metallic conductor components or one or more inorganic semiconductor components and one or more metallic conductor components.

In an embodiment, for example, the invention provides a method wherein said removal of said substrate, said encapsulant layer or both in response to said internal or external stimulus occurs via a phase change, dissolution, hydrolysis, bioresorption, etching, corrosion, a photochemical reaction, an electrochemical reaction or any combination of these processes. In an embodiment, for example, the invention provides a method wherein said step of exposing said transient electronic device to said external or internal stimulus results in the entire removal of said substrate, said encapsulant layer or both. In an embodiment, for example, the invention provides a method wherein said step of exposing said transient electronic device to said external or internal stimulus results in less than the entire removal of said substrate, said encapsulant layer or both. In an embodiment, for example, the invention provides a method wherein said step of exposing said transient electronic device to said external or internal stimulus exposes at least 1% of an outer surface of said one or more active or passive electronic device components, optionally for some applications at least 10% of an outer surface of said one or more active or passive electronic device components, and optionally for some applications at least 50% of an outer surface of said one or more active or passive electronic device components. In an embodiment, for example, the invention provides a method wherein said step of exposing said transient electronic device to said external or internal stimulus exposes 1% to 100% of an outer surface of said one or more active or passive electronic device components, optionally for some applications 10% to 100% of an outer surface of said one or more active or passive electronic device components, optionally for some applications 50% to 100% of an outer surface of said one or more active or passive electronic device components In an aspect, the invention provides a method of making a transient electronic device, said method comprising the steps of: (i) providing a substrate; (ii) providing on said substrate one or more active or passive electronic device components; wherein said active or passive electronic device components independently comprise a selectively transformable material; and (iii) at least partially encapsulating said one or more active or passive electronic device components with an encapsulant layer; wherein said substrate, said encapsulant layer or both independently comprise a selectively removable inorganic material responsive to an external or internal stimulus; wherein at least partial removal of said substrate, said encapsulant layer or both in response to said external or internal stimulus initiates at least partial transformation of said one or more active or passive electronic device components providing a programmable transformation of the transient electronic device in response to said external or internal stimulus at a pre-selected time or at a pre-selected rate, wherein said programmable transformation provides a change in function of the transient electronic device from a first condition to a second condition.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIGS. 1A-1D provide schematic diagrams illustrating side views of transient electronic devices of the invention.

FIG. 7(A) Measured data (symbols) and numerical fits (lines) for pH-dependent dissolution kinetics of oxides (black, tg-oxide by dry oxidation; red, tg-oxide by wet oxidation; blue, PECVD oxide; magenta, E-beam oxide)

at room temperature and 37° C. FIG. 7(B) $SiO_2$ film property dependency exhibited as film density versus dissolution rate.

FIG. 9(A) pH-dependent dissolution kinetics of nitrides (black, LPCVD nitride; red, PECVD nitride with LF mode; blue, PE-CVD nitride with HF mode) at room temperature and 37° C. FIG. 9(B) $SiN_X$ film property dependency exhibited as film density versus dissolution rate.

FIG. 22(A) Transistor array on Fe foil (~10 µm thick), FIG. 22(B) Diode array on Zn foil (~10 µm thick), FIG. 22(C) Capacitor array on Mo foil (~10 µm thick), FIG. 22(D) Inductor array on Mo foil (~10 µm thick).

FIG. 22(A) Transistor on Mo foil with MgO encapsulation (~800 nm), FIG. 22(B) Diode on Mo foil with MgO encapsulation (~800 nm), FIG. 22(C) Capacitor on Mo foil with MgO encapsulation (~800 nm), FIG. 22(D) Inductor on Mo foil with MgO encapsulation.

FIG. 39A-39E. FIG. 39(A) Structures of the components of mixture 7A of Table 3 showing reactive groups. FIG. 39(B) Component ratios and indication that degradation rate increases as hydrophobicity decreases. FIG. 39(C) Reaction scheme for forming a polyanhydride encapsulant material comprising a phosphodiester group within the polymeric chain. FIG. 39(D) Reaction scheme for forming a polyanhydride encapsulant material comprising a silyl ether group within the polymeric chain. FIG. 39(E) Reaction scheme for forming a polyanhydride encapsulant material comprising an ether group within the polymeric chain.

DETAILED DESCRIPTION OF THE INVENTION

Figure 1A:
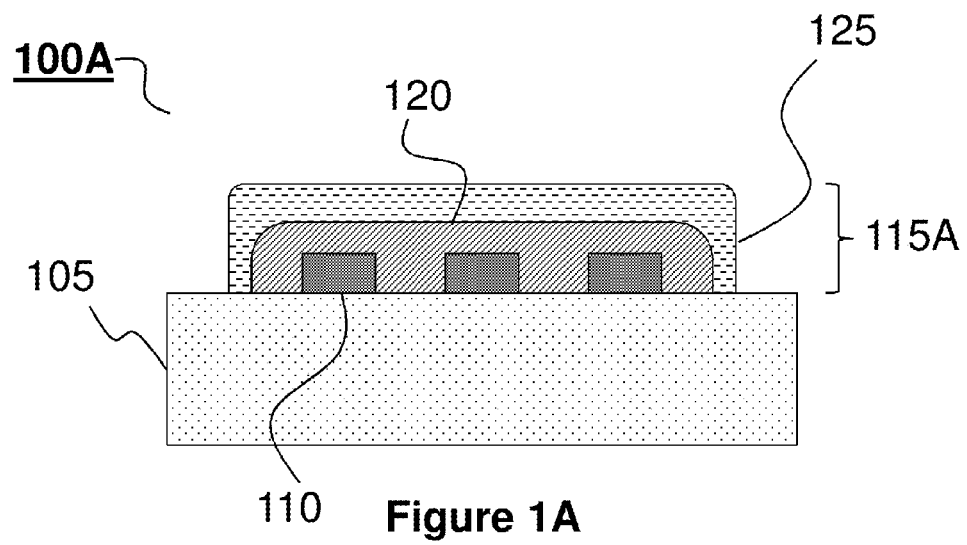
FIG. 1A-1D.

In general, the terms and phrases used herein have their art-recognized meaning, which can be found by reference to standard texts, journal references and contexts known to those skilled in the art. The following definitions are provided to clarify their specific use in the context of the invention.

"Functional layer" refers to a layer that imparts some functionality to the device. For example, the functional layer may contain semiconductor components, metallic components, dielectric components, optical components, piezoelectric components, etc. Alternatively, the functional layer may comprise multiple layers, such as multiple semiconductor layers, metallic layers or dielectric layers separated by support layers. The functional layer may comprise a plurality of patterned elements, such as interconnects running between electrodes or islands. The functional layer may be heterogeneous or may have one or more properties that are inhomogeneous. "Inhomogeneous property" refers to a physical parameter that can spatially vary, thereby effecting the position of the neutral mechanical plane within a multilayer device.

"Structural layer" refers to a layer that imparts structural functionality, for example by supporting, securing and/or encapsulating device components. The invention includes transient devices having one or more structural layers, such as encapsulating layers, embedding layers, adhesive layers and/or substrate layers.

"Semiconductor" refers to any material that is an insulator at a very low temperature, but which has an appreciable electrical conductivity at a temperature of about 300 Kelvin. In the present description, use of the term semiconductor is intended to be consistent with use of this term in the art of microelectronics and electronic devices. Useful semiconductors include those comprising elemental semiconductors, such as silicon, germanium and diamond, and compound semiconductors, such as group IV compound semiconductors such as SiC and SiGe, group III-V semiconductors such as AlSb, AlAs, AlN, AlP, BN, BP, BAs, GaSb, GaAs, GaN, GaP, InSb, InAs, InN, and InP, group III-V ternary semiconductors alloys such as $Al_xGa_{1-x}As$, group II-VI semiconductors such as CsSe, CdS, CdTe, ZnO, ZnSe, ZnS, and ZnTe, group I-VII semiconductors such as CuCl, group IV-VI semiconductors such as PbS, PbTe, and SnS, layer semiconductors such as $PbI_2$, $MoS_2$, and GaSe, oxide semiconductors such as CuO and $Cu_2O$. The term semiconductor includes intrinsic semiconductors and extrinsic semiconductors that are doped with one or more selected materials, including semiconductors having p-type doping materials and n-type doping materials, to provide beneficial electronic properties useful for a given application or device. The term semiconductor includes composite materials comprising a mixture of semiconductors and/or dopants. Specific semiconductor materials useful for some embodiments include, but are not limited to, Si, Ge, Se, diamond, fullerenes, SiC, SiGe, SiO, $SiO_2$, SiN, AlSb, AlAs, AlIn, AlN, AlP, AlS, BN, BP, BAs, $As_2S_3$, GaSb, GaAs, GaN, GaP, GaSe, InSb, InAs, InN, InP, CsSe, CdS, CdSe, CdTe, $Cd_3P_2$, $Cd_3As_2$, $Cd_3Sb_2$, ZnO, ZnSe, ZnS, ZnTe, $Zn_3P_2$, $Zn_3As_2$, $Zn_3Sb_2$, $ZnSi\,P_2$, CuCl, PbS, PbSe, PbTe, FeO, $FeS_2$, NiO, EuO, EuS, PtSi, TlBr, $CrBr_3$, SnS, SnTe, $PbI_2$, $MoS_2$, GaSe, CuO, $Cu_2O$, HgS, HgSe, HgTe, $HgI_2$, MgS, MgSe, MgTe, CaS, CaSe, SrS, SrTe, BaS, BaSe, BaTe, $SnO_2$, TiO, $TiO_2$, $Bi_2S_3$, $Bi_2O_3$, $Bi_2Te_3$, $BiI_3$, $UO_2$, $UO_3$, $AgGaS_2$, PbMnTe, $BaTiO_3$, $SrTiO_3$, $LiNbO_3$, $La_2CuO_4$, $La_{0.7}Ca_{0.3}MnO_3$, CdZnTe, CdMnTe, $CuInSe_2$, copper indium gallium selenide (CIGS), HgCdTe, HgZnTe, HgZnSe, PbSnTe, $Tl_2SnTe_5$, $Tl_2GeTe_5$, AlGaAs, AlGaN, AlGaP, AlInAs, AlInSb, AlInP, AlInAsP, AlGaAsN, GaAsP, GaAsN, GaMnAs, GaAsSbN, GaInAs, GaInP, AlGaAsSb, AlGaAsP, AlGaInP, GaInAsP, InGaAs, InGaP, InGaN, InAsSb, InGaSb, InMnAs, InGaAsP, InGaAsN, InAlAsN, GaInNAsSb, GaInAsSbP, and any combination of these. Porous silicon semiconductor materials are useful for aspects described herein. Impurities of semiconductor materials are atoms, elements, ions and/or molecules other than the semiconductor material(s) themselves or any dopants provided to the semiconductor material. Impurities are undesirable materials present in semiconductor materials which may negatively impact the electronic properties of semiconductor materials, and include but are not limited to oxygen, carbon, and metals including heavy metals. Heavy metal impurities include, but are not limited to, the group of elements between copper and lead on the periodic table, calcium, sodium, and all ions, compounds and/or complexes thereof.

A "semiconductor component" broadly refers to any semiconductor material, composition or structure, and expressly includes high quality single crystalline and polycrystalline semiconductors, semiconductor materials fabricated via high temperature processing, doped semiconductor materials, inorganic semiconductors, and composite semiconductor materials.

A "component" is used broadly to refer to an individual part of a device. An "interconnect" is one example of a component, and refers to an electrically conducting structure capable of establishing an electrical connection with another component or between components. In particular, an interconnect may establish electrical contact between components that are separate. Depending on the desired device specifications, operation, and application, an interconnect is made from a suitable material. Suitable conductive materials include semiconductors and metallic conductors.

Other components include, but are not limited to, thin film transistors (TFTs), transistors, diodes, electrodes, integrated circuits, circuit elements, control elements, photovoltaic elements, photovoltaic elements (e.g. solar cell), sensors, light emitting elements, actuators, piezoelectric elements, receivers, transmitters, microprocessors, transducers, islands, bridges and combinations thereof. Components may be connected to one or more contact pads as known in the art, such as by metal evaporation, wire bonding, and application of solids or conductive pastes, for example. Electronic devices of the invention may comprise one or more components, optionally provided in an interconnected configuration.

"Neutral mechanical plane" (NMP) refers to an imaginary plane existing in the lateral, b, and longitudinal, I, directions of a device. The NMP is less susceptible to bending stress than other planes of the device that lie at more extreme positions along the vertical, h, axis of the device and/or within more bendable layers of the device. Thus, the position of the NMP is determined by both the thickness of the device and the materials forming the layer(s) of the device. In an embodiment, a device of the invention includes one or more inorganic semiconductor components, one or more metallic conductor components or one or more inorganic semiconductor components and one or more metallic conductor components provided coincident with, or proximate to, the neutral mechanical plane of the device.

"Coincident" refers to the relative position of two or more objects, planes or surfaces, for example a surface such as a neutral mechanical plane that is positioned within or adjacent to a layer, such as a functional layer, substrate layer, or other layer. In an embodiment, a neutral mechanical plane is positioned to correspond to the most strain-sensitive layer or material within the layer.

"Proximate" refers to the relative position of two or more objects, planes or surfaces, for example a neutral mechanical plane that closely follows the position of a layer, such as a functional layer, substrate layer, or other layer while still providing desired conformability without an adverse impact on the strain-sensitive material physical properties. "Strain-sensitive" refers to a material that fractures or is otherwise impaired in response to a relatively low level of strain. In general, a layer having a high strain sensitivity, and consequently being prone to being the first layer to fracture, is located in the functional layer, such as a functional layer containing a relatively brittle semiconductor or other strain-sensitive device element. A neutral mechanical plane that is proximate to a layer need not be constrained within that layer, but may be positioned proximate or sufficiently near to provide a functional benefit of reducing the strain on the strain-sensitive device element when the device is conformed to a tissue surface. In some embodiments, proximate to refers to a position of a first element within 100 microns of a second element, or optionally within 10 microns for some embodiments, or optionally within 1 micron for some embodiments.

"Electronic device" generally refers to a device incorporating a plurality of components, and includes large area electronics, printed wire boards, integrated circuits, component arrays, biological and/or chemical sensors, physical sensors (e.g., temperature, strain, etc.), nanoelectromechanical systems, microelectromechanical systems, photovoltaic devices, communication systems, medical devices, optical devices, energy storage systems, actuators and electro-optic devices.

"Sensing" refers to detecting the presence, absence, amount, magnitude or intensity of a physical and/or chemical property. Useful electronic device components for sensing include, but are not limited to electrode elements, chemical or biological sensor elements, pH sensors, temperature sensors, strain sensors, mechanical sensors, position sensors, optical sensors and capacitive sensors.

"Actuating" refers to stimulating, controlling, or otherwise affecting a structure, material or device component, such as one or more inorganic semiconductor components, one or more metallic conductor components or an encapsulating material or layer. In an embodiment, actuating refers to a process in which a structure or material is selectively transformed, for example, so as to undergo a chemical or physical change such as removal, loss or displacement of a material or structure. Useful electronic device components for actuating include, but are not limited to, electrode elements, electromagnetic radiation emitting elements, light emitting diodes, lasers, magnetic elements, acoustic elements, piezoelectric elements, chemical elements, biological elements, and heating elements.

An "actuator" is a device component that directly or indirectly initiates at least partial transformation of a transient electronic device in response to a user initiated external trigger signal, for example by initiating an at least partial transformation of a selectively transformable material of a transient electronic device. For example, an actuator may initiate at least partial transformation of a transient device by absorbing energy supplied to the device and utilizing or converting that energy to affect the at least partial transformation. For example, an actuator may initiate at least partial transformation of a transient device by exposing a device component comprising selectively transformable material to an internal or external stimulus resulting in an at least partial transformation. For example, an actuator may initiate at least partial transformation of a transient device by supplying energy (e.g., thermal, electromagnetic radiation, acoustic, RF energy, etc.) to an intermediate material or device component which affects the transformation, such as supplying energy to an encapsulating material, inorganic semiconductor components, or metallic conductor components. Thus, the actuator may comprise a single component or multiple components that alone or in combination facilitate transformation of the transient electronic device. In some embodiments, an actuator of the invention is directly or indirectly provided in communication with a transmitter, for example, via one or more receiver device components.

A "user initiated trigger signal" includes any action, other than the mere placement of a transient device in a particular environment, by which a person may start or initiate a programmable transformation of a transient device. Exemplary "user initiated trigger signals" include providing real-time user input data to the device or a transmitter in communication with the device (e.g., pressing a button, flipping a switch, setting a timer, etc.), providing at least one non-ambient external source of energy directly or indirectly to the device (e.g., an electric field, a magnetic field, acoustic energy, pressure, strain, heat, light, mechanical energy, etc.), and/or programming software to execute computer-readable instructions, which may be based on data received from the device, for example data from a feedback loop. In an embodiment, the user initiated external trigger signal is an electronic signal, an optical signal, a thermal signal, a magnetic signal, a mechanical signal, a chemical signal, an acoustic signal or an electrochemical signal. In an embodiment, the invention provides a transient electronic device configured to receive a user initiated trigger signal, for example, a user initiated trigger signal provided by a transmitter and received by a receiver component of the device.

A "non-ambient external source of energy" includes energy having a magnitude at least 10% greater, or at least 25% greater, or at least 50% greater than the magnitude of ubiquitous energy of the same form found in the environment in which a transient device is located.

The terms "directly and indirectly" describe the actions or physical positions of one component relative to another component. For example, a component that "directly" acts upon or touches another component does so without intervention from an intermediary. Contrarily, a component that "indirectly" acts upon or touches another component does so through an intermediary (e.g., a third component).

"Island" refers to a relatively rigid component of an electronic device comprising a plurality of semiconductor components. "Bridge" refers to structures interconnecting two or more islands or one island to another component. Specific bridge structures include semiconductor and metallic interconnects. In an embodiment, a transient device of the invention comprises one or more semiconductor-containing island structures, such as transistors, electrical circuits or integrated circuits, electrically connected via one or more bridge structures comprising electrical interconnects.

"Encapsulate" refers to the orientation of one structure such that it is at least partially, and in some cases completely, surrounded by one or more other structures, such as a substrate, adhesive layer or encapsulating layer. "Partially encapsulated" refers to the orientation of one structure such that it is partially surrounded by one or more other structures, for example, wherein 30%, or optionally 50%, or optionally 90%, of the external surface of the structure is surrounded by one or more structures. "Completely encapsulated" refers to the orientation of one structure such that it is completely surrounded by one or more other structures. The invention includes transient devices having partially or completely encapsulated inorganic semiconductor components, metallic conductor components and/or dielectric components, for example, via incorporation of a polymer encapsulant, such as a biopolymer, silk, a silk composite, or an elastomer encapsulant.

"Barrier layer" refers to a component spatially separating two or more other components or spatially separating a component from a structure, material, fluid or environment external to the device. In one embodiment, a barrier layer encapsulates one or more components. In some embodiments, a barrier layer separates one or more components from an aqueous solution, a biological tissue or both. The invention includes devices having one or more barrier layers, for example, one or more barrier layers positioned at the interface of the device with an external environment.

A barrier layer(s), and optionally a sacrificial layer on a substrate, may be etched to produce a "mesh structure", where at least a portion of the barrier layer(s), and optionally the sacrificial layer on a substrate, is removed. For example a portion of the barrier layer(s) disposed approximately 10 nanometers or more from an inorganic semiconductor component or additional component is removed. Removal of at least a portion of the barrier layer(s), and optionally the sacrificial layer on the substrate, may produce (i) one or more holes within the barrier layer(s) and/or (ii) electrical components, which are physically joined by a barrier layer(s) at a proximal end and physically separated at a distal end. In one embodiment, a mesh structure may be disposed upon a contiguous substrate, which provides structural support for the device during deployment into an environment.

"Contiguous" refers to materials or layers that are touching or connected throughout in an unbroken sequence. In one embodiment, a contiguous layer of an implantable biomedical device has not been etched to remove a substantial portion (e.g., 10% or more) of the originally provided material or layer.

"Active circuit" and "active circuitry" refer to one or more components configured for performing a specific function. Useful active circuits include, but are not limited to, amplifier circuits, multiplexing circuits, current limiting circuits, integrated circuits, transistors and transistor arrays. The present invention includes devices wherein the one or more inorganic semiconductor components, one or more metallic conductor components and/or one or more dielectric components comprise an active circuit or plurality of active circuits.

"Substrate" refers to a material, layer or other structure having a surface, such as a receiving surface, that is capable of supporting one or more components or devices. A component that is "bonded" to the substrate refers to a component that is in physical contact with the substrate and unable to substantially move relative to the substrate surface to which it is bonded. Unbonded components or portions of a component, in contrast, are capable of substantial movement relative to the substrate. In an embodiment, the invention provides devices wherein one or more inorganic semiconductor components, one or more metallic conductor components and/or one or more dielectric components are directly or indirectly bonded to the substrate, for example, via an adhesive layer or via an adhesion layer.

A "selectively transformable material" is a material that undergoes a physical change and/or a chemical change under pre-selected and/or predetermined conditions, such as conditions of time, pressure, temperature, chemical or biological composition, and/or electromagnetic radiation. Selectively transformable materials useful for some device applications undergo a physical transformation, such as a phase change including melting, sublimation, etc., optionally at a preselected time or at a preselected rate or in response to a preselected set of conditions or change in conditions. Selectively transformable materials useful for some device applications undergo a chemical transformation, such as decomposition, disintegration, dissolution, hydrolysis, resorption, bioresorption, photodecomposition, depolymerization, etching, or corrosion, optionally at a preselected time or at a preselected rate or in response to a preselected set of conditions or change in conditions. The pre-selected condition(s) may occur naturally, for example, provided by conditions of a device environment (e.g., ambient temperature, pressure, chemical or biological environment, natural electromagnetic radiation, etc.) or may occur via artificial condition(s) provided to, or within, a transient electronic device, such as a user or device initiated temperature, pressure, chemical or biological environment, electromagnetic radiation, magnetic conditions, mechanical strain, or electronic conditions. When the selectively transformable material of a transient electronic device is exposed to the condition(s) that initiate transformation of the material, the selectively transformable material may be substantially completely or completely transformed at a "pre-selected time" or a "pre-selected rate". Devices of the invention include selectively transformable materials that undergo a complete transformation, substantially complete transformation or an incomplete transformation. A selectively transformable material that is "substantially completely" transformed is 95% transformed, or 98% transformed, or 99% transformed, or 99.9% transformed, or 99.99% transformed, but not completely (i.e., 100%) transformed. In some embodiments, a selectively transformable material undergoes a chemical change resulting in a change in a physical, chemical, electronic or optoelectronic property, optionally at a pre-selected time or at a pre-selected rate. In an embodiment, for example, a selectively transformable material undergoes a chemical or physical change resulting in a change of a first composition characterized by a conducting or semiconducting material to a second composition characterized as an insulator. In some embodiments, a selectively transformable material is a selectively removable material.

A "selectively removable material" is a material that is physically and/or chemically removed under pre-selected or predetermined conditions such as conditions of time, pressure, temperature, chemical or biological composition, and/or electromagnetic radiation. In an embodiment, for example, a selectively removable material is removed via a process selected from the group consisting of decomposition, disintegration, dissolution, hydrolysis, resorption, bioresorption, photodecomposition, and depolymerization, optionally at a preselected time or at a preselected rate or in response to a preselected set of conditions or change in conditions. In an embodiment, for example, a selectively removable material is removed by undergoing a phase change, such as melting or sublimation, resulting in loss or relocation of the material, optionally at a preselected time or at a preselected rate or in response to a preselected set of conditions or change in conditions. The pre-selected condition(s) may occur naturally, for example, provided by conditions of a device environment (e.g., ambient temperature, pressure, chemical or biological environment, natural electromagnetic radiation, etc.) or may occur via artificial condition(s) provided to, or within, a transient electronic device, such as a user or device initiated temperature, pressure, chemical or biological environment, electromagnetic radiation, electronic conditions. When the selectively removable material of a transient electronic device is exposed to the condition(s) that initiate removal of the material, the selectively removable material may be substantially completely removed, completely removed or incompletely removed at a "pre-selected time" or a "pre-selected rate". A selectively removable material that is "substantially completely" removed is 95% removed, or 98% removed, or 99% removed, or 99.9% removed, or 99.99% removed, but not completely (i.e., 100%) removed.

A "pre-selected time" refers to an elapsed time from an initial time, $t_0$. For example, a pre-selected time may refer to an elapsed time from a component/device fabrication or deployment, to a critical time, $t_c$, for example, when the thickness of a selectively removable material exposed to a pre-selected condition(s) reaches zero, or substantially zero (10% or less of initial thickness, 5% or less of initial thickness, 1% or less of initial thickness) or when a property (e.g. conductance or resistivity) of a selectively removable material reaches a threshold value; e.g., a decrease in conductivity equal to 50%, optionally for some applications 80%, and optionally for some applications 95% or alternatively when conductivity equals 0. In an embodiment, the preselected time may be calculated according to:

$$t_c = \frac{4\rho_m M(H_2O)}{kw_0 M(m)} \frac{\sqrt{\frac{kh_0^2}{D}}}{\tanh\sqrt{\frac{kh_0^2}{D}}};$$

where $t_c$ is the critical time, $\rho_m$ is the mass density of the material, $M(H_2O)$ is the molar mass of water, $M(m)$ is the molar mass of the material, $h_0$ is the initial thickness of the material, $D$ is the diffusivity of water, $k$ is the reaction constant for the dissolution reaction, and $w_0$ is the initial concentration of water.

A "pre-selected rate" refers to an amount of selectively removable material removed from a device or component per unit time. The pre-selected rate may be reported as an average rate (over the lifetime of the device or component) or an instantaneous rate. When a rate type is not specified, an average rate is assumed.

A "programmable transformation" refers to a pre-selected or predetermined physical, chemical and/or electrical change within a transient electronic device that provides a change of the function of the device from a first condition to a second condition. A programmable transformation may be pre-set at the time of component/device fabrication or deployment or a real-time triggered programmable transformation controlled by a transmitter that provides a signal received by the device.

A "transience profile" describes a change in physical parameters or properties (e.g., thickness, conductivity, resistance, mass, porosity, etc.) of a material as a function of time, e.g., thickness gained/lost over time. A transience profile may be characterized by a rate, for example, the rate of change of the physical dimensions (e.g., thickness) or physical properties (e.g., mass, conductivity, porosity, resistance, etc.) of a selectively transformable material. The invention includes selectively transformable materials having a transience profile characterized by a rate of change of the physical dimensions (e.g., thickness) or physical properties (e.g., mass, conductivity, etc.) that is constant or varies as a function of time.

"Degradable" refers to material that is susceptible to being chemically and/or physically broken down into smaller segments. Degradable materials may, for example, be decomposed, resorbed, dissolved, absorbed, corroded, de-polymerized and/or disintegrated. In some embodiments, the invention provides degradable devices.

"Bioresorbable" refers to a material that is susceptible to being chemically broken down into lower molecular weight chemical moieties by reagents that are naturally present in a biological environment. In an in-vivo application, the chemical moieties may be assimilated into human or animal tissue. A bioresorbable material that is "substantially completely" resorbed is highly resorbed (e.g., 95% resorbed, or 98% resorbed, or 99% resorbed, or 99.9% resorbed, or 99.99% resorbed), but not completely (i.e., 100%) resorbed. In some embodiments, the invention provides bioresorbable devices.

"Biocompatible" refers to a material that does not elicit an immunological rejection or detrimental effect when it is disposed within an in-vivo biological environment. For example, a biological marker indicative of an immune response changes less than 10%, or less than 20%, or less than 25%, or less than 40%, or less than 50% from a baseline value when a biocompatible material is implanted into a human or animal. In some embodiments, the invention provides biocompatible devices.

"Bioinert" refers to a material that does not elicit an immune response from a human or animal when it is disposed within an in-vivo biological environment. For example, a biological marker indicative of an immune response remains substantially constant (plus or minus 5% of a baseline value) when a bioinert material is implanted into a human or animal. In some embodiments, the invention provides bioinert devices.

"Ecocompatible" refers to a material that is environmentally benign in that it may be degraded or decomposed into one or more compounds that occur naturally in the environment. In some embodiments, the invention provides ecocompatible devices.

"Nanostructured material" and "microstructured material" refer to materials having one or more nanometer-sized and micrometer-sized, respectively, physical dimensions (e.g., thickness) or features such as recessed or relief features, such as one or more nanometer-sized and micrometer-sized channels, voids, pores, pillars, etc. The relief features or recessed features of a nanostructured material have at least one physical dimension selected from the range of 1-1000 nm, while the relief features or recessed features of a microstructured material have at least one physical dimension selected from the range of 1-1000 µm. Nanostructured and microstructured materials include, for example, thin films (e.g., microfilms and nanofilms), porous materials, patterns of recessed features, patterns of relief features, materials having abrasive or rough surfaces, and the like. A nanofilm structure is also an example of a nanostructured material and a microfilm structure is an example of a microstructured material. In an embodiment, the invention provides devices comprising one or more nanostructured or microstructured inorganic semiconductor components, one or more nanostructured or microstructured metallic conductor components, one or more nanostructured or microstructured dielectric components, one or more nanostructured or microstructured encapsulating layers and/or one or more nanostructured or microstructured substrate layers.

A "nanomembrane" is a structure having a thickness selected from the range of 1-1000 nm or alternatively for some applications a thickness selected from the range of 1-100 nm, for example provided in the form of a ribbon, cylinder or platelet. In some embodiments, a nanoribbon is a semiconductor, dielectric or metallic conductor structure of an electronic device. In some embodiments, a nanoribbon has a thickness less than 1000 nm and optionally less than 100 nm. In some embodiments, a nanoribbon has a ratio of thickness to a lateral dimension (e.g., length or width) selected from the range of 0.1 to 0.0001.

"Dielectric" refers to a non-conducting or insulating material. In an embodiment, an inorganic dielectric comprises a dielectric material substantially free of carbon. Specific examples of inorganic dielectric materials include, but are not limited to, silicon nitride, silicon dioxide, silk, silk composite, elastomers and polymers.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomeric stamp" and "elastomeric transfer device" are used interchangeably and refer to an elastomeric material having a surface that can receive as well as transfer a material. Exemplary conformal transfer devices useful in some methods of the invention include elastomeric transfer devices such as elastomeric stamps, molds and masks. The transfer device affects and/or facilitates material transfer from a donor material to a receiver material. In an embodiment, a method of the invention uses a conformal transfer device, such as an elastomeric transfer device (e.g. elastomeric stamp) in a microtransfer printing process, for example, to transfer one or more single crystalline inorganic semiconductor structures, one or more dielectric structures and/or one or more metallic conductor structures from a fabrication substrate to a device substrate.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. In some embodiments, an elastomeric stamp comprises an elastomer. Exemplary elastomers include, but are not limited to silicon containing polymers such as polysiloxanes including poly(dimethyl siloxane) (i.e. PDMS and h-PDMS), poly(methyl siloxane), partially alkylated poly(methyl siloxane), poly(alkyl methyl siloxane) and poly(phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt any desired contour profile, for example a contour profile allowing for conformal contact with a surface having a pattern of relief features. In certain embodiments, a desired contour profile is that of a tissue in a biological environment.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface. In an embodiment, a method of the invention comprises establishing conformal contact between a conformal transfer device and one or more single crystalline inorganic semiconductor structures, one or more dielectric structures and/or one or more metallic conductor structures, for example, in a microtransfer printing process, such as dry transfer contact printing.

"Young's modulus" is a mechanical property of a material, device or layer which refers to the ratio of stress to strain for a given substance. Young's modulus may be provided by the expression:

$$E = \frac{(\text{stress})}{(\text{strain})} = \left(\frac{L_0}{\Delta L}\right)\left(\frac{F}{A}\right), \quad (I)$$

where $E$ is Young's modulus, $L_0$ is the equilibrium length, $\Delta L$ is the length change under the applied stress, $F$ is the force applied, and $A$ is the area over which the force is applied. Young's modulus may also be expressed in terms of Lame constants via the equation:

$$E = \frac{\mu(3\lambda + 2\mu)}{\lambda + \mu}, \quad (II)$$

where $\lambda$ and $\mu$ are Lame constants. High Young's modulus (or "high modulus") and low Young's modulus (or "low modulus") are relative descriptors of the magnitude of Young's modulus in a given material, layer or device. In some embodiments, a high Young's modulus is larger than a low Young's modulus, preferably about 10 times larger for some applications, more preferably about 100 times larger for other applications, and even more preferably about 1000 times larger for yet other applications. In an embodiment, a low modulus layer has a Young's modulus less than 100 MPa, optionally less than 10 MPa, and optionally a Young's modulus selected from the range of 0.1 MPa to 50 MPa. In an embodiment, a high modulus layer has a Young's modulus greater than 100 MPa, optionally greater than 10 GPa, and optionally a Young's modulus selected from the range of 1 GPa to 100 GPa. In an embodiment, a device of the invention has one or more components, such as substrate, encapsulating layer, inorganic semiconductor structures, dielectric structures and/or metallic conductor structures, having a low Young's modulus. In an embodiment, a device of the invention has an overall low Young's modulus.

"Inhomogeneous Young's modulus" refers to a material having a Young's modulus that spatially varies (e.g., changes with surface location). A material having an inhomogeneous Young's modulus may optionally be described in terms of a "bulk" or "average" Young's modulus for the entire material.

"Low modulus" refers to materials having a Young's modulus less than or equal to 10 MPa, less than or equal to 5 MPa or less than or equal to 1 MPa.

"Bending stiffness" is a mechanical property of a material, device or layer describing the resistance of the material, device or layer to an applied bending moment. Generally, bending stiffness is defined as the product of the modulus and area moment of inertia of the material, device or layer. A material having an inhomogeneous bending stiffness may optionally be described in terms of a "bulk" or "average" bending stiffness for the entire layer of material.

Transient devices and methods of making and using the devices will now be described with reference to the figures. For clarity, multiple items within a figure may not be labeled and the figures may not be drawn to scale.

Figure 1B:
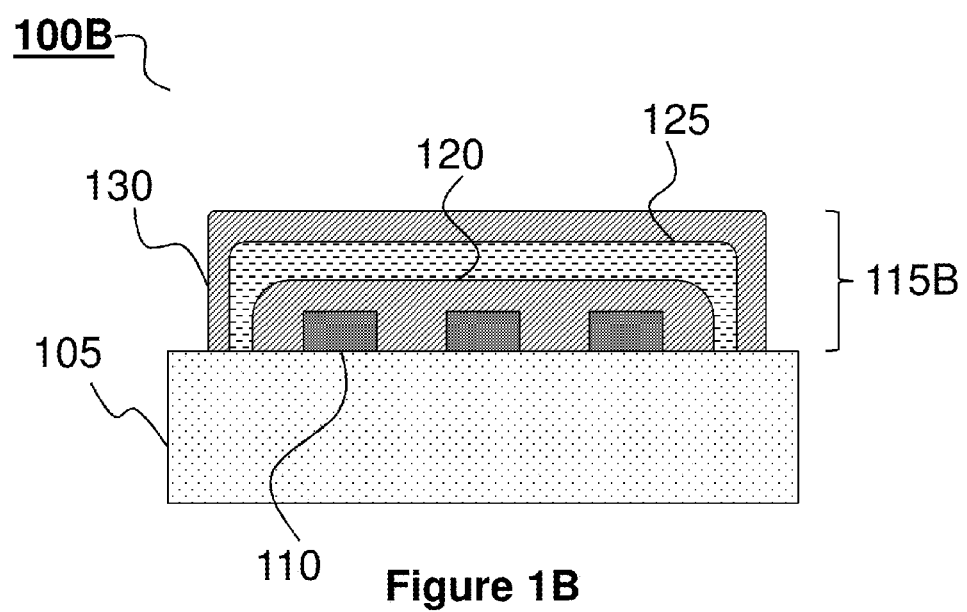
Figure 1C:
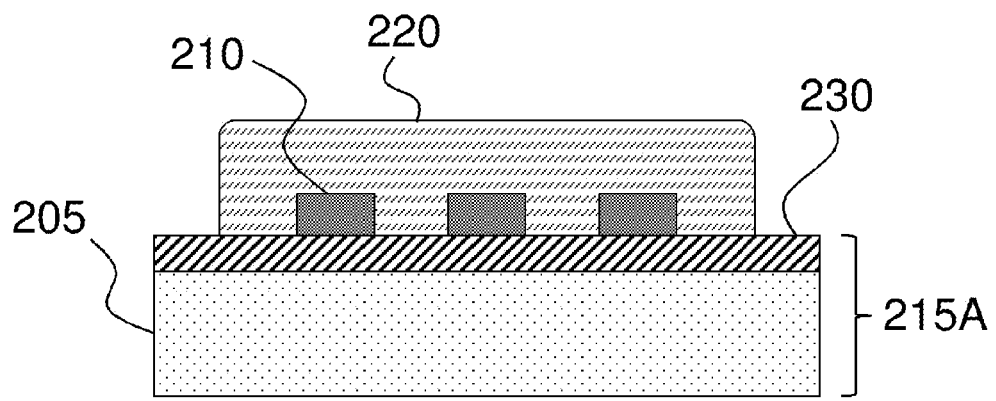
Figure 1D:
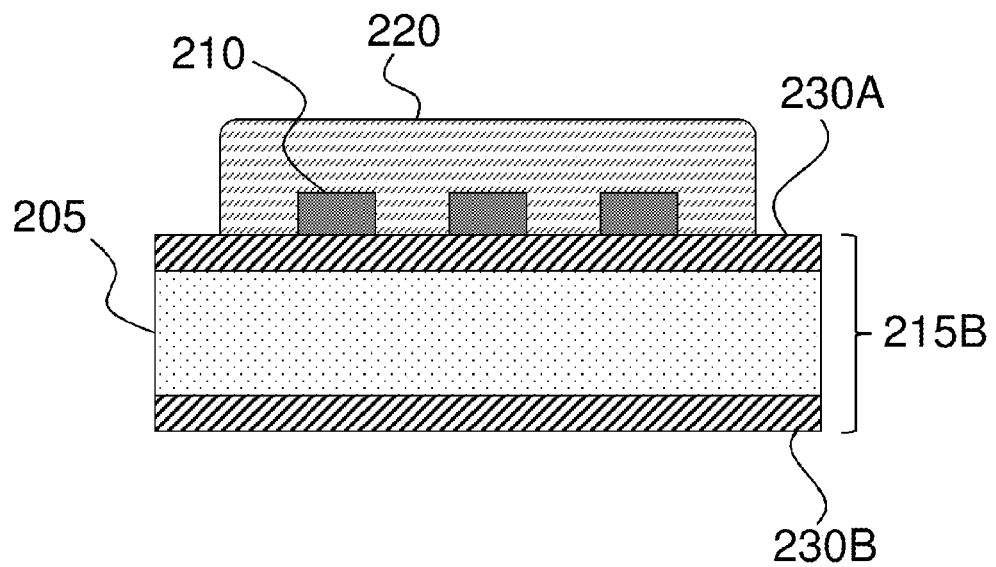

FIGS. 1A-1D provide schematic diagrams illustrating side views of transient electronic devices of the invention. FIGS. 1A and 1B are directed to transient electronic devices having a multilayer encapsulant layer comprising a selectively removable inorganic material in combination with a barrier layer or electrically insulating layer. FIGS. 1C and 1D are directed to a transient electronic device having a multilayer substrate comprising a selectively removable inorganic material in combination with a barrier layer or electrically insulating layer.

In FIG. 1A, transient electronic device 100A comprises substrate 105 supporting, directly or indirectly, one or more inorganic semiconductor components, one or more metallic conductor components or one or more inorganic semiconductor components and one or more metallic conductor components 110, which in some embodiments comprise semiconductor devices or semiconductor device components. Encapsulant layer 0115A is provided so as to completely or partially encapsulate the inorganic semiconductor components and/or metallic conductor components 110, for example by encapsulating at least 20%, 50%, 70% or 90% of the area or volume of the inorganic semiconductor components and/or metallic conductor components 110. As shown in FIG. 1A, encapsulant layer 115A is a multilayer structure comprising an interior layer 120, comprising a barrier layer or electrically insulating layer, and an exterior layer 125 comprising a selectively removable inorganic material, such as an inorganic thin film, foil or coating. In an embodiment, for example, interior layer 120 is an electrically insulating layer preventing electrical contact between exterior layer comprising a selectively removable inorganic material 125 and the underlying inorganic semiconductor components and/or metallic conductor components 110. In an embodiment, for example, exterior layer 125 comprises a metal foil or metal oxide layer having a preselected transience profile, wherein at least partial removal of the exterior layer 125 in response to an external or internal stimulus at least partially exposes the inorganic semiconductor components and/or metallic conductor components 110, for example, to the internal or external stimulus and/or to an external environment.

In FIG. 1B, transient electronic device 100B comprises substrate 105 supporting, directly or indirectly, one or more inorganic semiconductor components, one or more metallic conductor components or one or more inorganic semiconductor components and one or more metallic conductor components 110, which in some embodiments comprise semiconductor devices or semiconductor device components. Encapsulant layer 115B is provided so as to completely or partially encapsulate the inorganic semiconductor components and/or metallic conductor components 110, for example by encapsulating at least 20%, 50%, 70% or 90% of the area or volume of the inorganic semiconductor components and/or metallic conductor components 110. As shown in FIG. 1B, encapsulant layer 115B is a multilayer structure comprising an interior layer 120 comprising a barrier layer or electrically insulating layer, and an intermediate layer 125 comprising a selectively removable inorganic material, such as an inorganic thin film, foil or coating and an exterior layer 130 comprising a barrier layer or electrically insulating layer. In an embodiment, for example, interior layer 120 is an electrically insulating layer preventing electrical contact between intermediate layer comprising a selectively removable inorganic material 125 and the underlying inorganic semiconductor components and/or metallic conductor components 110. In an embodiment, for example, exterior layer 130 is a barrier layer substantially impermeable to an external composition, such as an external solvent (e.g., water, biofluid, etc.). In an embodiment, for example, intermediate layer 125 comprises a metal foil or metal oxide layer having a preselected transience profile, wherein at least partial removal of the intermediate layer 125 and interior layer 120 in response to an external or internal stimulus at least partially exposes the inorganic semiconductor components and/or metallic conductor components 110, for example, to the internal or external stimulus and/or to an external environment.

In FIG. 1C, transient electronic device 200A comprises substrate 215A supporting, directly or indirectly, one or more inorganic semiconductor components, one or more metallic conductor components or one or more inorganic semiconductor components and one or more metallic conductor components 210, which in some embodiments comprise semiconductor devices or semiconductor device components. Encapsulant layer 220 is provided so as to completely or partially encapsulate the inorganic semiconductor components and/or metallic conductor components 210, for example by encapsulating at least 20%, 50%, 70% or 90% of the area or volume of the inorganic semiconductor components and/or metallic conductor components 210. As shown in FIG. 1C, substrate 215A is a multilayer structure comprising an interior layer 230, comprising a barrier layer or electrically insulating layer, and an exterior layer 205 comprising a selectively removable inorganic material, such as an inorganic thin film, foil or coating. In an embodiment, for example, interior layer 230 is an electrically insulating layer preventing electrical contact between exterior layer comprising a selectively removable inorganic material 205 and the inorganic semiconductor components and/or metallic conductor components 210. In an embodiment, for example, exterior layer 205 comprises a metal foil or metal oxide layer having a preselected transience profile, wherein at least partial removal of the exterior layer 205 in response to an external or internal stimulus at least partially exposes the inorganic semiconductor components and/or metallic conductor components 210, for example, to the internal or external stimulus and/or to an external environment.

In FIG. 1D, transient electronic device 200B comprises substrate 215B supporting, directly or indirectly, one or more inorganic semiconductor components, one or more metallic conductor components or one or more inorganic semiconductor components and one or more metallic conductor components 210, which in some embodiments comprise semiconductor devices or semiconductor device components. Encapsulant layer 220 is provided so as to completely or partially encapsulate the inorganic semiconductor components and/or metallic conductor components 210, for example by encapsulating at least 20%, 50%, 70% or 90% of the area or volume of the inorganic semiconductor components and/or metallic conductor components 210. As shown in FIG. 1D, substrate 215B is a multilayer structure comprising an interior layer 230A comprising a barrier layer or electrically insulating layer, and an intermediate layer 205 comprising a selectively removable inorganic material, such as an inorganic thin film, foil or coating and an exterior layer 230B comprising a barrier layer or electrically insulating layer. In an embodiment, for example, interior layer 230A is an electrically insulating layer preventing electrical contact between intermediate layer comprising a selectively removable inorganic material 205 and the inorganic semiconductor components and/or metallic conductor components 210. In an embodiment, for example, exterior layer 230B is a barrier layer substantially impermeable to an external composition, such as an external solvent (e.g., water, biofluid, etc.). In an embodiment, for example, intermediate layer 205 comprises a metal foil or metal oxide layer having a preselected transience profile, wherein at least partial removal of the intermediate layer 205 and interior layer 230A in response to an external or internal stimulus at least partially exposes the inorganic semiconductor components and/or metallic conductor components 210, for example, to the internal or external stimulus and/or to an external environment.

EXAMPLE 1

Inorganic Substrates and Encapsulation Layers for Transient Electronics

Background and Motivation

This example demonstrates a new class silicon-based electronic devices that are physically transient, for example, in the sense that they dissolve or otherwise transform at controlled rates when exposed to water in the environment or the body[1]. In some embodiments, these systems comprise transient materials, such as magnesium for metal electrodes and interconnects, MgO and/or $SiO_2$ for gate and interlayer dielectrics, and single crystal silicon nanomembranes (Si NMs) for semiconductors. In all cases, extensive engineering studies of the key properties, including dissolution mechanisms[2], for each material are important for device engineering. On-going research indicates the ability to enhance/control the dissolution rates of transient components via control over the morphology and chemical compositions of the various functional layers. Additionally, the properties of the aqueous environments can have a strong influence. Initial experiments on Si NMs, for example, reveal the dependence of dissolution rates on various aqueous environments, such as blood, sea water, serum, tap water, and simulated body solution with different pH levels. Similar studies on various candidates for the conductive layers, for instance, Mg alloy (AZ31 B), iron (Fe), molybdenum (Mo), tungsten (W) and zinc (Zn), establish their utility and range of uses.

Besides these functional layers, encapsulation and substrate materials play important roles in these systems because their transient characteristics may also define the operational lifetimes. Silk, other biomaterials and synthetic polymers are of strong interest, but their inability to serve as completely impermeable water barriers, without dimensional change associated with swelling, represent daunting technical challenges. Inorganic materials may provide compelling alternatives. A natural, attractive candidate as an encapsulant and/or component of a layered substrate construct is $SiO_2$ deposited using various conditions in PECVD to control density and, therefore, dissolution rate. Another promising related possibility is spin-on-glass (SOG), due to its solution processability and excellent planarization properties. Metal foils have potential as mechanically tough, rugged but flexible substrates. This example describes use of these materials as substrates and encapsulation layers.

The present example highlights the significance of establishing (a) dissolution rates for various inorganic materials relevant to encapsulation layers and substrates for transient electronic systems, and (b) demonstration vehicles for the use of these materials in electronic devices with practical ranges of transience times. The present example describes (1) the study of the kinetics of dissolution for silicon, silicon oxide, spin-on-glass, and metals in various solutions, (2) design and demonstration of an inorganic-based substrate system and encapsulation strategy using these materials, and (3) integration of simple transient electronic components (resistors, inductors, transistors) onto these substrates, with encapsulation, to demonstrate function.

Dissolution Rates for Inorganic Materials as Substrates and Encapsulation Layers Deposited and Grown layers of Silicon Dioxide ($SiO_2$)

Figure 2:
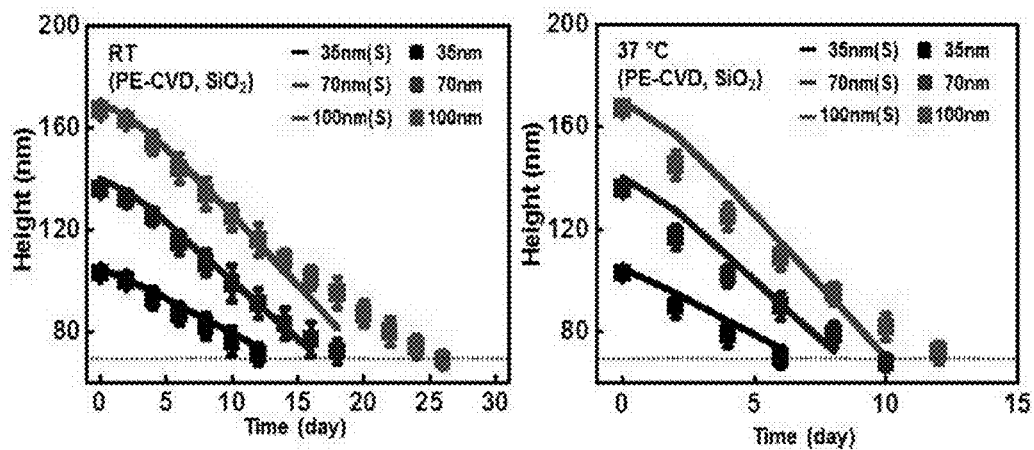
FIG. 2. Time dependent change in the thicknesses of thin layers of PECVD $SiO_2$ in PBS at room temperature and 37° C.
Figure 3:
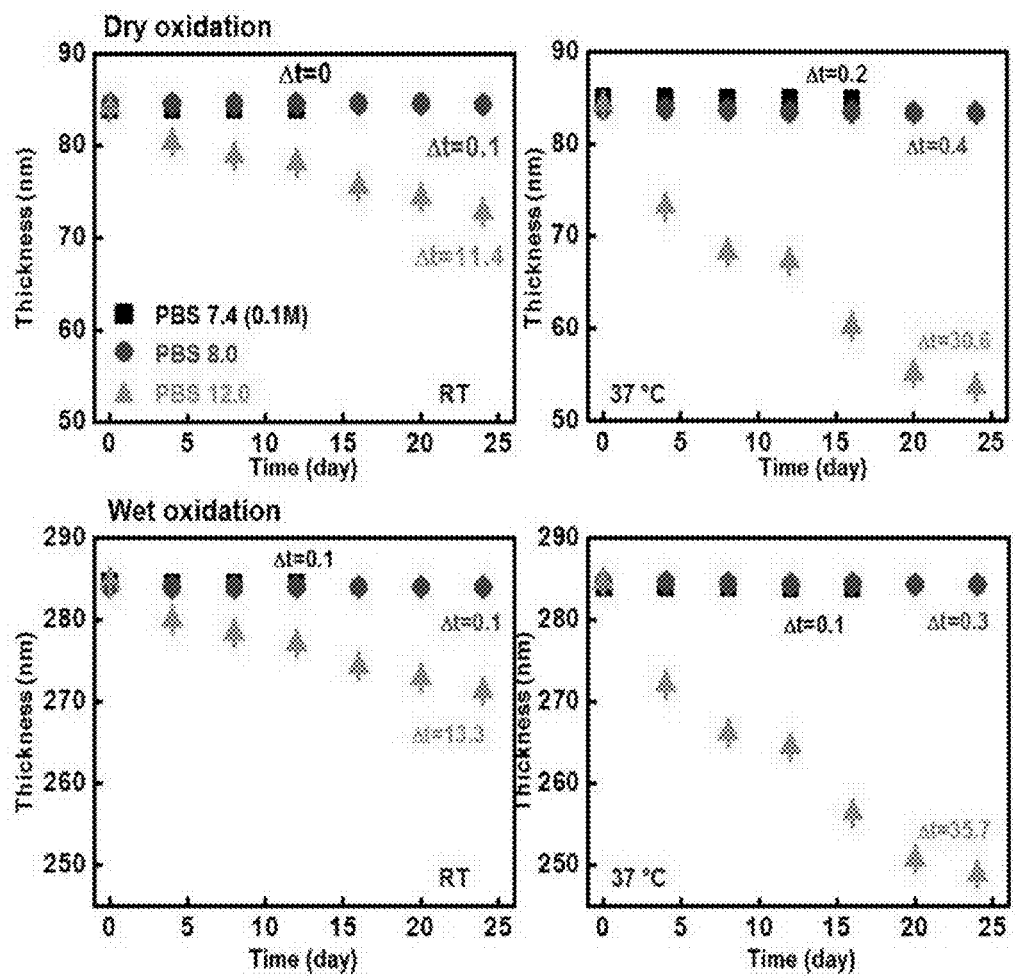
FIG. 3. Time dependent change in the thicknesses of thin layers of thermally grown $SiO_2$ (wet and dry oxidation) at different pH in PBS solutions at room temperature, and 37° C.

Silicon dioxide ($SiO_2$) serves as an example material option for the gate and interlayer dielectrics of previously reported transient electronic devices [1]. An ability to control the rate of dissolution in this material, and to exploit it in substrates and encapsulation layers forms a focus of this example. FIG. 2 shows that a thin film of $SiO_2$ deposited by plasma enhanced chemical vapor deposition (PECVD) dissolves in PBS solution at room temperature and physiological temperature, respectively, over the course of weeks. The chemical mechanisms here are related to those of single crystalline silicon, i.e. silicon oxide reacts water via hydrolysis to form silicic acid ($Si(OH)_4$). A key recent finding is that the dissolution rates depend strongly on deposition conditions. This example explores the dissolution of PECVD $SiO_2$ formed at various temperatures between 200 and 500° C., as well as wet and dry thermally grown oxides (1100° C.; data in FIG. 3). Preliminary findings show that thermal oxide has extremely slow dissolution compared to low temperature PECVD material. These two examples bracket a broad range of transience times that can be accessed in this single material system, thereby highlighting its potential value as an encapsulation layer, or as a component of a layered substrate construct (see, below).

Bulk Foils and Thin Film Coatings of Metals (Mg, Mg alloy, Fe, W and Zn)

Conductive materials are essential for electrodes and interconnects in transient electronics. This example shows, however, that conductive materials, for example in the form of foils or coatings, also provide an important class of materials for substrates and/or encapsulation layers when combined with insulating layers to avoid unwanted electrical effects. Systematic fundamental studies of dissolution kinetics of various metals, both as bulk foils and thin film coatings, in biological environments provide important guidelines on selecting metals for these purposes. Six metals are of interest: magnesium (Mg), magnesium alloy (AZ31 B with 3 wt % aluminum and 1wt % zinc), tungsten (W), molybdenum (Mo), zinc (Zn) and iron (Fe). Preliminary dissolution measurements in de-ionized (DI) water and simulated bio-fluid (Hank's solution, pH 7.4) at room temperature appear in FIG. 4. Here, films with thicknesses of 150 nm or 300 nm were formed by electron beam (E-beam) evaporation (Fe, Mo) or magnetron sputtering (Mg, Mg alloys, Zn and W). In general, W and Fe exhibit much slower degradation rates (~ few days) compared to Mg, Mg alloys and Zn (<few hours) due to the non-protective nature of their hydrolysis products, namely magnesium oxide and zinc oxide respectively. Resistance changes in Fe appear very gradually, due to the formation of a relatively protective iron oxide layer. Compared to sputtered W films, CVD W possesses a much lower resistivity and slower dissolution rate in DI water, making it ideal for long term transience. A reactive diffusion model can capture the trends for Mg, Mg alloys, Zn and W (solid lines in FIG. 4), thereby providing the ability to predict transience times as a function of thin film thickness, pH, and other parameters. Based on these results, metals combined with suitably processed $SiO_2$ enable the degradation times that span a desired range, from minutes to months, and possibly longer. In the form of foils and layered assemblies, these materials are attractive as flexible substrates, as described next.

Inorganic Substrate Structures for Transient Electronics

Figure 5:
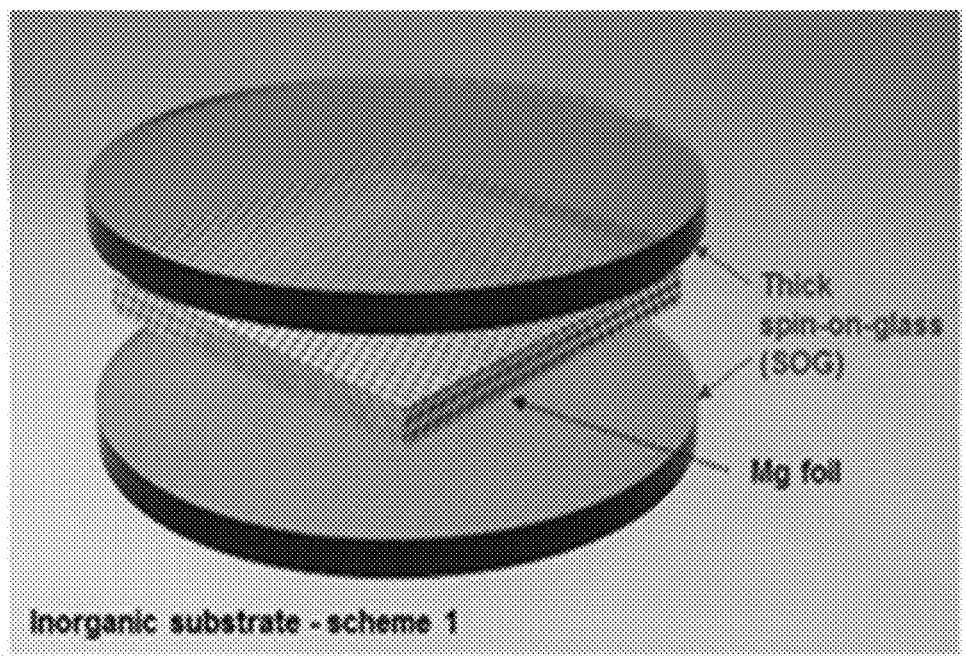
FIG. 5. The schematic illustration of inorganic layered substrate structure, using metal foils coated with spin-on-glass (SOG).
Figure 6A:
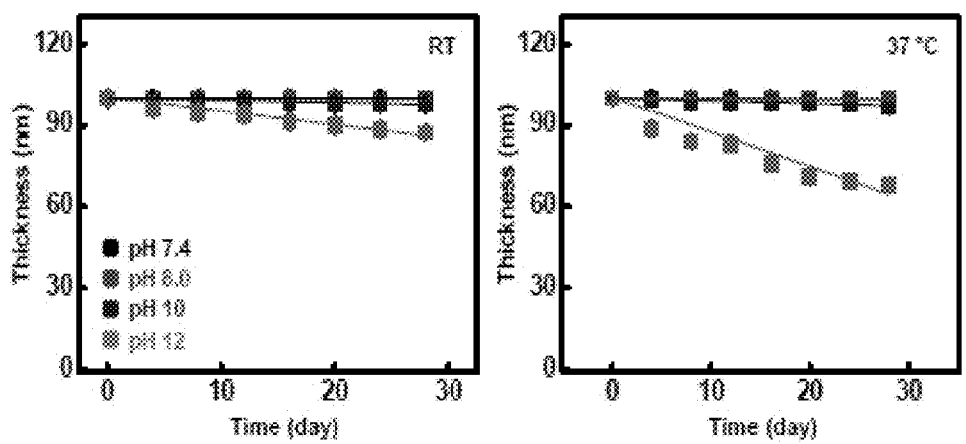
FIG. 6A-6C. Dissolution kinetics of $SiO_2$ in aqueous solution at different pH and temperature (1) FIG. 6A $SiO_2$ thermally grown by dry or wet oxidation, (2) FIG. 6B $SiO_2$ deposited by plasma enhanced chemical vapor deposition and (3) FIG. 6C $SiO_2$ deposited by electron beam evaporation. Calculated (lines) and experimental (symbols) dissolution rates of silicon oxides in buffer solution at different pH (black, pH 7.4; red, pH 8; blue, pH 10; magenta, pH 12) at room (left) and physiological (right, 37° C.) temperature. The thickness was measured by spectroscopic ellipsometry.
Figure 6A:
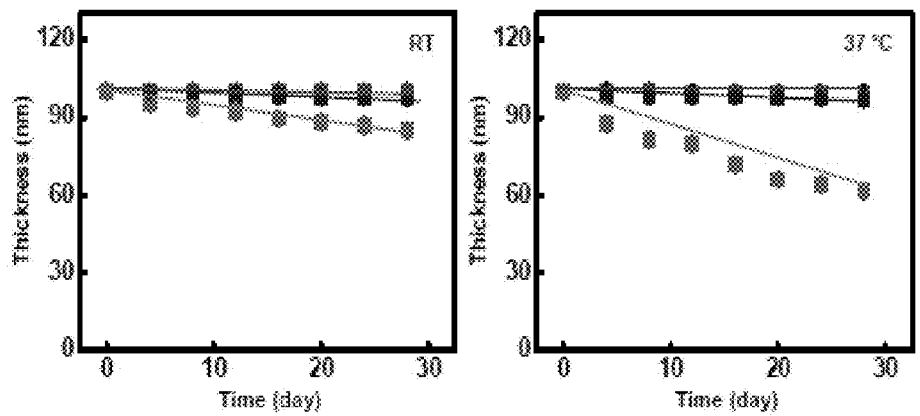
Figure 6B:
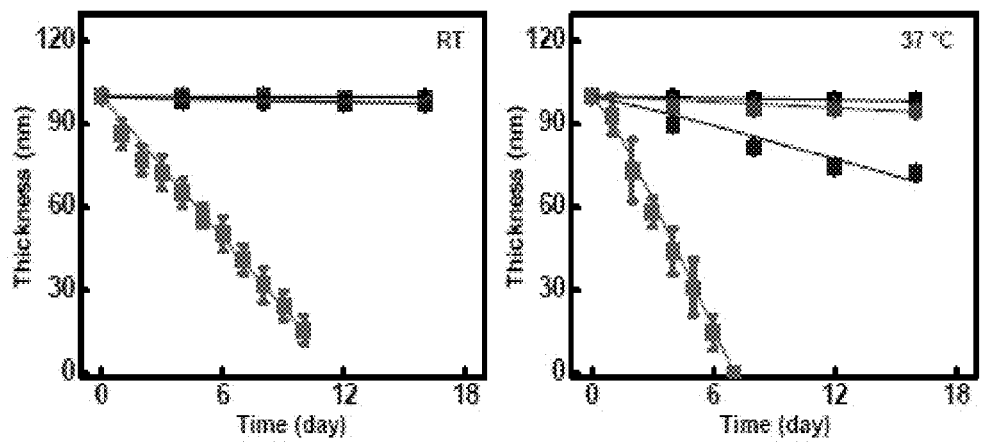
Figure 6C:
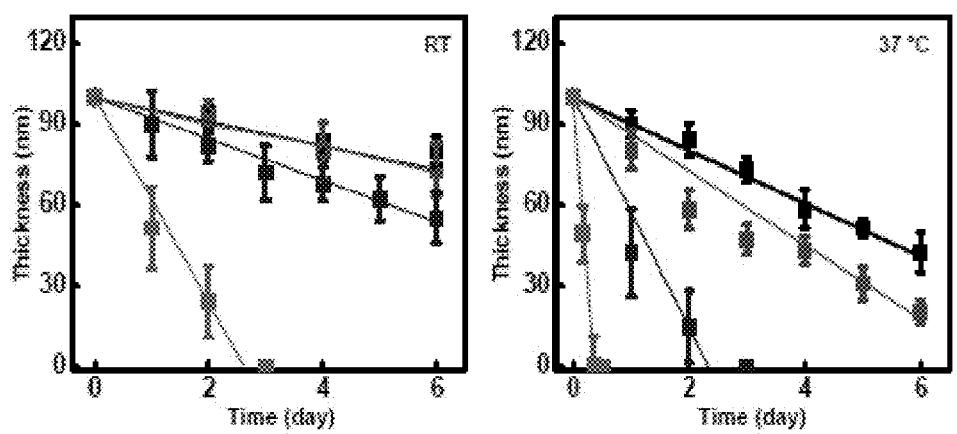

Inorganic substrates based on coated metal foils could represent an attractive alternative to silk-based biopolymers, or synthetic polymers. A schematic illustration of one possibility appears in FIG. 5. The structure simply utilizes a metal foil (e.g. Mg foil, 5-10 μm thick) as a supporting material with films of spin cast SOG as electrically insulating layers and water barriers on top and bottom. The foil imparts a level of mechanical robustness that is not present in the SOG films alone. Additional layers of PECVD $SiO_2$ and/or metals can be added to the structure to enhance the barrier properties and to minimize probability for electrical leakage pathways, thereby offering the possibility to extend the transience times. A variety of combinations of layered structures based on the materials described in the previous section creates a rich design space.

Demonstration Vehicles for Transient Electronics Based on Inorganic Substrates and Encapsulants To evaluate practical performance of encapsulants and substrate structures outlined in the previous sections, test vehicles ranging from serpentine resistors and inductors to Si NM transistors may be built. Electrical evaluation of these components may be performed as a function of time for complete immersion in DI water and PBS at physiological conditions. The kinetics associated with transience in function may be studied, and correlated to the choice of materials and layered structures.

REFERENCE

1. S.-W. Hwang, H. Tao, D.-H. Kim, H. Cheng, J.-K. Song, E. Rill, M. A. Brenckle, B. Panilaitis, S. M. Won, Y.-S. Kim, Y. M. Song, K. J. Yu, A. Ameen, R. Li, Y. Su, M. Yang, D. L. Kaplan, M. R. Zakin, M. J. Slepian, Y. Huang, F. G. Omenetto and J. A. Rogers, "A Physically Transient Form of Silicon Electronics," *Science* 337, 1640-1644 (2012).
2. R. Li, H. Cheng, Y. Su, S.-W. Hwang, L. Yin, H. Tao, M. A. Brenckle, D.-H. Kim, F. G. Omenetto, J. A. Rogers and Y. Huang, "An Analytical Model of Reactive Diffusion for Transient Electronics," *Advanced Functional Materials*, ASAP (2013). DOI: 10.1002/adfm.201203088

EXAMPLE 2

Inorganic Substrates and Encapsulation Layers for Transient Electronics

FIG. 6 shows dissolution kinetics of $SiO_2$ in aqueous solution at different pH and temperature (1) $SiO_2$ thermally grown by dry or wet oxidation, (2) $SiO_2$ deposited by plasma enhanced chemical vapor deposition and (3) $SiO_2$ deposited by electron beam evaporation. Calculated (lines) and experimental (symbols) dissolution rates of silicon oxides in buffer solution at different pH (black, pH 7.4; red, pH 8; blue, pH 10; magenta, pH 12) at room (left) and physiological (right, 37° C.) temperature. The thickness was measured by spectroscopic ellipsometry. There was no difference is dissolution rates between thermally grown $SiO_2$ grown by the dry or wet oxidation method.

Figure 7A:
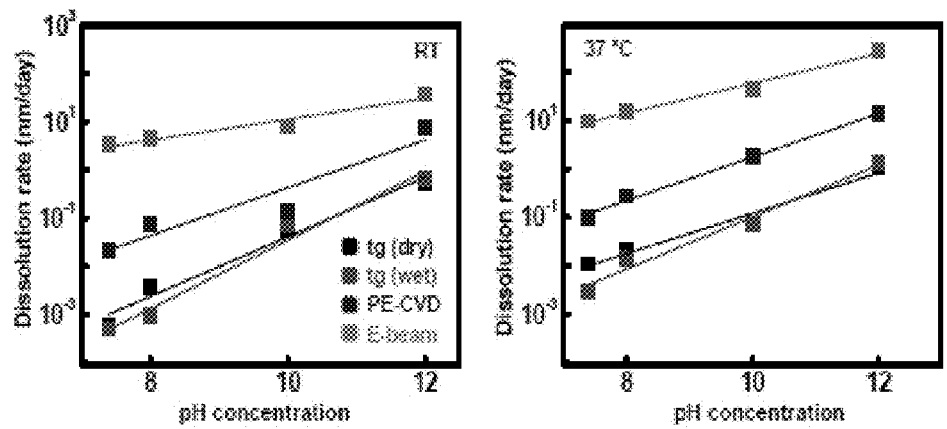
FIG. 7A-7B.

FIG. 7A shows measured data (symbols) and numerical fits (lines) for pH-dependent dissolution kinetics of oxides (black, tg-oxide by dry oxidation; red, tg-oxide by wet oxidation; blue, PECVD oxide; magenta, E-beam oxide) at room temperature and 37° C. Higher pH concentration increases the possibility of reaction between Si—O and $OH^-$, and therefore increases the dissolution rate. Quartz and amorphous silica showed the same trend in the literature.[1]

Figure 7B:
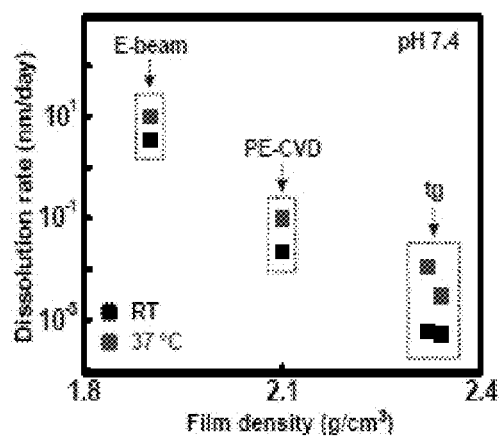

FIG. 7B shows $SiO_2$ film property dependency exhibited as film density versus dissolution rate. Low density films have more chances to meet reaction species, which increases dissolution rate. Low density films also have fewer atoms per layer, which causes the dissolution rate in terms of thickness to decrease faster.

Figure 8:
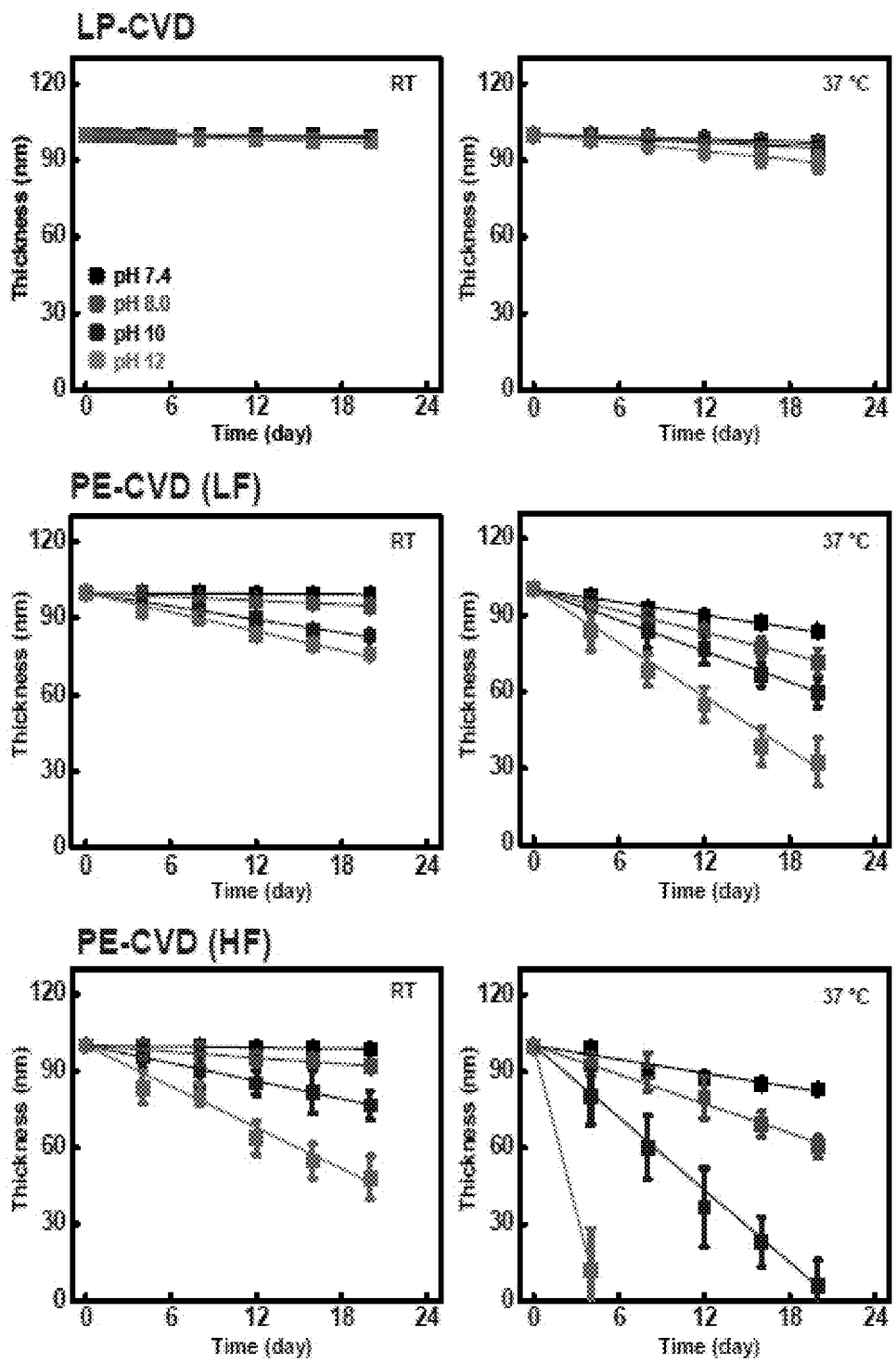
FIG. 8. Experimental results for dissolution study of $SiN_X$. The plots provide measurements of thickness (nm) as a function of time (days).

FIG. 8 shows a dissolution study of $SiN_X$. $SiN_X$ is oxidized to $SiO_2$ in a first step and converted to silicic acid in a second step.[2] Final products include $NH_3$, which the human body produces about 4 g of daily. The same estimated $NH_3$ amount as a device less than or equal to 1 mg.

Figure 9A:
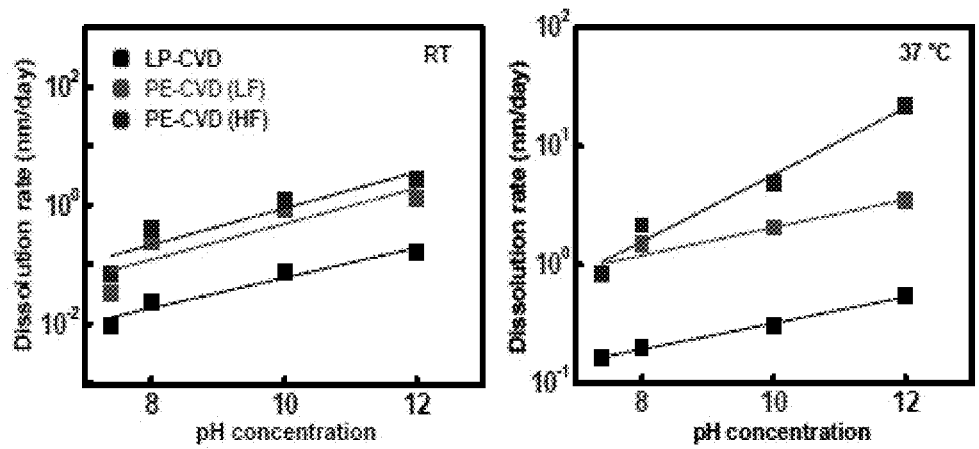
FIG. 9A-9B.
Figure 9B:
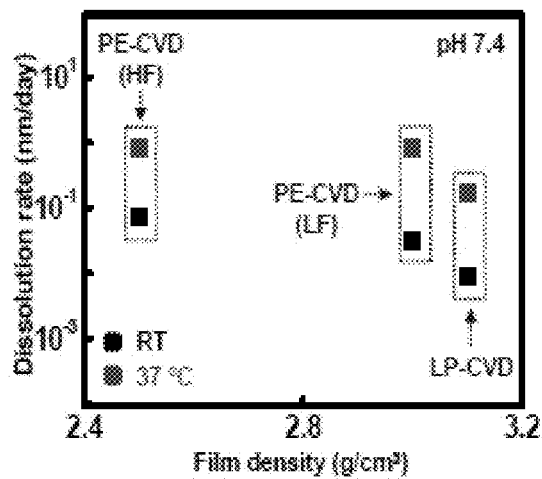

FIG. 9A shows measured data (symbols) and numerical fits (lines) for pH-dependent dissolution kinetics of nitrides (black, low pressure CVD; red, PECVD-LF; blue, PECVD-HF) at room temperature and 37° C. FIG. 9B shows $SiN_x$ film property dependency exhibited as film density versus dissolution rate.

Figure 10:
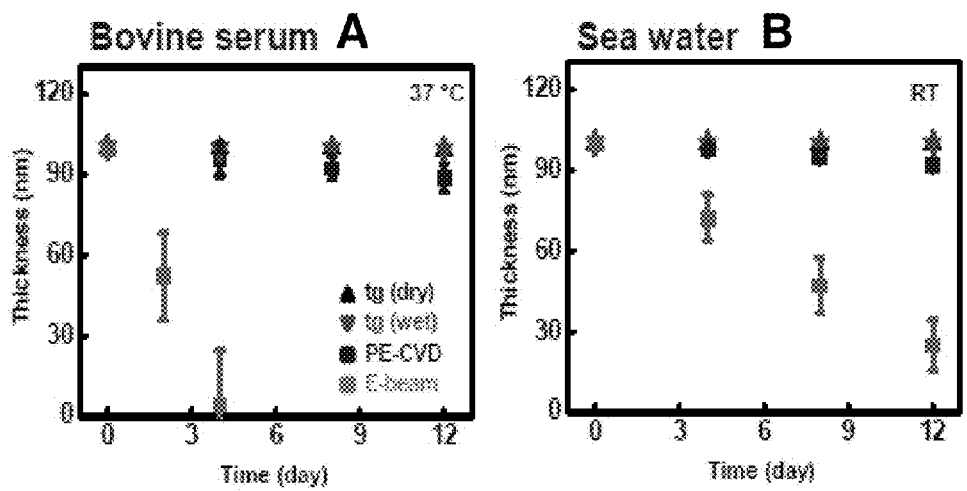
FIG. 10. Dissolution kinetics for different oxides immersed in various aqueous solutions. A) Bovine serum (pH ~7.4) at 37° C. (black, tg-oxide by dry oxidation; red, tg-oxide by wet oxidation; blue, PECVD oxide; magenta, E-beam oxide), B) sea water (pH ~7.8) at RT (black, tg-oxide by dry oxidation; red, tg-oxide by wet oxidation; blue, PECVD oxide; magenta, E-beam oxide), C) Bovine serum (pH ~7.4) at 37° C. (black, LPCVD nitride; red, PECVD nitride with LF mode; blue, PECVD nitride with HF mode), D) sea water (pH ~7.8) at RT (black, LPCVD nitride; red, PECVD nitride with LF mode; blue, PECVD nitride with HF mode).
Figure 10:
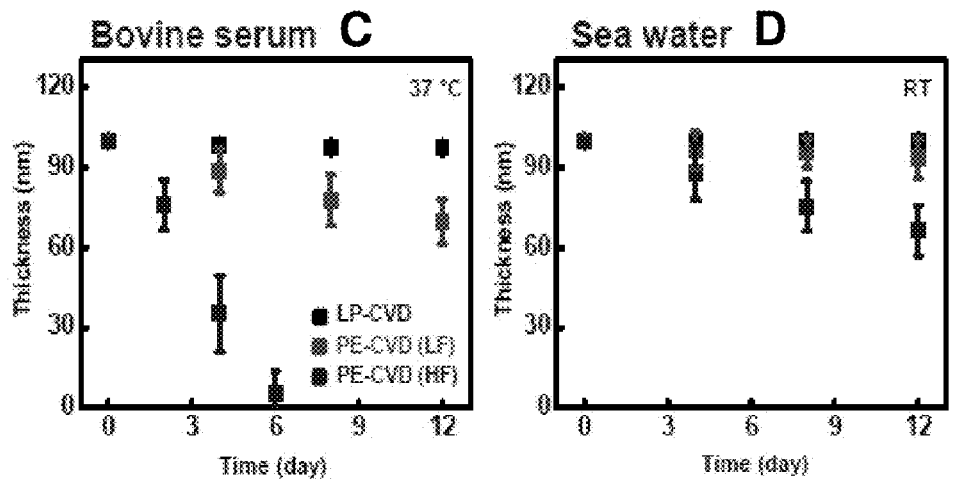

FIG. 10 shows dissolution kinetics for different oxides immersed in various aqueous solutions. A) Bovine serum (pH ~7.4) at 37° C. (black, tg-oxide by dry oxidation; red, tg-oxide by wet oxidation; blue, PECVD oxide; magenta, E-beam oxide), B) sea water (pH ~7.8) at RT (black, tg-oxide by dry oxidation; red, tg-oxide by wet oxidation; blue, PECVD oxide; magenta, E-beam oxide), C) Bovine serum (pH ~7.4) at 37° C. (black, LPCVD nitride; red, PECVD nitride with LF mode; blue, PECVD nitride with HF mode), D) sea water (pH ~7.8) at RT (black, LPCVD nitride; red, PECVD nitride with LF mode; blue, PECVD nitride with HF mode). Dissolution rates of $SiO_2/SiN_x$ in bovine serum and sea water are ~10 and ~4 times faster than buffer solution under the same conditions. Likely, the cations in bovine serum and sea water ($K^+$, $Na^+$, $Ca^{2+}$ and $Mg^{2+}$) accelerate the dissolution rate of $SiO_2$.

Figure 11:
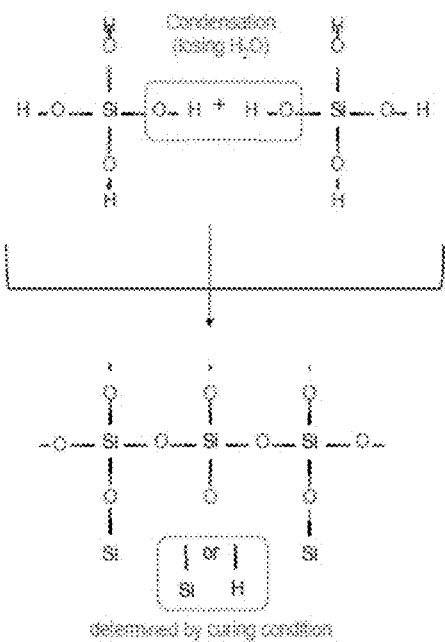
FIG. 11. Curing mechanism and dissolution study of spin-on-glass encapsulation layers cured at various temperatures and times.
Figure 11:
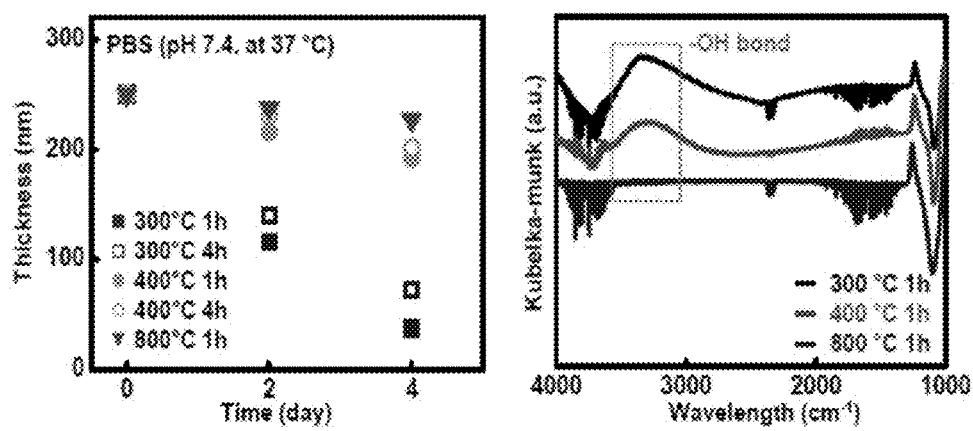

FIG. 11 shows the curing mechanism for spin-on-glass and dissolution studies of spin-on-glass encapsulation layers cured at various temperatures and times. Silicate based spin-on glass (SOG) is dissolvable, and dissolution rate can be controlled by adjusting curing conditions and thickness. Increasing curing temperature and time gives slower dissolution rates due to fewer —OH bonds in the cured SOG. Combining SOG with other oxide layers improves inorganic encapsulation properties.

Figure 12:
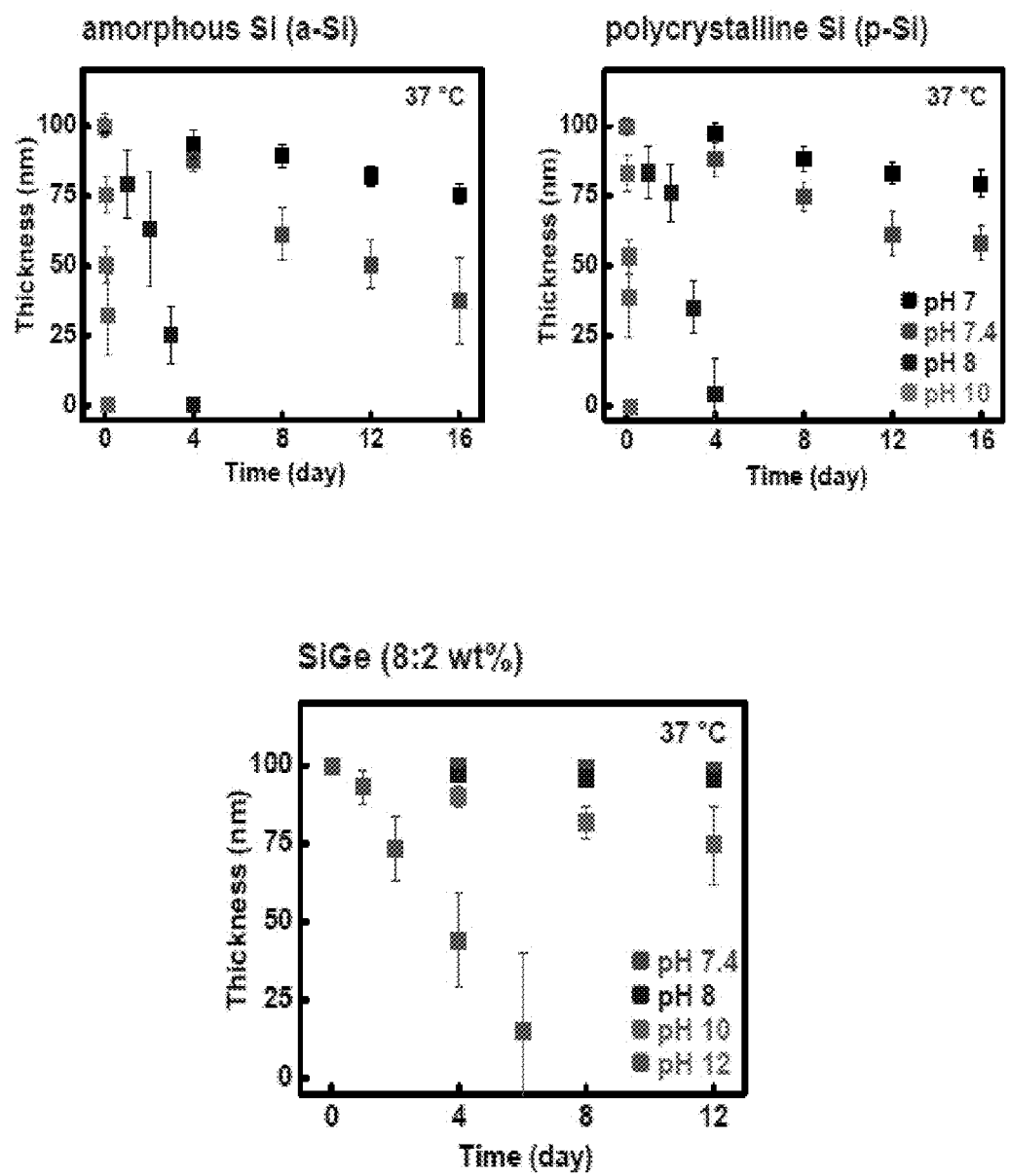
FIG. 12. pH dependent dissolution studies of amorphous silicon (a-Si), polycrystalline silicon (p-Si) and silicon germanide (SiGe).

FIG. 12 shows pH dependent dissolution studies of amorphous silicon (a-Si), polycrystalline silicon (p-Si) and SiGe. The dissolution rate of a-Si/p-Si is similar to single crystalline Si (100), which means the dissolution of Si does not depend on type of Si. Dissolution of SiGe (8:2 wt %) is slightly slower than single crystalline Si because SiGe comprises mostly Si—Si bonds with relatively few Si—Ge bonds (<10%).

Figure 13:
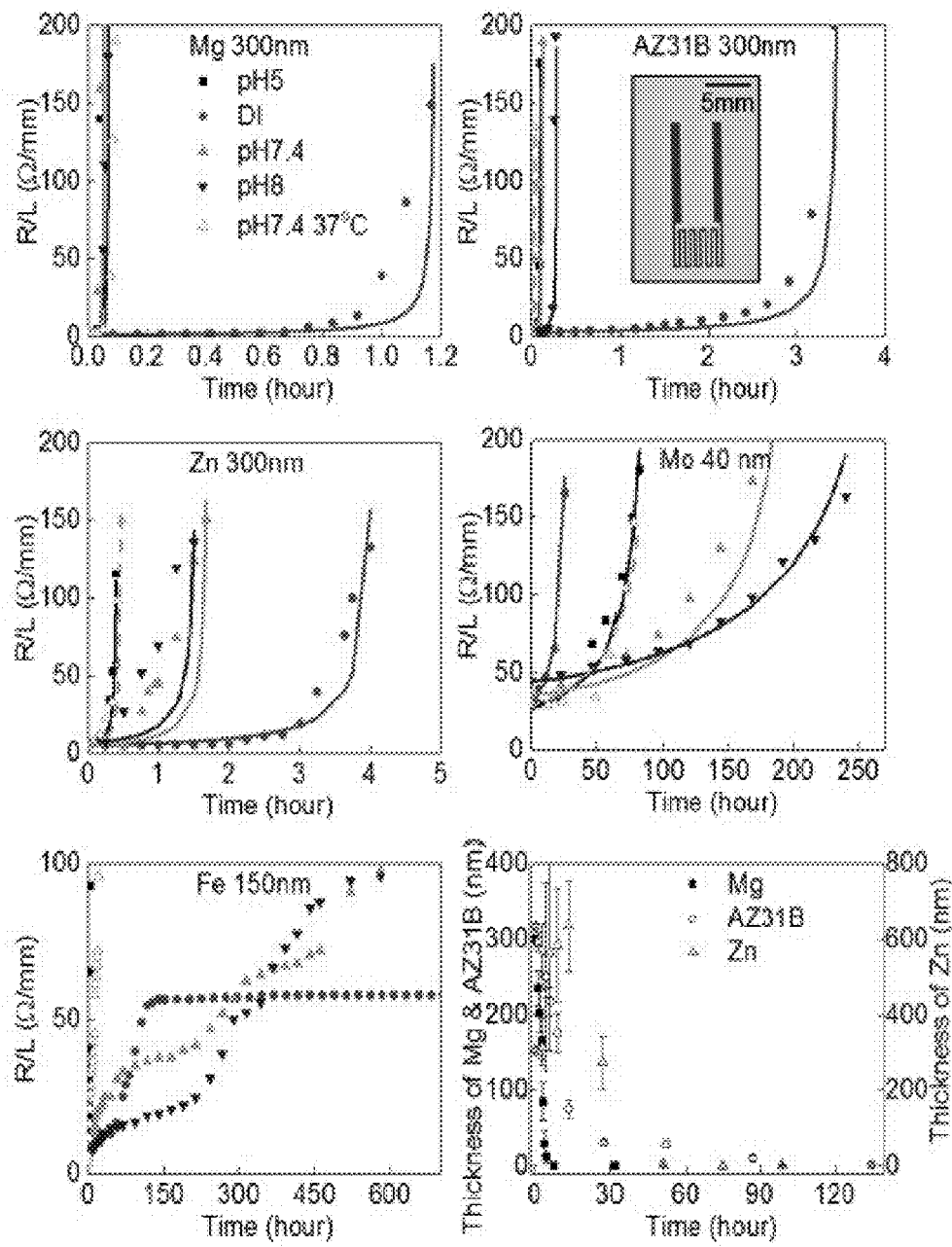
FIG. 13. Electrical dissolution rates and thicknesses of sputter deposited Mg, Mg alloy (AZ31 B, Al 3%, Zn 1%), Zn, Mo, W, CVD deposited W, and E-beam evaporated Fe in DI water and Hanks' solution with pH 5-8.

FIG. 13 shows electrical dissolution rates and thicknesses of sputter deposited Mg, Mg alloy (AZ31 B, Al 3%, Zn 1%), Zn, Mo, W, CVD deposited W, and E-beam evaporated Fe in DI water and Hanks' solution with pH 5-8.

Figure 14:
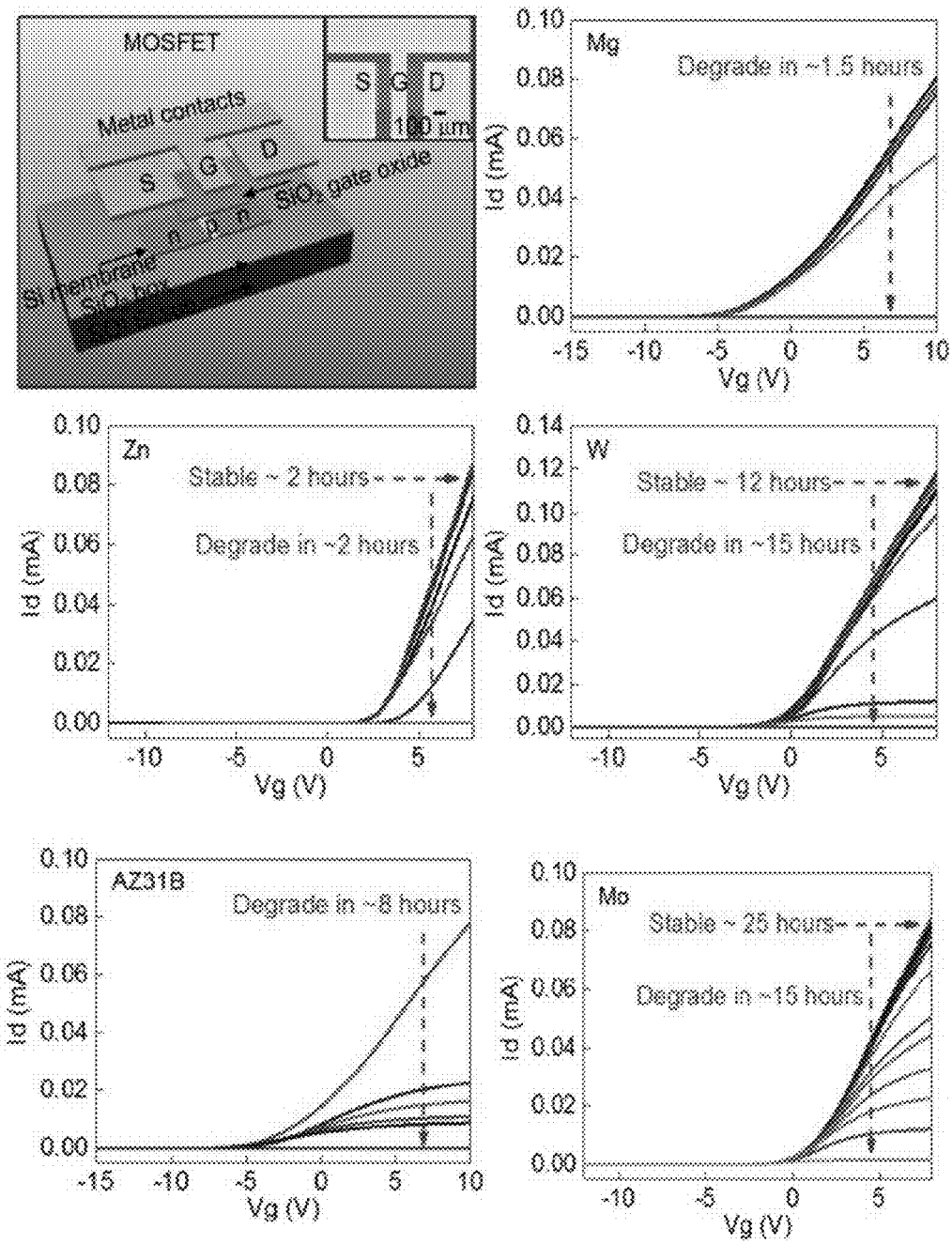
FIG. 14. Current versus voltage plots for devices containing transient metal components.

FIG. 14 shows current versus voltage plots for devices containing transient metal components. N-type MOSFETs built with transient metal thin films exhibit on/off ratios >$10^4$ and mobilities ~250 $cm^2/Vs$. Functionality degradation in DI water was measured without encapsulation at $V_d$=0.2 V.

Figure 15:
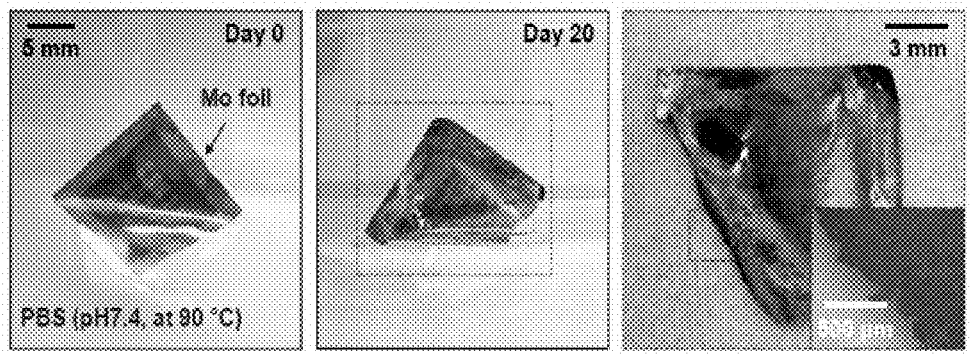
FIG. 15. Photographs showing dissolution of a transient transistor array on a biodegradable metal foil.

FIG. 15 shows photographs of the dissolution of a transient transistor array on a biodegradable metal foil.

Figure 16:
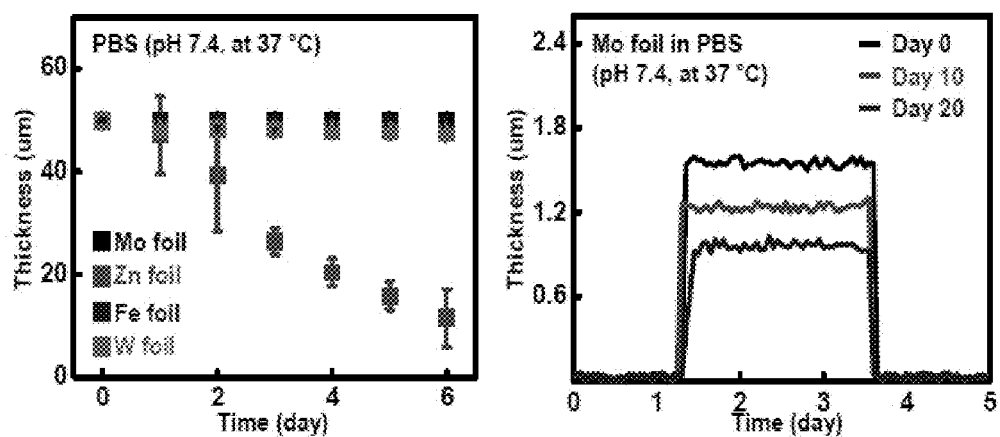
FIG. 16. Dissolution kinetics of various metal foils (Mo, Zn, Fe, W) under physiological conditions (PBS, pH 7.4, 37° C.).

FIG. 16 provides plots of dissolution kinetics of various metal foils (Mo, Zn, Fe, W) under physiological conditions (PBS, pH 7.4, 37° C.).

Figure 17:
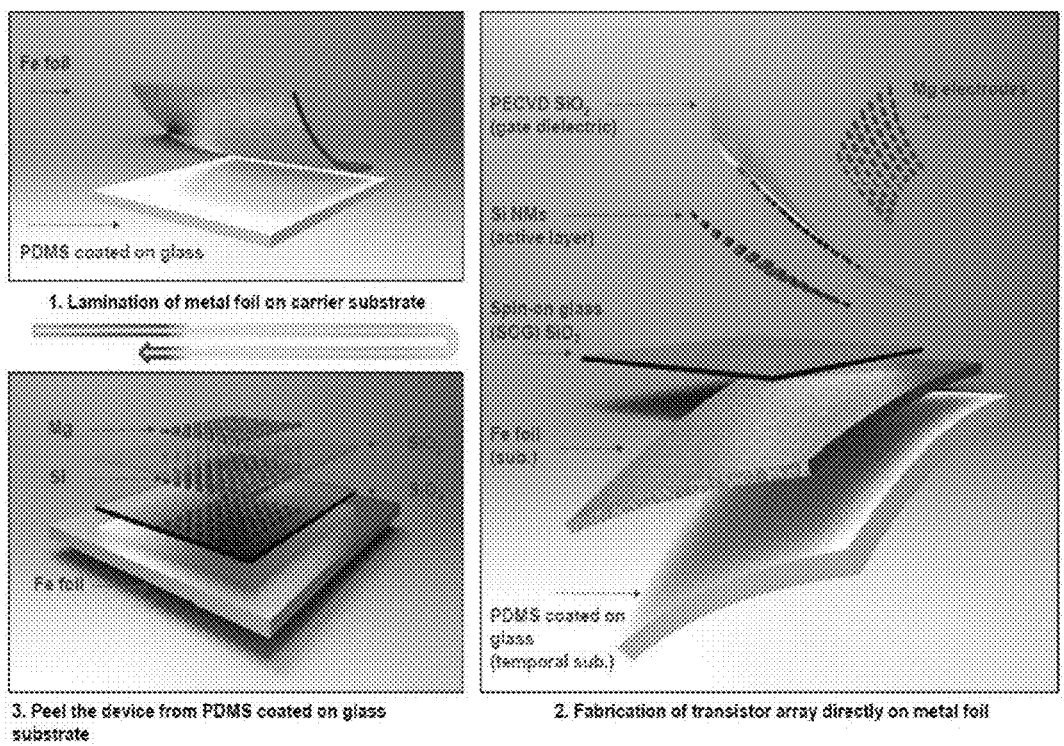
FIG. 17. Schematic of a fabrication strategy using metal foils. 1) Lamination of metal foil on a carrier substrate (e.g., PDMS coated on glass), 2) fabrication of a transistor array directly on the metal foil, and 3) peeling of the device from the carrier substrate.

FIG. 17 provides a schematic of a fabrication strategy using metal foils involving: 1) Lamination of metal foil on a carrier substrate (e.g., PDMS coated on glass), 2) fabrication of a transistor array directly on the metal foil, and 3) peeling of the device from the carrier substrate.

Figure 18:
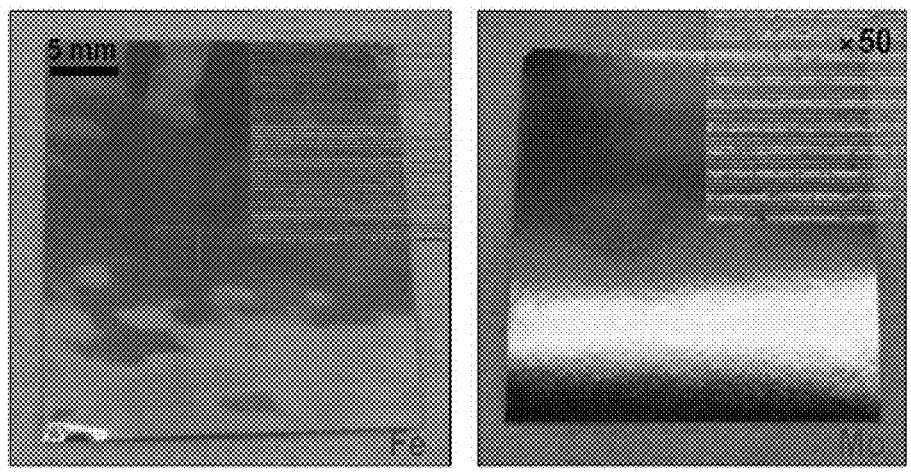
FIG. 18. Demonstrations of inorganic substrates.
Figure 18:
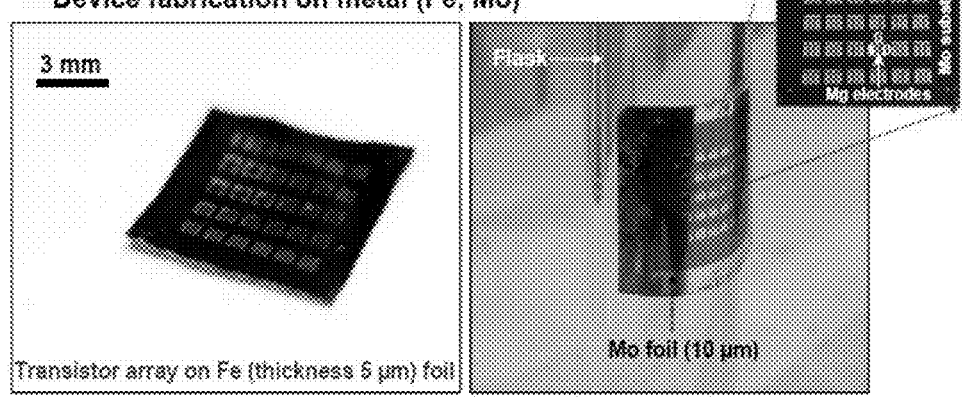

FIG. 18 demonstrate the use of inorganic substrates. For example, metal foils, such as Fe with a thickness of 5 μm or Mo with a thickness of 10 μm, may be used as substrates to support device fabrication. Devices may also be inorganic, e.g. Mg-based transistors. The entire array may be flexible, as shown.

Figure 19:
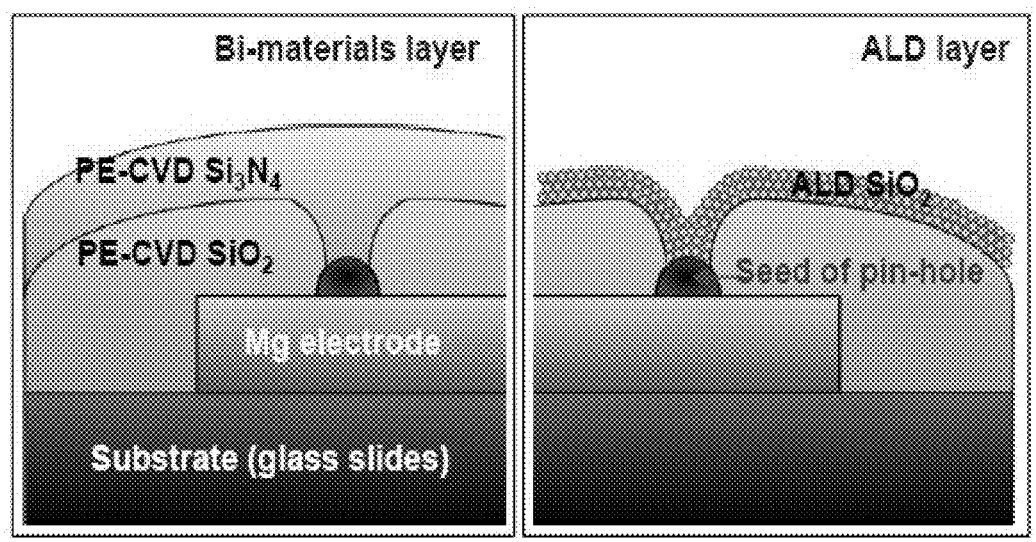
FIG. 19. Schematic illustrations of encapsulation methods for transient electronic devices, showing defects (e.g. pinholes) covered by a bilayer of $SiO_2/Si_3N_4$; ALD provides a defect-free layer.

FIG. 19 provides schematic illustrations of encapsulation methods for transient electronic devices, showing defects (e.g. pinholes) covered by a bilayer of $SiO_2/Si_3N_4$; ALD provides a defect-free layer. Defects, such as pinholes, are the primary cause of leakage of vapors or fluids in encapsulation with PE-CVD $SiO_2$ and $SiN_x$. Multilayer structures of both silicon oxides and silicon nitrides can reduce such defects. An ALD layer has fewer defects than a PE-CVD layer.

Figure 20:
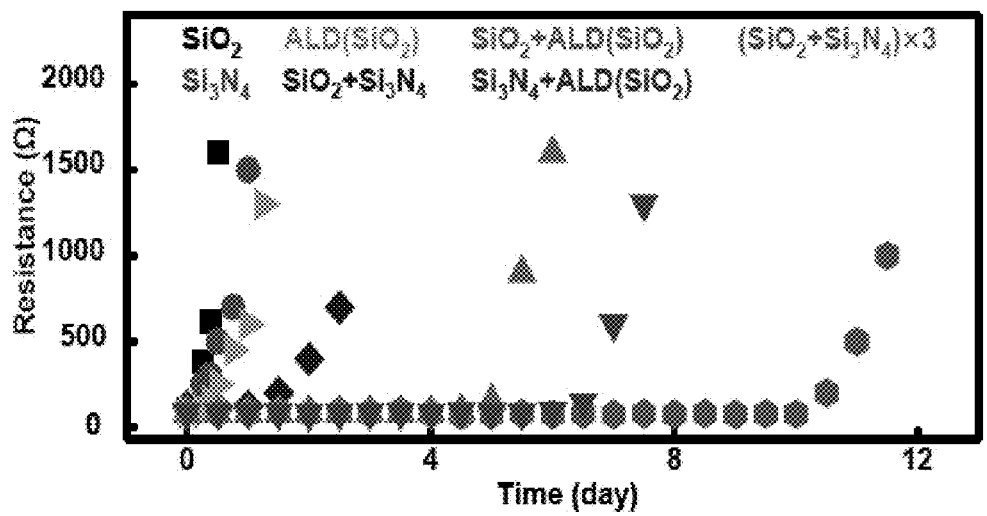
FIG. 20. (A) Measurements of changes in resistance of Mg traces (~300 nm thick) encapsulated with different materials and thicknesses while immersed in deionized (DI) water at room temperature. A single layer of ALD $SiO_2$ (orange, 20 nm), PECVD $SiO_2$ (black, 1 µm) and PECVD-LF $Si_3N_4$ (red, 1 µm), a double layer of PECVD $SiO_2$/PECVD-LF $Si_3N_4$ (blue, 500/500 nm), PECVD $SiO_2$/ALD $SiO_2$ (magenta, 500/20 nm), PECVD-LF $Si_3N_4$/ALD $SiO_2$ (purple, 500/20 nm), and a triple layer of PECVD $SiO_2$/PECVD-LF $Si_3N_4$ (Cyan, 200/200/200/200/100/100 nm) were used for the encapsulation.

FIG. 20 shows measurements of changes in resistance of Mg traces (~300 nm thick) encapsulated with different materials and thicknesses while immersed in deionized (DI) water at room temperature. A single layer of ALD $SiO_2$ (orange, 20 nm), PECVD $SiO_2$ (black, 1 μm) and PECVD-LF $Si_3N_4$ (red, 1 μm), a double layer of PECVD $SiO_2$/PECVD-LF $Si_3N_4$ (blue, 500/500 nm), PECVD $SiO_2$/ALD $SiO_2$ (magenta, 500/20 nm), PECVD-LF $Si_3N_4$/ALD $SiO_2$ (purple, 500/20 nm), and a triple layer of PECVD $SiO_2$/PECVD-LF $Si_3N_4$ (Cyan, 200/200/200/200/100/100 nm) were used for the encapsulation.

Figure 21:
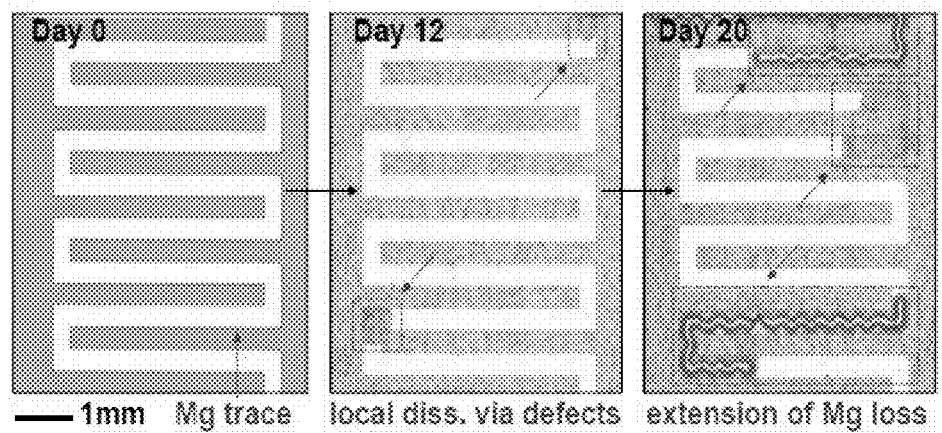
FIG. 21. A series of micrographs of a serpentine trace of Mg (initially ~300 nm thick) during dissolution in DI water at room temperature. Dissolution begins from local defects, then rapidly propagates outward.
Figure 22A:
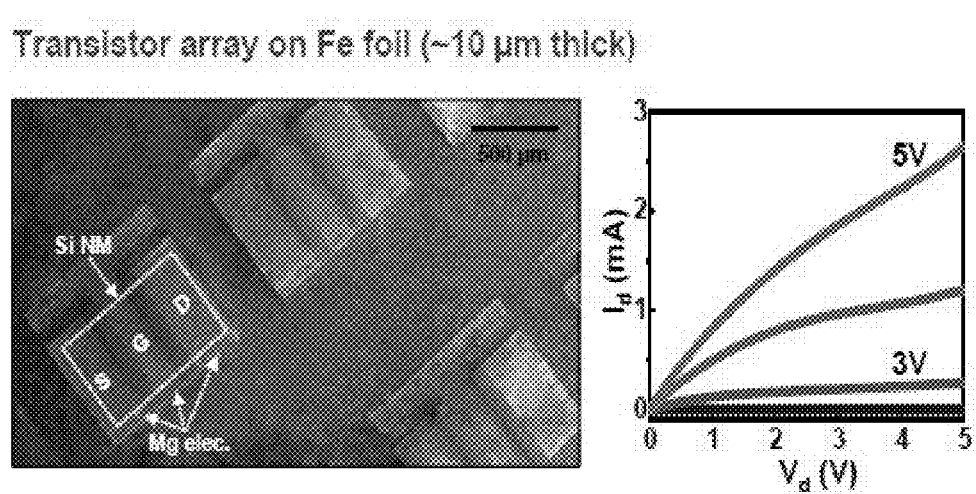
FIG. 22A-22D. Demonstration of the electrical properties of electronic devices fabricated on metal foils.
Figure 22B:
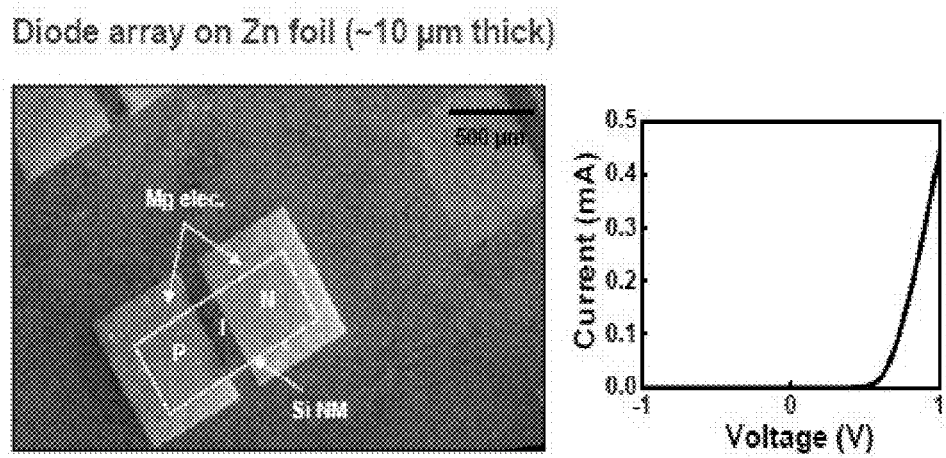
Figure 22C:
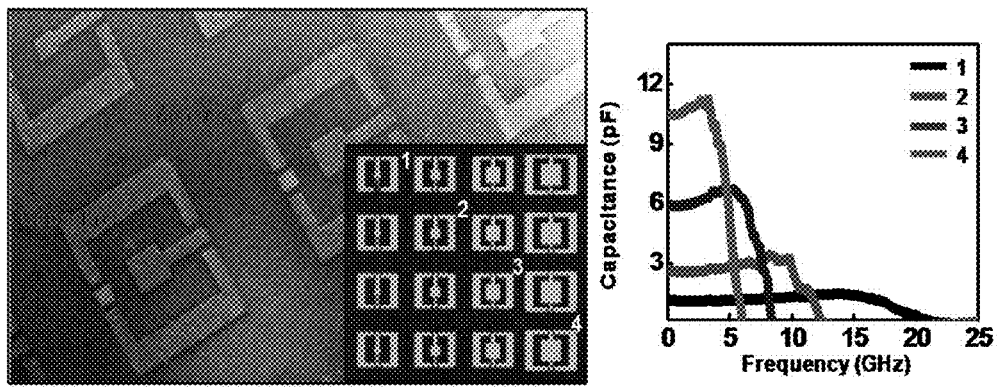
Figure 22D:
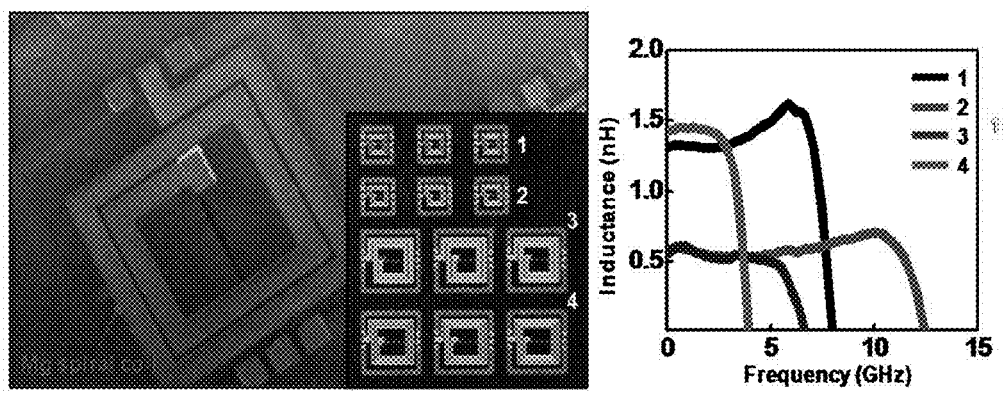
Figure 23A:
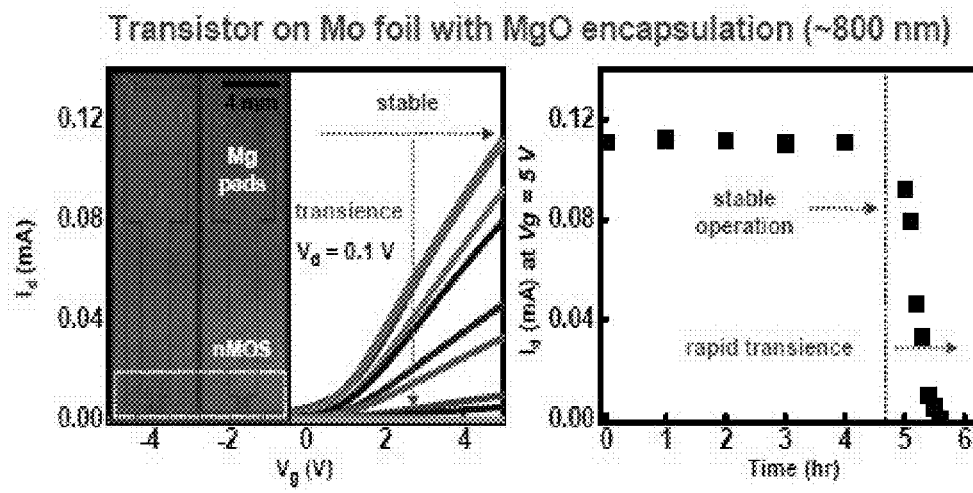
FIG. 23A-23D. Transience of transient devices on inorganic substrates with inorganic encapsulation.
Figure 23B:
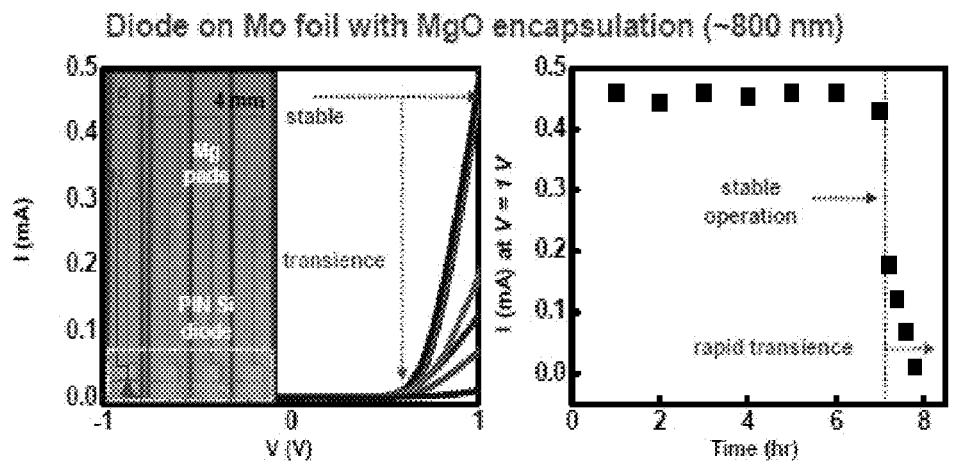
Figure 23C:
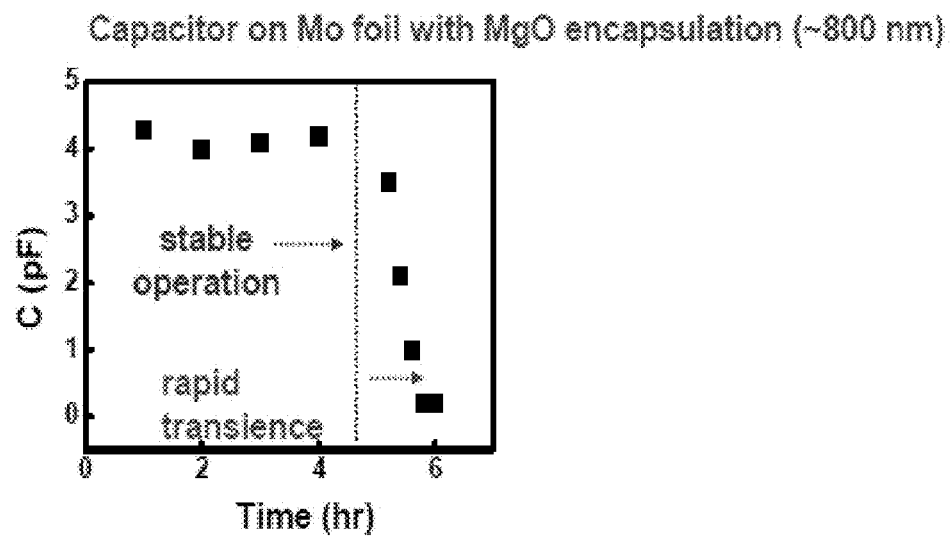
Figure 23D:
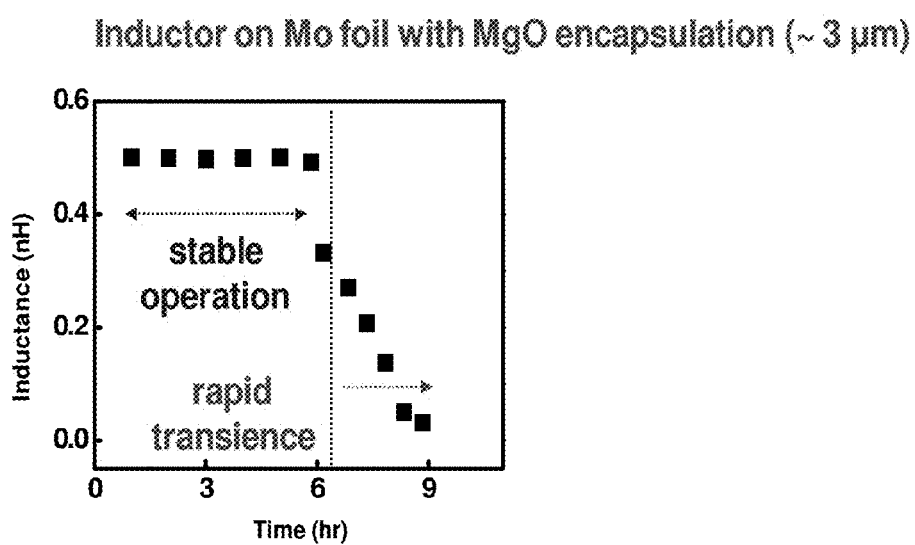

FIG. 21 shows a series of micrographs of a serpentine trace of Mg (initially ~300 nm thick) during dissolution in DI water at room temperature. Dissolution begins from local defects, then rapidly propagates outward.

FIG. 22 shows a demonstration of the electrical properties of electronic devices fabricated on metal foils. (A) Transistor array on Fe foil (~10 μm thick), (B) Diode array on Zn foil (~10 μm thick), (C) Capacitor array on Mo foil (~10 μm thick), (D) Inductor array on Mo foil (~10 μm thick). Electronic devices were successfully fabricated on biodegradable metal substrates (Fe, W, Mo, Zn, Mg). The performance of transient devices on metal substrates is comparable to devices fabricated on non-transient substrates.

FIG. 23 shows transience of transient devices on inorganic substrates with inorganic encapsulation. (A) Transistor on Mo foil with MgO encapsulation (~800 nm), (B) Diode on Mo foil with MgO encapsulation (~800 nm), (C) Capacitor on Mo foil with MgO encapsulation (~800 nm), (D) Inductor on Mo foil with MgO encapsulation.

Figure 24:
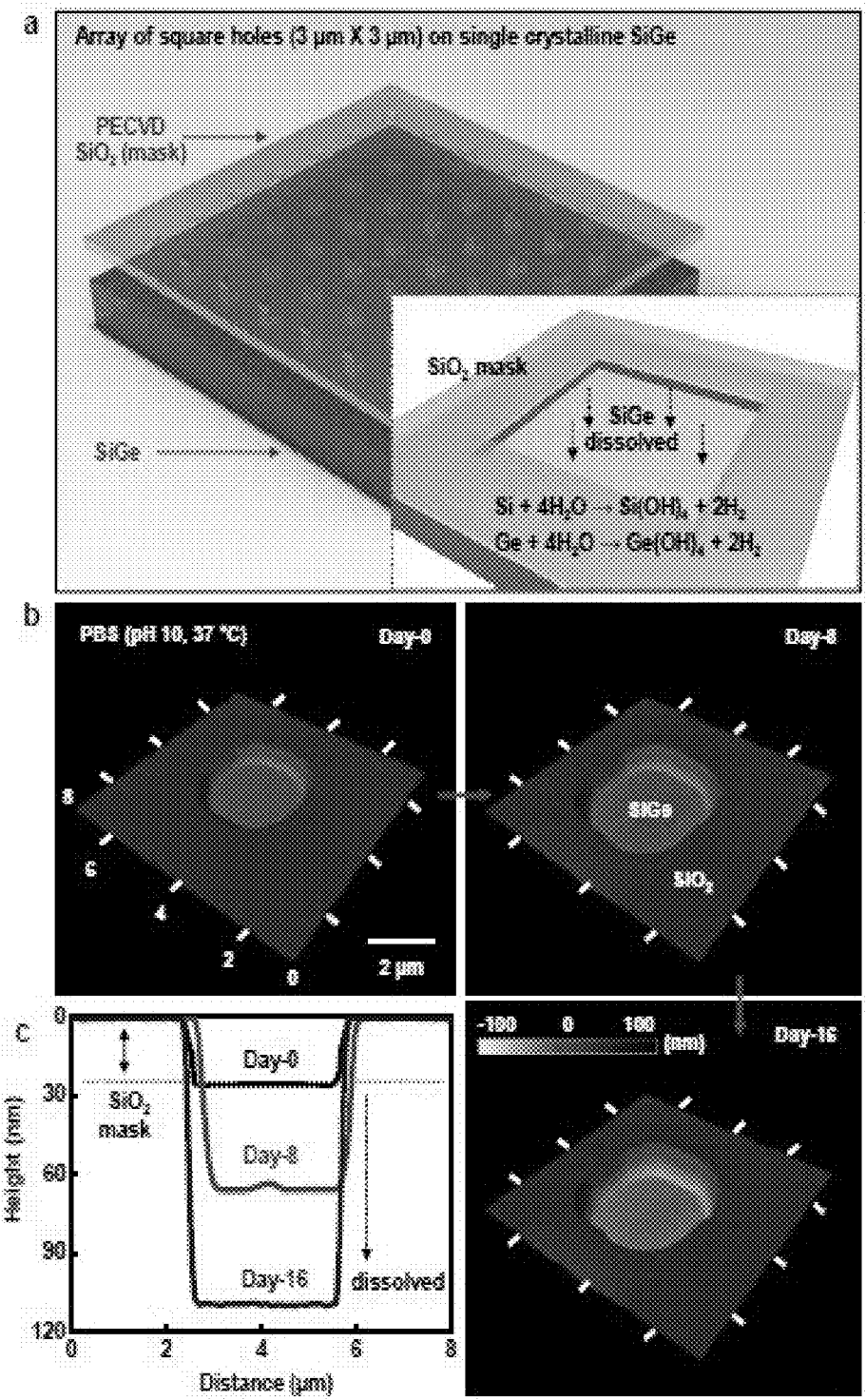
FIG. 24. Sample structure for a dissolution test of single wafer SiGe (Ge) with atomic force microscopy (AFM). (a) Schematic illustration of test structure: array of square holes (3 µm×3 µm×20 nm) of PECVD $SiO_2$ mask on SiGe single wafer. (b) AFM topographical images and c) profiles of SiGe, at different stages of dissolution in buffer solution (pH 10) at 37° C.

FIG. 24 shows a sample structure for a dissolution test of single wafer SiGe (Ge) with atomic force microscopy (AFM). (a) Schematic illustration of test structure: array of square holes (3 μm×3 μm×20 nm) of PECVD $SiO_2$ mask on SiGe single wafer. (b) AFM topographical images and c) profiles of SiGe, at different stages of dissolution in buffer solution (pH 10) at 37° C.

Figure 25:
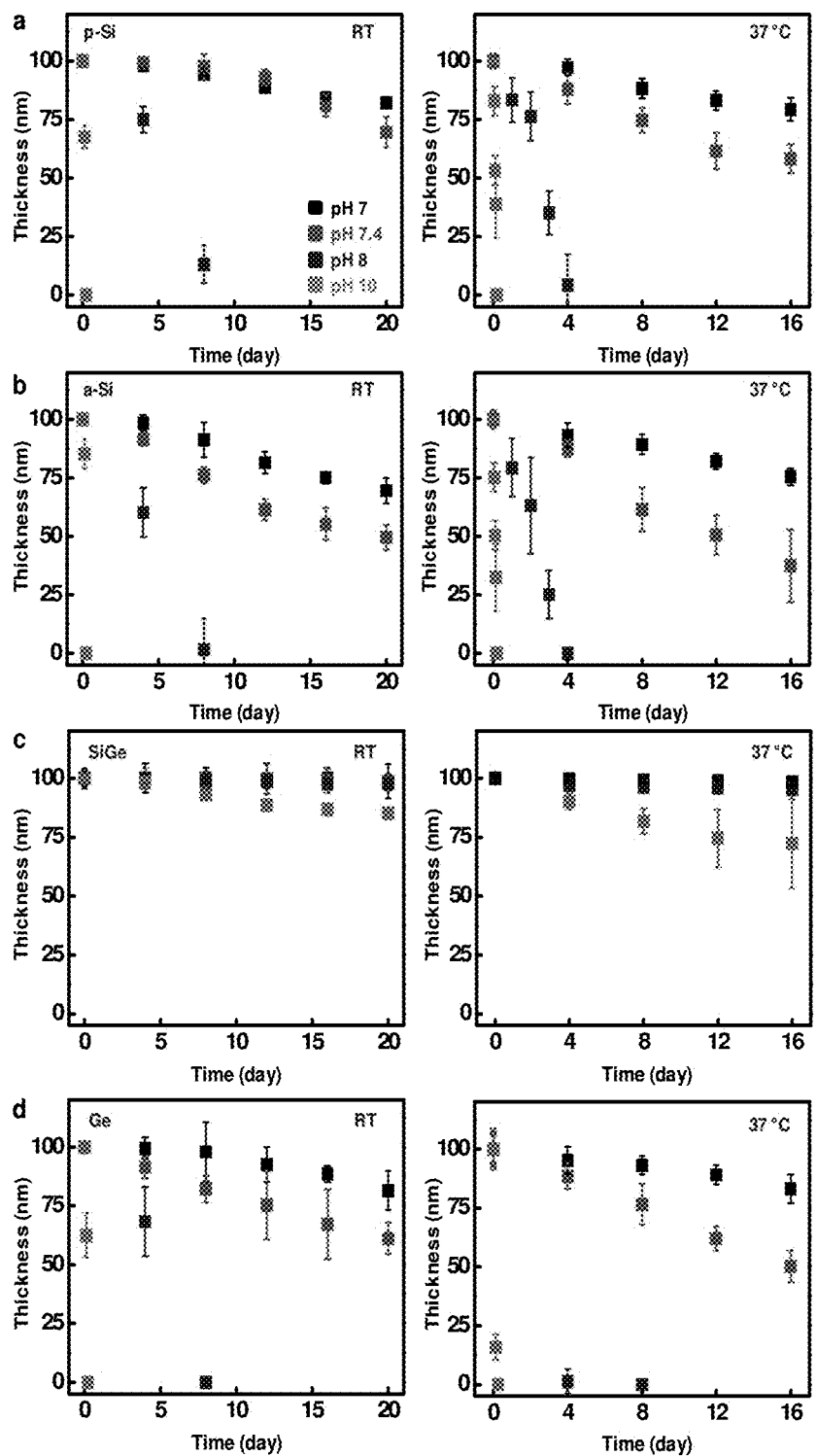
FIG. 25. Dissolution kinetics of various semi-conductors in various buffer solutions, with different pH at room and physiological temperatures. (a) polycrystalline silicon, (b) amorphous silicon, (c) silicon-germanium and (d) germanium.

FIG. 25 shows dissolution kinetics of various semiconductors in various buffer solutions, with different pH at room and physiological temperatures. (a) polycrystalline silicon, (b) amorphous silicon, (c) silicon-germanium and (d) germanium.

Figure 26:
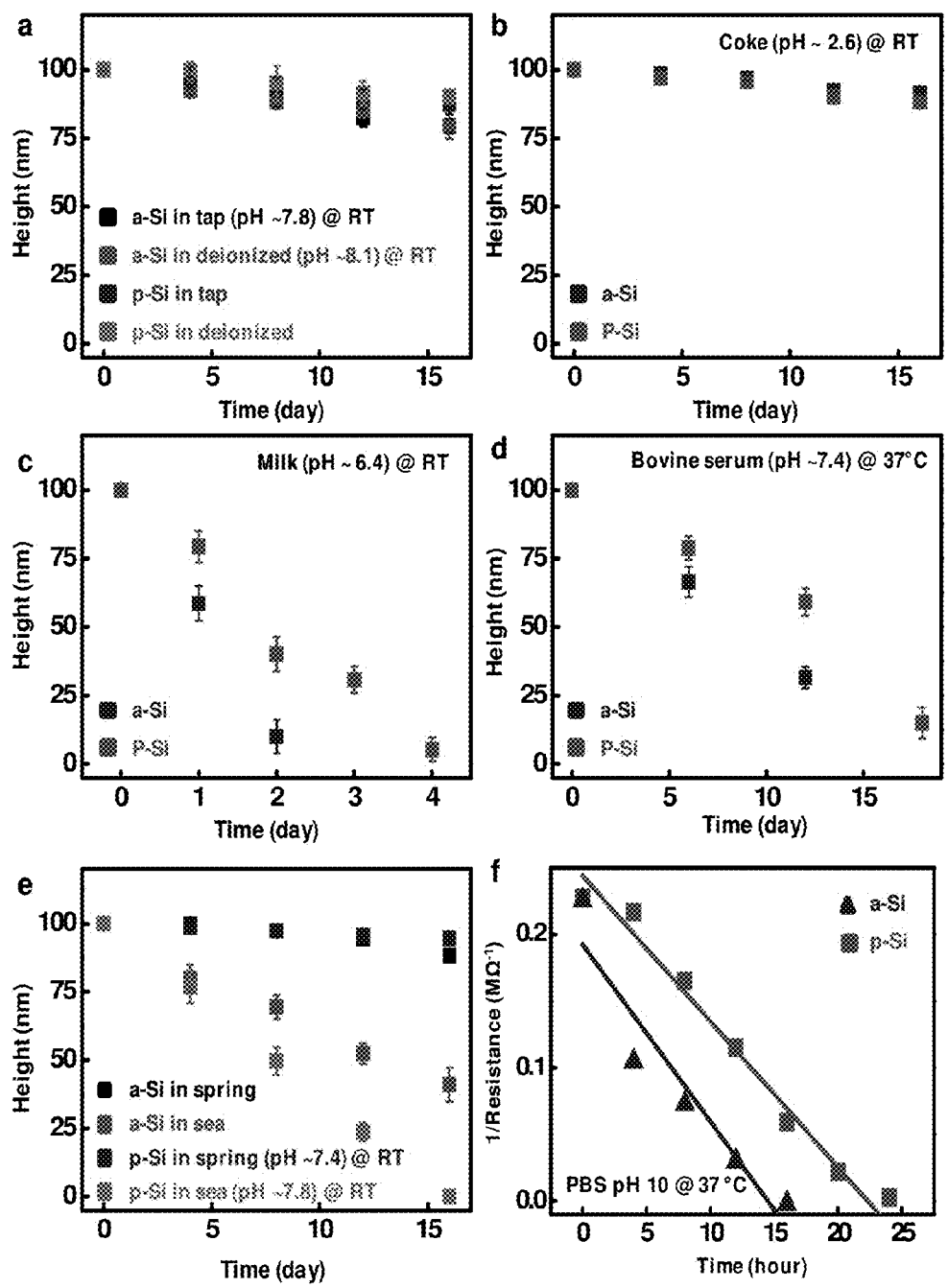
FIG. 26. Dissolution kinetics of different types of silicon in various aqueous solutions. (a) Tap water (pH ~7.8), deionized water (DI, pH ~8.1) and spring water (pH ~7.4), (b) Coke (pH ~2.6), (c) milk (pH ~6.4) at room temperature, (d) bovine serum (pH ~7.4) at room and 37° C., and (e) sea water (pH ~7.8) at room temperature. (f) Changes in resistance of a meander trace formed from a phosphorous doped polycrystalline and amorphous Si NM (~35 nm) in phosphate buffer solution (pH 10) at 37° C.

FIG. 26 shows dissolution kinetics of different types of silicon in various aqueous solutions. (a) Tap water (pH ~7.8), deionized water (DI, pH ~8.1) and spring water (pH ~7.4), (b) Coke (pH ~2.6), (c) milk (pH ~6.4) at room temperature, (d) bovine serum (pH ~7.4) at room and 37° C., and (e) sea water (pH ~7.8) at room temperature. (f) Changes in resistance of a meander trace formed from a phosphorous doped polycrystalline and amorphous Si NM (~35 nm) in phosphate buffer solution (pH 10) at 37° C.

Figure 27:
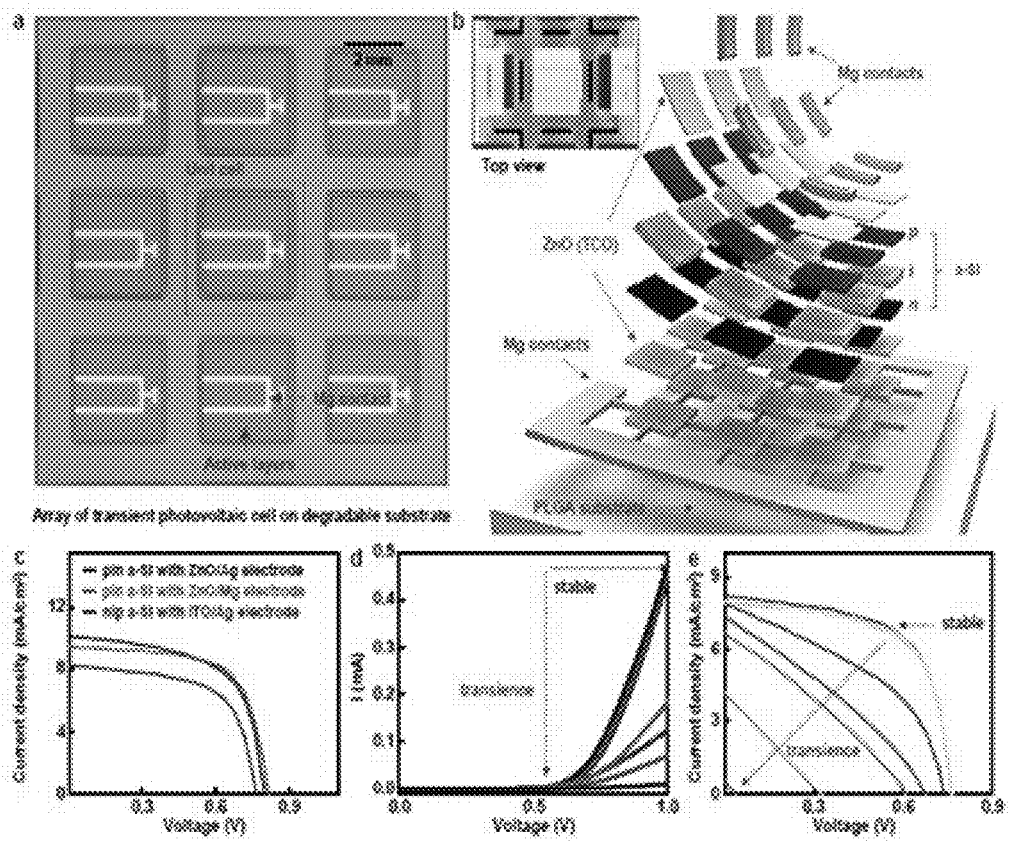
FIG. 27. Thin film solar cell with fully transient materials. (a), (b) Image and structure of amorphous Si based photovoltaic cell array on degradable substrate. (c) Performance of unit cell of solar cells. (d) Electrical transience behavior of a-Si diode and (e) transience of performance of solar cell.

FIG. 27 shows a thin film solar cell with fully transient materials. (a), (b) Image and structure of amorphous Si based photovoltaic cell array on degradable substrate. (c) Performance of unit cell of solar cells. (d) Electrical transience behavior of a-Si diode and (e) transience of performance of solar cell.

REFERENCES

[1] K. G. Knauss & T. J. Wolery, Geochim. Cosmochim. Acta 52, 43-53 (1998). W. A. House & L. A. Hickinbotham, J. Chem. Soc. Faraday, Trans. 88, 2021-2026 (1992).
[2] E. Laarz et al., J. Am. Ceram. Soc. 83, 2394-2400 (2000). Toxicological Profile for Ammonia, published by the U.S. Department of Health and Human Services, ATSDR (2004).

EXAMPLE 3

Dissolution Behaviors and Applications of Silicon Oxides and Nitrides in Transient Electronics Background and Motivation Silicon oxides and nitrides are key materials for dielectrics and encapsulations in a class of silicon-based high performance electronics that has the ability to completely dissolve in a controlled fashion with programmable rates, when submerged in bio-fluids and/or relevant solutions. This type of technology, referred to as 'transient electronics', has potential applications in biomedical implants, environmental sensors and other envisioned areas. The results presented here provide comprehensive studies of transient behaviors of thin films of silicon oxides and nitrides in diverse aqueous solutions at different pH scales and temperatures. The kinetics of hydrolysis of these materials primarily depends on not only pH levels/ion concentrations of solutions and temperatures, but also morphology and chemistry of films determined by the deposition methods and conditions. Encapsulation strategies with a combination of layers demonstrate enhancement of the lifetime of transient electronic devices, by reducing water/vapor permeation through the defects.

Introduction

Materials for insulation, passivation and encapsulation in microelectronics are critically important for proper operation of the devices. Silicon oxides and nitrides are in widespread use not only for digital and analog circuits but also for thin film display electronics and others, due to their excellent properties as gate and interlayer dielectrics, passivation coatings,[1-3] and barriers against water penetration.[4-5] This paper explores the materials aspects of use of these films in a different, emerging class of electronics, whose defining characteristic is solubility in water, with environmentally and biologically benign end products. This type of technology, sometimes referred to as one type of transient electronics, could be important for temporary biomedical implants, resorbable sensors and monitors for the environment, 'green' disposable consumer devices and other systems that are not well served by conventional electronics, which last for decades and involve biologically and environmentally harmful materials. Initial demonstrations relied either on miniaturized, non-degradable inorganic components integrated with resorbable silk substrates and encapsulating layers,[6,7] or on synthetic and/or nature-inspired organic active and passive materials.[8-10] An important advance followed from the observation that monocrystalline, device-grade silicon in ultrathin forms (i.e. nanomembranes), can dissolve, at various rates, in different types of biofluids as well as in seawater and other naturally occurring forms of water, all of relevance to envisioned applications. The end product, silicic acid, is biocompatible and environmentally benign at the low levels of concentration that are associated with small nanomembranes of silicon. Representative examples of demonstration devices include high performance complementary metal-oxide-semiconductor (CMOS) transistors and simple circuits, solar cells, strain/temperature sensors, digital imaging devices, wireless power scavenging systems and others.[11-13] Additional inorganic semiconductor options include ZnO, of interest in part due to its piezoelectric properties, for transient mechanical energy harvesters, actuators and others.[14] In most of these examples, MgO, which undergoes hydrolysis to $Mg(OH)_2$, serves as the dielectric and encapsulation layer. Initial observations suggested that $SiO_2$ might provide another option. Here, we study this material in detail, and also provide evidence that $SiN_x$ represents another alternative.

Dissolution Studies of Different Types of Oxides

Previous work on bulk materials establishes that the mechanism for hydrolysis of silicon oxides is $SiO_2 + 2H_2O \rightarrow Si(OH)_4$.[15-17] Because $OH^{31}$ initiates this reaction, the concentration of $OH^-$ (pH of solution) strongly influences the dissolution rate, as observed in studies of the dissolution kinetics of quartz and amorphous silica.[15-18] Here, we examine materials in forms and with chemistries widely utilized in the semiconductor industry, as thin films grown/deposited using standard or slightly modified techniques. The results reveal essential aspects of hydrolysis in such cases, including the influence of morphology and chemistry, as defined by the conditions and methods for deposition. To examine the dependence of the dissolution rate on pH and type of oxide, systematic studies were performed in buffer solutions with pH between 7.4 to 12, and at different temperatures. Three different classes of materials were examined—thin films of oxides formed by 1) growth using dry ($O_2$ gas) and wet ($H_2O$ vapor) thermal oxidation (tg-oxide), 2) plasma enhanced chemical vapor deposition (PECVD oxide) and 3) electron-beam (E-beam oxide) evaporation.

Figure 28:
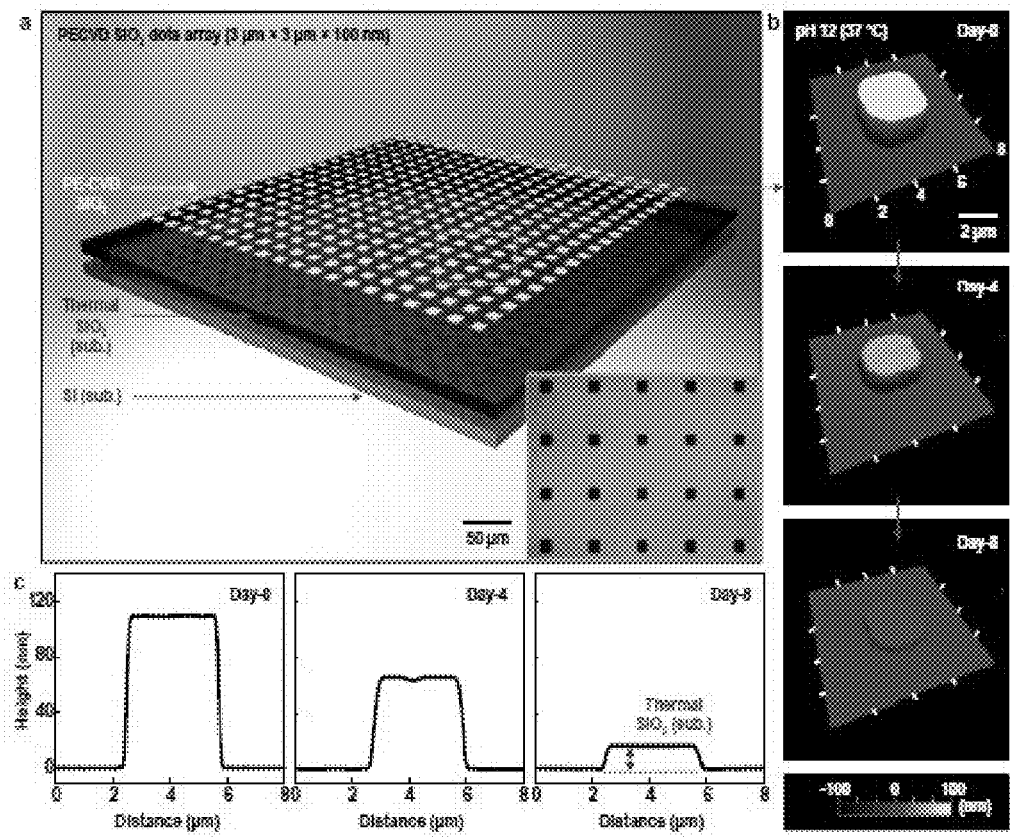
FIG. 28. Schematic illustration, images and data from a structure for testing the dissolution of thin (~100 nm thick) square pads of $SiO_2$ formed by plasma-enhanced chemical vapor deposition (PECVD). a) Schematic illustration of the test structure, which consists of an array of square pads (3 µm×3 µm×100 nm) of PECVD $SiO_2$ deposited at 350° C. on a thermally grown oxide (tg-oxide) on a silicon (100) wafer, with inset optical micrograph. b) AFM topographical images and c) profiles of a representative pad at different stages of hydrolysis in buffer solution (pH 12) at physiological temperature (37° C.).
Figure 29:
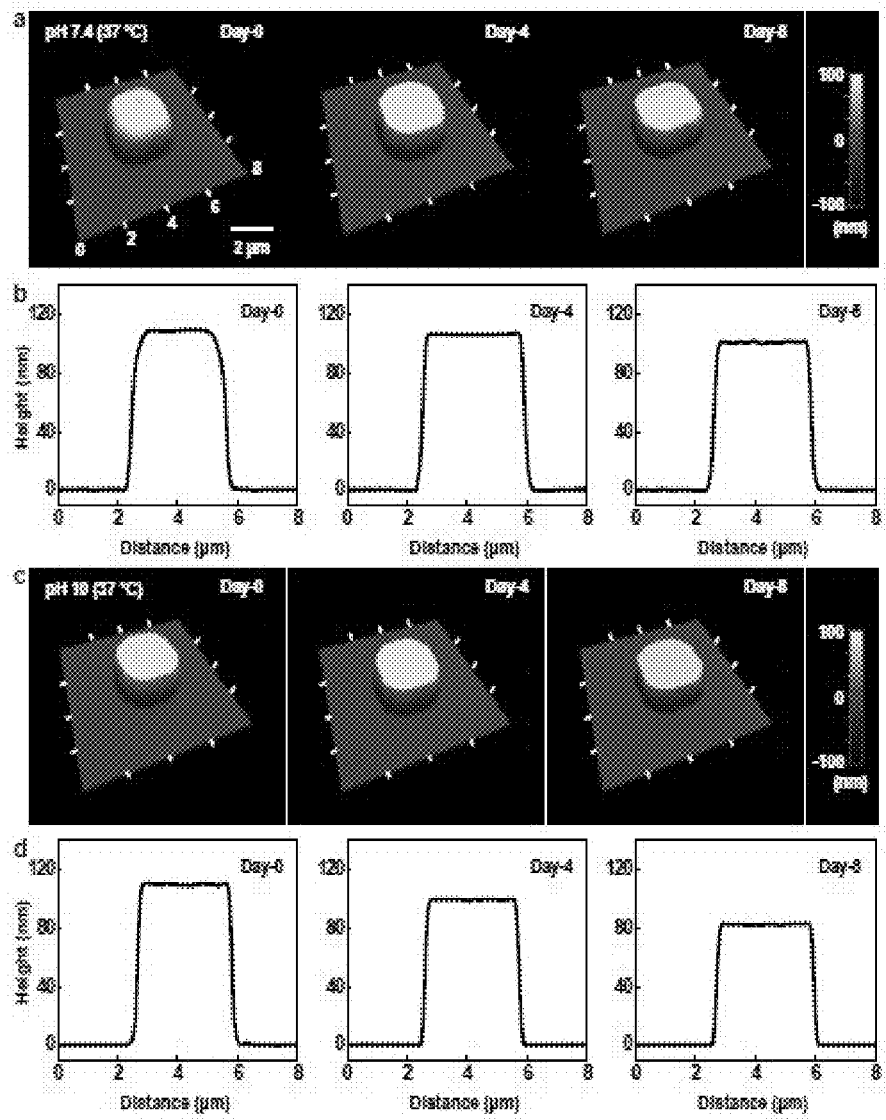
FIG. 29. AFM surface topography and thickness profile for PECVD oxide at various stages of dissolution in (a), (b) buffer solution (pH 7.4) at 37° C., and (c), (d) buffer solution (pH 10) at 37° C.
Figure 30:
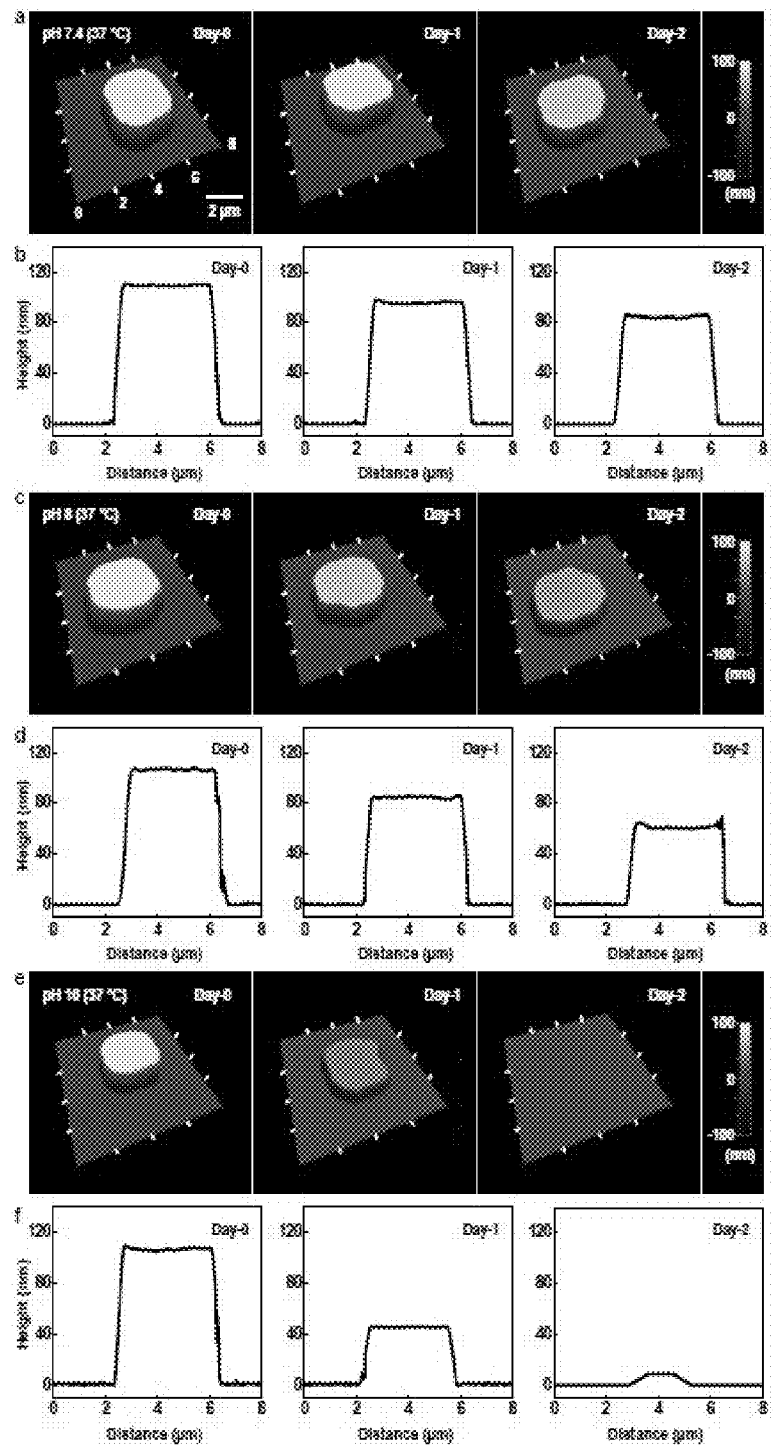
FIG. 30. AFM surface topography and thickness profile for E-beam oxide at various stages of dissolution in buffer solution with (a), (b) pH 7.4, and (c), (d) pH 8, and (e), (f) pH 10, at 37° C.

Spectroscopic ellipsometry (J. A. Wooldman Co. Inc., USA) revealed the dissolution rate as a time dependent change in thickness. Atomic force microscopy (AFM, Asylum Research MFP-3D, USA) provided information on the surface topography as well as independent measurements of thickness. Test structures of PECVD and E-beam materials for AFM measurements consisted of arrays of isolated square films (3 μm×3μm×100 nm) patterned on tg-oxide, whose dissolution rate is much slower than that of other materials, as shown subsequently. FIG. 28*a* presents a schematic illustration of a test structure, and an optical micrograph in the inset. FIGS. 28*b* and 28*c* provide AFM images and thickness profiles at several stages of immersion in aqueous buffer solution (pH 12) at 37° C. (Additional AFM images appear in FIGS. 29 and 30). These results indicate that the oxides dissolve in a uniform fashion, without any significant change in surface topography, formation of flakes or other non-ideal behaviors like those observed, for example, in transient metals under similar conditions.[19] In all cases, samples were immersed in ~50 mL of aqueous solutions, removed, rinsed and dried, and then measured (spectroscopic ellipsometry; AFM). After measurements (total times of several hours), samples were placed back into fresh solutions. The solutions were replaced every other day. (The dissolution rates, for all cases examined, did not change substantially for various time intervals for solution replacement (e.g. for every 1, 2, 4 or 7 days).

FIG. 31*a-c* and FIG. 6(1) provide the dissolution kinetics of tg-oxide (dry and wet oxidation), PECVD oxide and E-beam oxide in terms of the change in thickness as a function of time in buffer solutions (pH 7.4 to 12) at room temperature (RT) and 37° C. The tg-oxides and E-beam oxide exhibit the slowest and fastest rates, respectively, under the same conditions. Four main factors affect the rate: temperature, pH and ionic content of the solutions, and chemical/morphological properties of the films. The dissolution rate of each oxide increases with temperature, with an expected Arrhenius dependence, consistent with previous studies.[17, 20]

Figure 31:
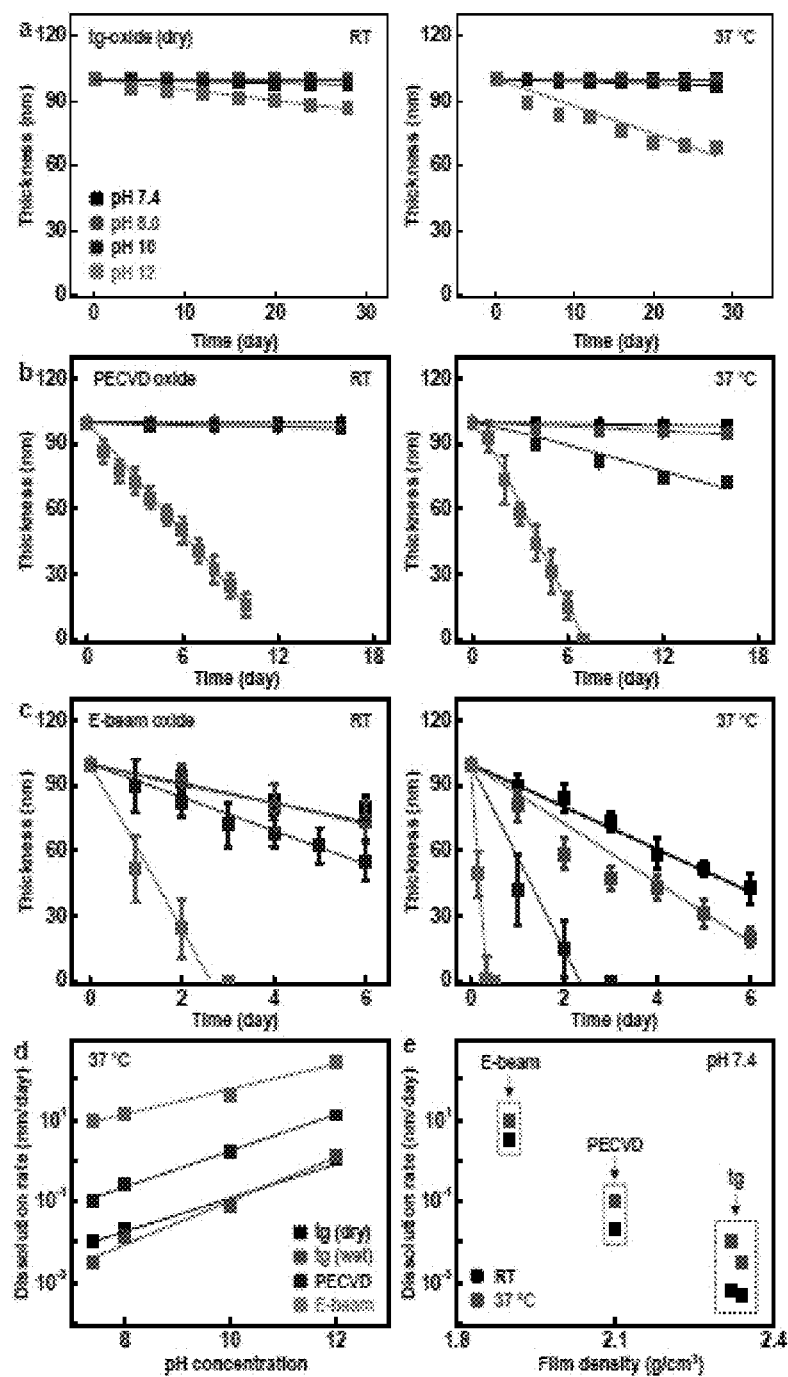
FIG. 31. Dissolution kinetics, as defined by the rate of change of film thicknesses, of different silicon oxides in various aqueous solutions, with different values of pH at room and physiological temperatures. a) Calculated (lines) and measured (symbols) values for the time-dependent dissolution of thermally grown $SiO_2$ (dry oxidation) in buffer solutions (black, pH 7.4; red, pH 8; blue, pH 10; purple, pH 12) at room (left) and physiological (right, 37° C.) temperature. b) Calculated (lines) and measured (symbols) dissolution behaviors of PECVD $SiO_2$ in diverse aqueous solutions with different pH at room (left) and physiological (right, 37° C.) temperature. c) Calculated (lines) and experimental (symbols) results of dissolution studies on E-beam $SiO_2$ in aqueous solutions at different pH and temperature. d) Dependence of dissolution kinetics of silicon oxide films on pH (black, tg-oxide (dry); red, tg-oxide (wet); blue, PECVD $SiO_2$; purple, E-beam $SiO_2$) at physiological temperature (37° C.) corresponding to experimental data (symbol) and numerical fits (line). e) Measurements of dissolution rates of silicon oxides as a function of film density in buffer solution (pH 7.4) at room (black) and physiological (red, 37° C.) temperature.

FIG. 31*d* shows a linear dependence of the dissolution rate for each type of oxide in buffer solutions with different pH at (see more details at RT in FIG. 7), similar to related observations.[15-17] The relationship can be written log r=a+n[pH], where r is the dissolution rate, and a and n are constants (n=0.33 for quartz when r is in mol/m²s).[16] The values of n for the data in FIG. 31*d* and FIG. 7 are between 0.31 to 0.44 (at 37° C.) and 0.22 to 0.62 (at RT), respectively. The kinetics can also be influenced by the concentration of ions in the solution.[21,22] As an example, bovine serum (pH ~7.4) and sea water (pH ~7.8) show rates that are ~9 and ~4 times higher than those observed at similar pH in buffer solution, respectively, likely due to the presence of additional ions (ex. $K^+$, $Na^+$, $Ca^{2+}$ and $Mg^{2+}$) in these liquids.[21,22]

The dissolution rate can also be affected, of course, by the physical and chemical properties of the films, which in turn depend on growing/deposition methods and conditions. Thermal oxide is known to be uniformly dense.[23] Oxide created by PECVD can show different stoichiometries and densities, due to by-products from the $SiH_4$ source gas as it reacts with Si to form Si—H. Such effects can be particularly important for low temperature deposition.[24] E-beam oxide formed from a pure source of $SiO_2$ (i.e. pellets) can involve nanoscale fragmentation during evaporation, which can potentially lead to alterations in the stoichiometry and reductions in density.[25]

X-ray photoelectron spectroscopy (XPS) and X-ray reflectometry (XRR) reveal the stoichiometries, atomic bond configurations and densities. The tg-oxide (dry oxidation) and PECVD oxide have chemistries close to $SiO_2$ (i.e., Si:O=1:2), while the E-beam oxide is oxygen rich, at $SiO_{2.2}$ (Si:O=1:2.2), as shown in Table 1.

TABLE 1

Atomic concentration of different silicon oxides measured by XPS. Carbon (C) and fluorine (F) are considered surface contamination.

| (%) | Si | O | C | F | x ($SiO_x$) |
|---|---|---|---|---|---|
| tg-$SiO_2$ (dry) | 31.6 | 64.0 | 4.3 | 0.1 | 2.0 |
| PECVD $SiO_2$ | 31.5 | 63.5 | 3.6 | 1.4 | 2.0 |
| E-beam $SiO_2$ | 27.5 | 61.3 | 10.8 | 0.4 | 2.2 |

Figure 32:
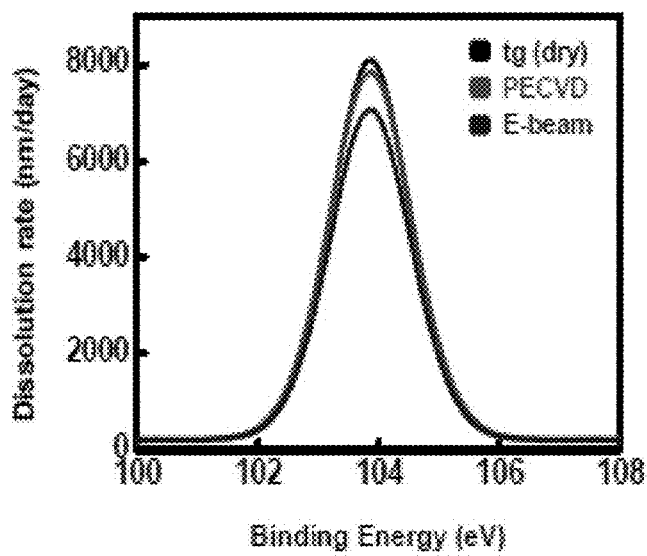
FIG. 32. Bonding energy of Si 2p for tg-oxide (black, dry oxidation), PECVD oxide (red), and E-beam oxide (blue) measured by XPS.
Figure 33:
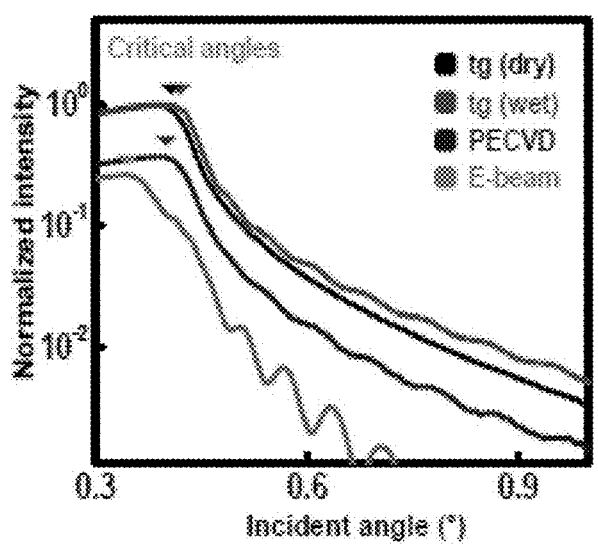
FIG. 33. Measured density of several oxides (black, tg-oxide by dry oxidation; red, tg-oxide by wet oxidation; blue, PECVD oxide; magenta, E-beam oxide) determined by XRR. The triangles indicate the critical angles.

The Si 2P spectra (FIG. 32) indicate that the Si—O bond energies are almost identical for the three oxides. FIG. 31*e* and FIG. 33 show the dependence of the dissolution rate on the film density (~2.3 g/cm³ for tg-oxides, ~2.1 g/cm³ for PECVD oxide, ~1.9 g/cm³ for E-beam oxide). Reduced density can enhance the ability of aqueous solutions to diffuse into the material, thereby accelerating the hydrolysis reaction by increasing the reactive surface area.[11,19,26] Previous research[11,19,26] suggests that a reactive diffusion model can capture some of the behaviors. A modified version of this model, assuming applicability of continuum physics, provides a simple, approximate means to incorporate the effect of density variations associated with porosity. Here, the concentration of water in the porous material is first determined from the partial differential equation for reactive diffusion $D_g^2 \partial w/\partial z^2 - kw = \partial w/\partial t$, where k and $D_e$ are the reaction constant and the diffusivity in the porous media, respectively. Since the mass of the air pore is negligible compared with that of the porous material, the effective density $\rho_{eff}$ of the porous material is related to the density $\rho_s$ of the fully dense material as $$\rho_{eff} = \frac{V_s}{V_{air} + V_s}\rho_s, \quad (1)$$

where $V_s$ and $V_{air}$ are the volumes of material and air pore, respectively. At time t=0, the air pores are filled with water, or $w|_{t=0} = w_0(\rho_s - \rho_{eff})/\rho$, $(0 \leq z < h_0)$. The water concentration is constant at the top surface of the material $w|_{z=h0} = w_0 (w_0 = 1$ g/cm$^3$) and the water flux is zero at the bottom surface $\partial w/\partial z|_{z=0} = 0$. By the method of separation of variables, the water concentration field can be written $$w(y,t) = w_0 \left\{ \frac{\cosh\left(\sqrt{\frac{kh_0^2}{D_e}} \frac{y}{h_0}\right)}{\cosh\sqrt{\frac{kh_0^2}{D_e}}} + \right. \quad (2)$$

$$\left. 2\pi \sum_{n=1}^{\infty} B_n (-1)^n \left(n - \frac{1}{2}\right) e^{-\left[\frac{kh_0^2}{D_e} + \left(n - \frac{1}{2}\right)^2 \pi^2\right]\frac{D_e t}{h_0^2}} \cos\left[\left(n - \frac{1}{2}\right)\pi \frac{y}{h_0}\right]\right\},$$

where $B_n$ is $$B_n = \frac{1}{\frac{kh_0^2}{D_e} + \left(n - \frac{1}{2}\right)^2 \pi^2} + \frac{\frac{\rho_{eff}}{\rho_s} - 1}{\left(n - \frac{1}{2}\right)^2 \pi^2}. \quad (3)$$

When one mole of material reacts with q moles of water, then integration of materials dissolved at each location through the thickness and over time leads to an expression for the remaining thickness h, normalized by its initial thickness $h_0$ as $$\frac{h}{h_0} = 1 - \frac{w_0 M}{q\rho_{eff} M_{H_2O}} \frac{kh_0^2}{D_e} \quad (4)$$

$$\left\{ \frac{D_e t}{h_0^2} \frac{\tanh\sqrt{\frac{kh_0^2}{D_e}}}{\sqrt{\frac{kh_0^2}{D_e}}} - 2\sum_{n=1}^{\infty} B_n \frac{1 - e^{-\left[\frac{kh_0^2}{D_e} + \left(n - \frac{1}{2}\right)^2 \pi^2\right]\frac{D_e t}{h_0^2}}}{\left[\frac{kh_0^2}{D_e} + \left(n - \frac{1}{2}\right)^2 \pi^2\right]} \right\}.$$

The effective diffusivity of water in a porous medium is linearly proportional to the pores available for the transport, which is equivalent to the air fraction in the porous medium $$D_e \propto \frac{V_{air}}{V_{air} + V_s} = \frac{\rho_s - \rho_{eff}}{\rho_s}. \quad (5)$$

The density of SiO$_2$ is 2.33 g/cm$^3$, 2.10 g/cm$^3$ and 1.90 g/cm$^3$ for the case of thermally grown, PECVD and E-beam oxides, respectively. If SiO$_2$ with a density of 2.34 g/cm$^3$ has a diffusivity of $8 \times 10^{-16}$ cm$^2$/S at body temperature, then the diffusivities for PECVD SiO$_2$ and E-beam SiO$_2$ can be calculated from Equation (5) as $1.6 \times 10^{-14}$ cm$^2$/s and $2.92 \times 10^{-14}$ cm$^2$/s. Reaction constants are fitted to the experimental data and the dissolution rate, $-dh/dt$, is then estimated from $$-\frac{dh}{dt} = \frac{w_0 M}{q\rho_{eff} M_{H_2O}} kh_0 \left\{ \frac{\tanh\sqrt{\frac{kh_0^2}{D_e}}}{\sqrt{\frac{kh_0^2}{D_e}}} - 2\sum_{n=1}^{\infty} B_n e^{-\left[\frac{kh_0^2}{D_e} + \left(n - \frac{1}{2}\right)^2 \pi^2\right]\frac{D_e t}{h_0^2}} \right\}, \quad (6)$$

which can be simplified to $$-\frac{dh}{dt} = \frac{w_0 M}{q\rho_{eff} M_{H_2O}} kh_0 \frac{\tanh\sqrt{\frac{kh_0^2}{D_e}}}{\sqrt{\frac{kh_0^2}{D_e}}}. \quad (7)$$

Figure 34:
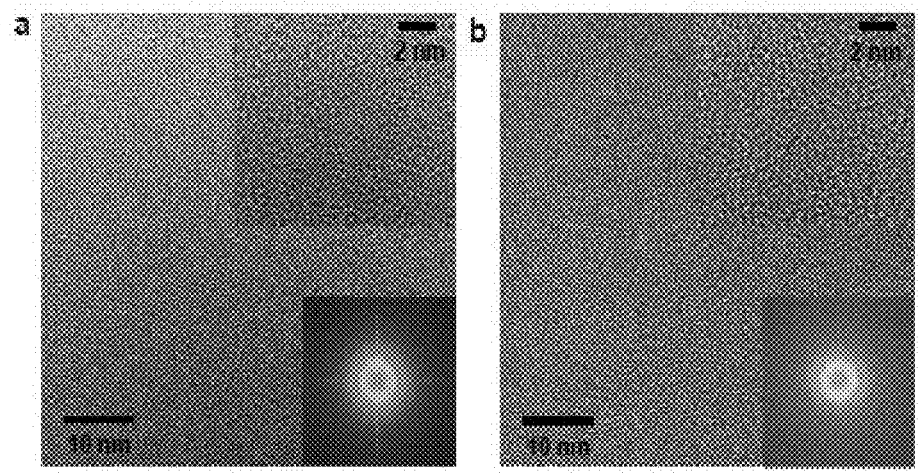
FIG. 34. TEM images and diffraction patterns (inset) of a) PECVD oxide and b) E-beam oxide.
Figure 35:
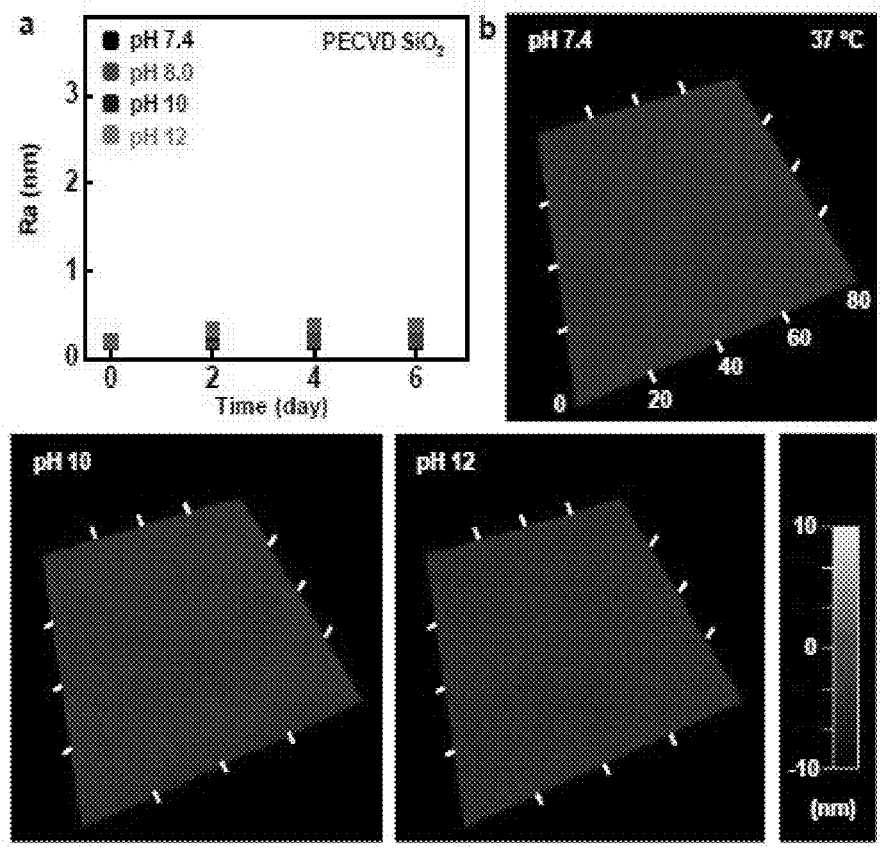
FIG. 35. AFM measurements of surface roughness of PECVD $SiO_2$ while immersed in different pH solutions at 37° C. a) Average surface roughness (Ra) at various stages of dissolution in buffer solution (black, pH 7.4; red, pH 8; blue, pH 10; magenta, pH 12), b) surface topographic images after 6 days in buffer solution (top right, pH 7.4; bottom left, pH 10; bottom right, pH 12).

In FIG. 31a-c, the reaction constants (k) are $1.7 \times 10^{-9}$ (tg-oxide with dry oxidation), $1.6 \times 10^{-8}$ (PECVD oxide), and $1.3 \times 10^{-9}$ (E-beam oxide) s$^{-1}$ in buffer solution with pH 7.4 at 37° C. The results suggest that density influences the dissolution rate not only through changes in rates for diffusion into the material, but also through differences in reactivity. One possibility is that dissolution can occur not just at a molecular level, but also through removal of nanoscale pieces of material that might be released from the film as narrow regions of the porous matrix disappear by hydrolysis. Careful transmission electron microscopy (TEM, JEOL 2010F, USA) studies (FIG. 34) suggest, however, that the porous structures in the PECVD and E-beam oxides do not involve voids with dimensions larger than one or two nanometers. AFM observation of surfaces with sub-nanometer roughness (average roughness <0.4 nm, FIG. 35) throughout the course of the dissolution process also supports the notion that the film disappears uniformly and gradually, at the molecular level, without the release of pieces of material. Additional work is necessary to uncover an atomic level understanding of the dependence of reactivity on density.

Dissolution Studies of Various Classes of Nitrides

Studies of the dissolution kinetics of silicon nitrides were performed in procedures and under conditions similar to those for the silicon oxides. Silicon nitride hydrolyzes in aqueous solution in two steps: (1) oxidation into silicon oxide ($Si_3N_4 + 6H_2O \rightarrow 3SiO_2 + 4NH_3$) and (2) hydrolysis of silicon oxide ($SiO_2 + 2H_2O \rightarrow Si(OH)_4$), where the overall reaction is $Si_3N_4 + 12H_2O \rightarrow 3Si(OH)_4 + 4NH_3$.[27-29] Because silicon dioxide serves as an intermediate product in these reactions, the dependence of rate on pH might be expected to be similar to that observed in the oxides. Low pressure chemical vapor deposition (LPCVD) and PECVD techniques were used to form the silicon nitrides studied here. For PECVD nitrides, two different frequency modes were employed to vary the properties of the films, including residual stress. Spectroscopic ellipsometry revealed the changes in thickness of films deposited on silicon substrates.

Figure 36:
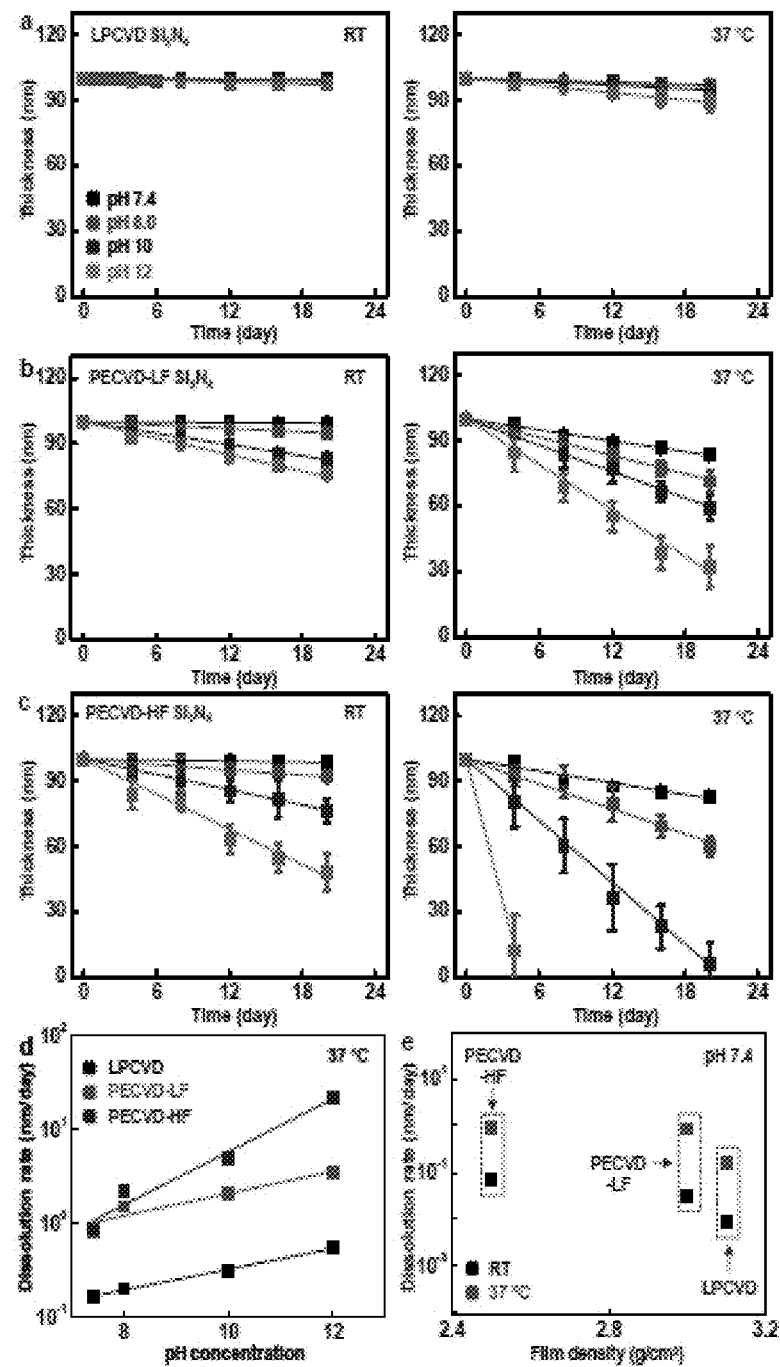
FIG. 36. Dissolution kinetics via hydrolysis of various silicon nitrides in aqueous solutions at different pH and temperature. a) Calculated (lines) and measured (symbols) values for the dissolution of $Si_3N_4$ formed by low-pressure chemical-vapor deposition (LPCVD) in buffer solutions (black, pH 7.4; red, pH 8; blue, pH 10; purple, pH 12) at room (left) and physiological (right, 37° C.) temperature. b) Calculated (lines) and measured (symbols) dissolution behaviors of PECVD $Si_3N_4$ (low-frequency mode) in diverse aqueous solutions with different pH at room (left) and physiological (right, 37° C.) temperature. c) Calculated (lines) and experimental (symbols) results of dissolution study on PECVD $Si_3N_4$ (high-frequency mode) in aqueous solutions at different pH and temperature. d) Calculated (lines) and experimental (symbols) results of the dependence of dissolution kinetics of silicon nitride films on pH (black, LP-CVD $Si_3N_4$; red, PE-CVD $Si_3N_4$ (low frequency); blue, PE-CVD $Si_3N_4$ (high frequency)) at physiological temperature (37° C.). e) Measured dissolution rate of silicon nitrides as a function of film density in buffer solution (pH 7.4) at room (black) and physiological (red, 37° C.) temperature.

FIG. 36a-c shows the dissolution behavior of LPCVD nitride, PECVD-LF nitride (low frequency, LF) and PECVD-HF nitride (high frequency, HF) in buffer solutions (pH 7.4 to 12) at RT and 37° C. Here, three factors (temperature, pH and film characteristics) were considered. The dissolution rate increases with temperature, as expected. FIG. 36d and FIG. 9 show the pH dependence, which is similar to that observed in the oxides. The kinetics suggests a linear relationship between dissolution rate and pH according to log r=a+n [pH], where n ranges from 0.11 to 0.28 for 37° C. and 0.26 to 0.31 for RT. As with the oxides, the nitrides were studied in bovine serum at 37° C. and sea water at RT; the rates are ~8 times and ~4 times higher than those at similar pH in buffer solution, likely due to chemical substances in the serum and sea water (FIG. 10).

Effects of stoichiometry and density were also investigated. Table 2 shows that the stoichiometry of the LPCVD film is $Si_3N_{3.9}$, while that of the PECVD films is $Si_3N_{4.3}$(LF) and $Si_3N_{3.3}$ (HF).

TABLE 2

Atomic concentration of different silicon nitrides measured by XPS. Carbon (C) and fluorine and (F) are considered surface contamination

| (%) | Si | N | F | C | x ($Si_3N_x$) |
|---|---|---|---|---|---|
| LPCVD $Si_3N_4$ | 36.3 | 47.8 | 5.3 | 10.7 | 3.9 |
| PECVD-LF $Si_3N_4$ | 35.2 | 50.6 | 6.2 | 8.1 | 4.3 |
| PECVD-HF $Si_3N_4$ | 36.9 | 40.1 | 11.8 | 11.2 | 3.3 |

Figure 37:
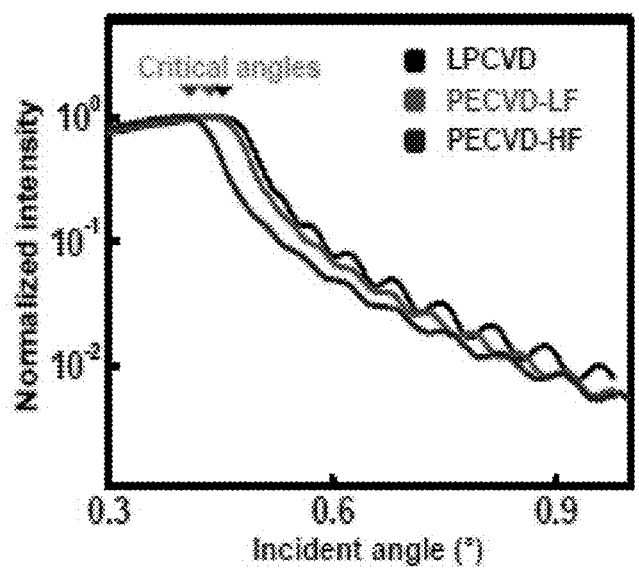
FIG. 37. Densities of nitrides (black, LPCVD nitride; red, PECVD nitride with LF mode; blue, PECVD nitride with HF mode) measured by XRR. The triangles indicate the critical angles.

FIG. 36e and FIG. 37 show the dependence of the dissolution rate on average film density. The densities are 3.1 g/cm$^3$ for LPCVD, 3.0 g/cm$^3$ for PECVD-LF and 2.5 g/cm$^3$ for PECVD-HF. The results suggest that LPCVD nitride exhibits the lowest dissolution rate, at least partly due to its favorable stoichiometry and high density. PECVD-HF nitride shows the fastest dissolution rate due to its non-stoichiometric chemistry and its low density. The modified reactive diffusion model described previously can provide some utility in capturing the effects of porosity, subject to limitations associated with its approximations. From the results of FIG. 36a-c, the reaction constants (k) were found to be $8.0 \times 10^{-8}$, $4.5 \times 10^{-7}$, and $4.0 \times 10^{-7}$ s$^{-1}$ for LPCVD nitride, PECVD-LF nitride and PECVD-HF nitride, respectively, in buffer solution (pH 7.4) at 37° C. by modified reactive diffusion model where the density of closely packed amorphous nitrides was 3.16 g/cm$^3$.

Encapsulation Strategy with Inorganic Layers

In addition to their use as gate and interlayer dielectrics, silicon oxides and nitrides can be considered as transient passivation/encapsulation layers. These materials are well known to be good barrier materials for permeation of water vapor in conventional electronics.[4,5,30,31] Previous research[4,31] on encapsulation with PECVD oxide and nitride in organic light-emitting diode (OLED) devices indicates that defects, such as pinholes, are a primary cause of leakage of vapors or fluids. We show here that multilayer structures of both silicon oxides and nitrides can reduce such defects and that these materials can be used in transient electronics.

Figure 38:
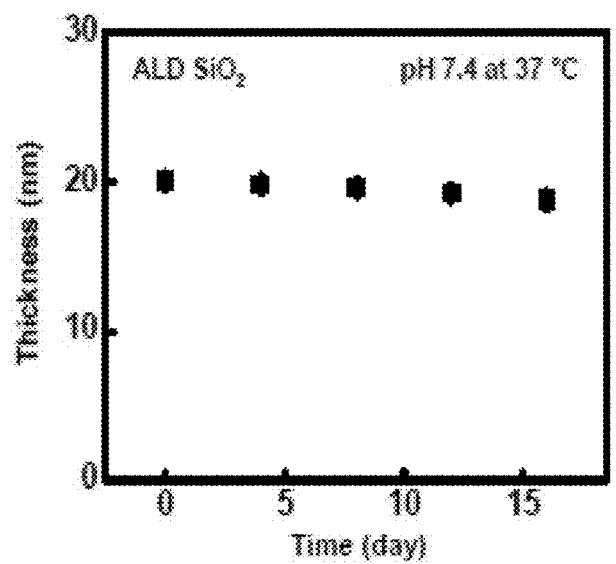
FIG. 38. Measurements of changes in thickness of ALD $SiO_2$ during immersion in buffer solution (pH 7.4) at 37° C.

As shown in FIG. 19, a combination of multiple different layers, i.e. $SiO_2$ and $Si_3N_4$, improves the performance of the encapsulation. Multiple layers with different materials can reduce water/vapor permeation through an underlying layer, by cooperative elimination of defects.[4,31] Atomic layer deposition (ALD) provides a complementary strategy to reduce effects arising from defects.[32,33] A double layer of PECVD $SiO_2$ (or PECVD-LF $Si_3N_4$) and ALD $SiO_2$ represents effective means of encapsulation, even with thin layers (FIG. 19). The dissolution rate of a single layer of ALD $SiO_2$ is 0.08 nm/day in buffer solution (0.1 M, pH 7.4) at 37° C. (FIG. 38), similar to that of PECVD $SiO_2$ in the same conditions.

FIG. 20 presents measured changes in resistance of a serpentine-shaped Mg trace (~300 nm), with several encapsulation approaches at various times for immersion in deionized water at room temperature. Samples with a single layer of ALD $SiO_2$ (~20 nm), PECVD $SiO_2$ or $Si_3N_4$ (~1 μm) show increases in resistance after just a few hours of immersion. A combination of PECVD $SiO_2$ (~500 nm) and $Si_3N_4$ (~500 nm) extends this time to ~1 day. Triple layers of PECVD $SiO_2$ and $Si_3N_4$ (~200 nm/200 nm/200 nm/200 nm/100 nm/100 nm, total thickness ~1 μm) extend to ~10 days. Combinations of PECVD $SiO_2$/ALD $SiO_2$ (~500/20 nm) and PECVD $Si_3N_4$/ALD $SiO_2$ (~500/20 nm) show characteristic times of ~5 and ~7 days, respectively. These results suggest that the ALD $SiO_2$ layer has much fewer defects than PECVD $SiO_2$ or $Si_3N_4$. A single layer of ALD (~20 nm) provides similar timescale as a single layer of $SiO_2$ or $Si_3N_4$ (~1 μm). Although combined used of PECVD $SiO_2$ and ALD $SiO_2$ shows extended lifetimes, a single layer of ALD $SiO_2$ itself is not sufficiently thick to cover uniformly the sorts of structures found in transient electronics, with the Mg resistor (~300 nm) as a simple example. These dissolution behaviors lead to two-stage kinetics in the functional transience of this test structure: i) encapsulation layers define the first time period, i.e. stable operation with negligible changes in electrical properties, ii) the Mg defines the second, i.e. rapid degradation in function. The optical microscope images in FIG. 21 clearly reveal that the dissolution of Mg begins with leakage of water from local defects, which then quickly propagate laterally. These results suggest that an efficient encapsulation strategy is critically important in removing these leakage pathways, to increase the time for stable operation. Also, encapsulation with these inorganic materials can be improved by combined use of biodegradable polymers as suggested in previous encapsulation studies in OLED devices.[31,34]

Conclusion

The results reported here provide a foundation of understanding of hydrolysis in silicon oxides and nitrides for applications in transient electronics, and their dependence on temperature, pH and film properties. An appealing aspect of these materials for these applications is that they are already well developed and widely used in conventional electronics. Opportunities range not only from gate and interlayer dielectrics to passivation and encapsulation layers but also to window layers and antireflection coatings in photovoltaics or optoelectronics systems.

Studies of the kinetics of hydrolysis of thin films of silicon oxides and nitrides and the use of these materials as encapsulants were presented for applications. Dissolution rates of various types of silicon oxides and nitrides were examined for their dependence on the pH and ionic concentration, temperature of the solution and the morphology and chemistry of films. The encapsulation approaches based on multiple, different thin layers of oxides and nitrides prevent water permeation for up to 10 days in simple transient electronic test structures.

Experimental Section

Test structures for silicon oxides and nitrides: Thin layers of silicon oxides ($SiO_2$) were prepared in three different ways, all on silicon wafers (University Wafer): (1) Thermally grown (tg-oxides) (dry and wet oxidation), (2) plasma-enhanced chemical vapor deposited from precursor gases (PECVD, Trion Technology, USA) at 350 ° C., and (3) electron beam (E-beam) evaporated from $SiO_2$ pellets (99.99%, Kurt J. Lesker Company, USA). The nitrides were deposited onto similar wafers. The films were formed by low-pressure chemical vapor deposition (LPCVD) and by PECVD (Surface Technology Systems, Newport, UK) at 300° C. using low frequency (LF, 380 kHz) and high frequency (HF, 13.56 MHz). In all cases, the thickness was controlled at ~100 nm. The test structures for measurement by atomic force microscope (AFM) consisted of arrays of square pads (3 µm×3 µm×100 nm), fabricated by photolithography and reactive ion etching (RIE).

Dissolution experiments: Samples were placed into 50 mL of aqueous buffer solutions with different pH (pH 7.4-12, Sigma-Aldrich, USA) at either room temperature (RT) or physiological temperature (37° C.). Studies also involved bovine serum (pH ~7.4, Sigma-Aldrich, USA) at 37° C. and sea water (pH ~7.8) at room temperature. In all cases, the samples were removed from the solutions, rinsed with DI water, and measured by spectroscopic ellipsometry (J. A. Wooldman Co. Inc., USA) to determine thickness and/or atomic force microscopy (AFM, Asylum Research MFP-3D, USA) to determine both the thickness and surface morphology. After such measurements, each of which lasted a few hours, the samples were returned to the solutions. The solutions were replaced every other day.

Characterization of film properties: Film density was measured using X-ray reflectometry (XRR, X'pert MRD System, Netherlands). X-ray photoelectron spectroscopy was performed with a system from Axis ULTRA, UK. To avoid surface oxidation of the nitrides, the measurements were conducted shortly after oxide removal in buffered oxide etchant (BOE, 6:1, Transene Company Inc., USA) for a few seconds. Transmission electron microscopy (TEM, JEOL 2010F (S)TEM, USA) was used to study the porous microstructure of the PECVD and E-beam oxides.

Encapsulation tests: Serpentine traces of Mg (~300 nm thick) were defined by e-beam evaporation and liftoff using a patterned layer of photoresist (AZ 2070, MicroChem, USA) on a glass substrate. Each trace was then encapsulated with various overcoats of PECVD $SiO_2$, PECVD-LF $Si_3N_4$, and ALD $SiO_2$ (Savannah, Cambridge Nanotech, USA). Encapsulation layers at both ends of the trace were removed by RIE, to allow continuous measurement of changes in resistance while immersed in aqueous solutions.

REFERENCES

[1] J. A. Babcock, S. G. Balster, A. Pinto, C. Dirnecker, P. Steinmann, R. Jumpertz, B. El-Kareh, *IEEE Electron Device Lett.* 2001, 22, 230.
[2] J. Robertson, *Eur. Phys. J. Appl. Phys.* 2004, 28, 265.
[3] A. Hierlemann, Integrated Chemical Microsensor Systems in CMOS Technology, Springer Berlin Heidelberg 2005.
[4] R. Sang, H. Zhang, L. Long, Z. Hua, J. Yu, B. Wei, X. Wu, T. Feng, J. Zhang, in Int. Conf. Electronic Packaging Technology & High Density Packaging, Shanghai, China 2011.
[5] Y.-C. Lin, Q.-K. Le, L.-W. Lai, R.-M. Liao, M.-S. Jeng, D.-S. Liu, *Int. J. Eng. Tech. Innovation* 2012, 2, 184.
[6] D.-H. Kim, Y.-S. Kim, J. Amsden, B. Panilaitis, D. L. Kaplan, F. G. Omenetto, M. R. Zakin, J. A. Rogers, *Appl. Phys. Lett.* 2009, 95, 133701.
[7] D.-H. Kim, J. Viventi, J. Amsden, J. Xiao, L. Vigeland, Y.-S. Kim, J. A. Blanco, B. Panilaitis, E. S. Frechette, D. Contreras, D. L. Kaplan, F. G. Omenetto, Y. Huang, K.-C. Hwang, M. R. Zakin, B. Litt, J. A. Rogers, *Nat. Mater.* 2010, 9, 511.
[8] C. Legnani, C. Vilani, V. L. Calil, H. S. Barud, W. G. Quirino, C. A. Achete, S. J. L. Ribeiro, M. Cremona, *Thin Solid Films* 2008, 517, 1016.
[9] M. Irimia-Vladu, P. A. Troshin, M. Reisinger, L. Shmygleva, Y. Kanbur, G. Schwabegger, M. Bodea, R. Schwodiauer, A. Mumyatov, J. W. Fergus, V. F. Razumov, H. Sitter, N. S. Sariciftci, S. Bauer, *Adv. Funct. Mater.* 2010, 20, 4069.
[10] C. J. Bettinger, Z. Bao, *Adv. Mater.* 2010, 22, 651.
[11] S.-W. Hwang, H. Tao, D.-H. Kim, H. Cheng, J.-K. Song, E. Rill, M. A. Brenckle, B. Panilaitis, S. M. Won, Y.-S. Kim, Y. M. Song, K. J. Yu, A. Ameen, R. Li, Y. Su, M. Yang, D. L. Kaplan, M. R. Zakin, M. J. Slepian, Y. Huang, F. G. Omenetto, J. A. Rogers, *Science,* 2012, 337, 1640.
[12] S.-W. Hwang, D.-H. Kim, H. Tao, T.-I. Kim, S. Kim, K. J. Yu, B. Panilaitis, J.-W. Jeong, J.-K. Song, F. G. Omenetto, J. A. Rogers, *Adv. Funct. Mater.* 2013, 23, 4087.
[13] S.-W. Hwang, X. Huang, J.-H. Seo, J.-K. Song, S. Kim, S. Hage-Ali, H.-J. Chung, H. Tao, F.G. Omenetto, Z. Ma, J. A. Rogers, *Adv. Mater.* 2013, 25, 3526.
[14] C. Dagdeviren, S.-W. Hwang, Y. Su, S. Kim, H. Cheng, 0. Gur, R. Haney, F. G. Omenetto, Y. Huang, J. A. Rogers, *Small* 2013, 9, 3398.
[15] K. G. Knauss, T. J. Wolery, Geochimica et *Cosmochim. Acta* 1988, 52, 43.
[16] W. A. House, L. A. Hickinbotham, *J. Chem. Soc. FARADAY Trans.* 1992, 88, 2021.
[17] W. G. Worley, *Dissolution kinetics and mechanisms in quartz-and grainite-water systems*, Ph. D. thesis, Massachusetts Institute of Technology, 1994.
[18] H. Seidel, L. Csepregi, A. Heuberger, H. Baumgartel, *J. Electrochem. Soc.* 1990, 137, 3612.
[19] L. Yin, H. Cheng, S. Mao, R. Haasch, Y. Liu, X. Xie, S.-W. Hwang, H. Jain, S.-K. Kang, Y. Su, R. Li, Y. Huang, J. A. Rogers, *Adv. Funct. Mater.* DOI:10.1002/adfm.201301847.
[20] J. P. Icenhower, P. M. DOVE, *Geochim. Cosmochim. Acta* 2000, 64, 4193.
[21] P. M. Dove, C. J. Nix, *Geochim. Cosmochim. Acta* 1997, 61, 3329.
[22] P. M. Dove, *Geochim. Cosmochim. Acta* 1999, 63, 3715.
[23] R. C. Jaeger, Introduction to Microelectronic Fabrication, Prentice Hall 2001.
[24] M. F. Ceiler, P. A. Kohl, S. A. Bidstrup, *J. Electrochem. Soc.* 1995, 142, 2067.
[25] D. S. Allam, K. E. G. Pitt, *Thin Solid Films* 1967, 68, 245.
[26] R. Li, H. Cheng, Y. Su, S.-W. Hwang, L. Yin, H. Tao, M. A. Brenckle, D.-H. Kim, F. G. Omenetto, J. A. Rogers, Y. Huang, *Adv. Fund. Mater.* 2013, 23, 3106.
[27] L. Bergstrom, E. Bostedt, *Colloid Surf. A* 1990, 49, 183.
[28] B. V. Zhmud, L. Bergstrom, *J. Colloid Interface Sci.* 1999, 218, 582.
[29] E. Laarz, B. V. Zhmud, L. Bergstrom, *J. Am. Ceram. Soc.* 2000, 83, 2394.
[30] F. J. H. van Assche, R. T. Vangheluwe, J. W. C. Maes, W. S. Mischke, M. D. Bijker, F. C. Dings, M. F. J. Evers, *SID 04 Digest of Technical Papers* 2004, 695.
[31] J. J. W. M. Rosink, H. Lifka, G. H. Rietjens, A. Pierik, *SID 05 Digest of Technical Papers* 2005, 1272.
[32] A. A. Dameron, S. D. Davidson, B. B. Burton, P. F. Carcia, R. S. McLean, S. M. George, *J. Phys. Chem. C* 2008, 112, 4573.

[33] J. Meyer, P. Gorrn, F. Bertram, S. Hamwi, T. Winkler, H.-H. Johannes, T. Weimann, P. Hinze, T. Riedl, W. Kowalsky, *Adv. Mater.* 2009, 21, 1845.

[34] S. Park, W. M. Yun, L. H. Kim, S. Park, S. H. Kim, C. E. Park, *Org. Electron.* 2013 14, 3385.

EXAMPLE 4

Polyanhydrides for Transient Encapsulation

Several polyanhydrides were prepared from various combinations of anhydrides, linkers and thiols, which were combined and irradiated with UV light to initiate a polymerization or curing reaction. The reagent combinations are shown in Table 3. The polyanhydrides were screened to identify candidates for transient encapsulation. Mixtures were tested for UV curability, film integrity, stability toward delamination and stability for 1 day toward dissolution. Passing results are indicated with Os and negative results are indicated with Xs. From these results, mixture 7A was selected as the candidate with the highest potential for a transient organic encapsulant characterized by UV curability, good film integrity, stability toward delamination and stability toward dissolution for at least 1 day.

TABLE 3

Combinations of anhydrides, linkers and thiols to yield polyanhydrides.

| | Anhydride | Linker | Thiol | UV Cure | Film Integrity | Stable for delam. | Stable for 1 day dissol'n test |
|---|---|---|---|---|---|---|---|
| 1A | [structure] | [structure] | [structure] | X | — | — | — |
| 1B | X | [structure] | [structure] | X | — | — | — |
| 2A | [structure] | [structure] | [structure] | O | O | O | ▲ |
| 2B | X | [structure] | [structure] | O | X (Cracks) | O | ▲ |
| 3A | [structure] | [structure] | [structure] | O | O | X | X |
| 3B | X | [structure] | [structure] | X | — | — | — |
| 4A | [structure] | [structure] | [structure] | O | O | O | ▲ |
| 4B | X | [structure] | [structure] | O | O | O | ▲ |
| 5A | [structure] | [structure] | [structure] | X | — | — | — |

TABLE 3-continued

Combinations of anhydrides, linkers and thiols to yield polyanhydrides.

| | Anhydride | Linker | Thiol | UV Cure | Film Integrity | Stable for delam. | Stable for 1 day dissol'n test |
|---|---|---|---|---|---|---|---|
| 5B | X | (triallylamine structure) | HS~~~SH | X | — | — | — |
| 7A | (4-pentanoic anhydride structure) | (triallyl triazine trione structure) | HS~~~SH | O | O | O | O |
| 7B | X | (triallyl triazine trione structure) | HS~~~SH | O | O | O | O |

Figure 4:
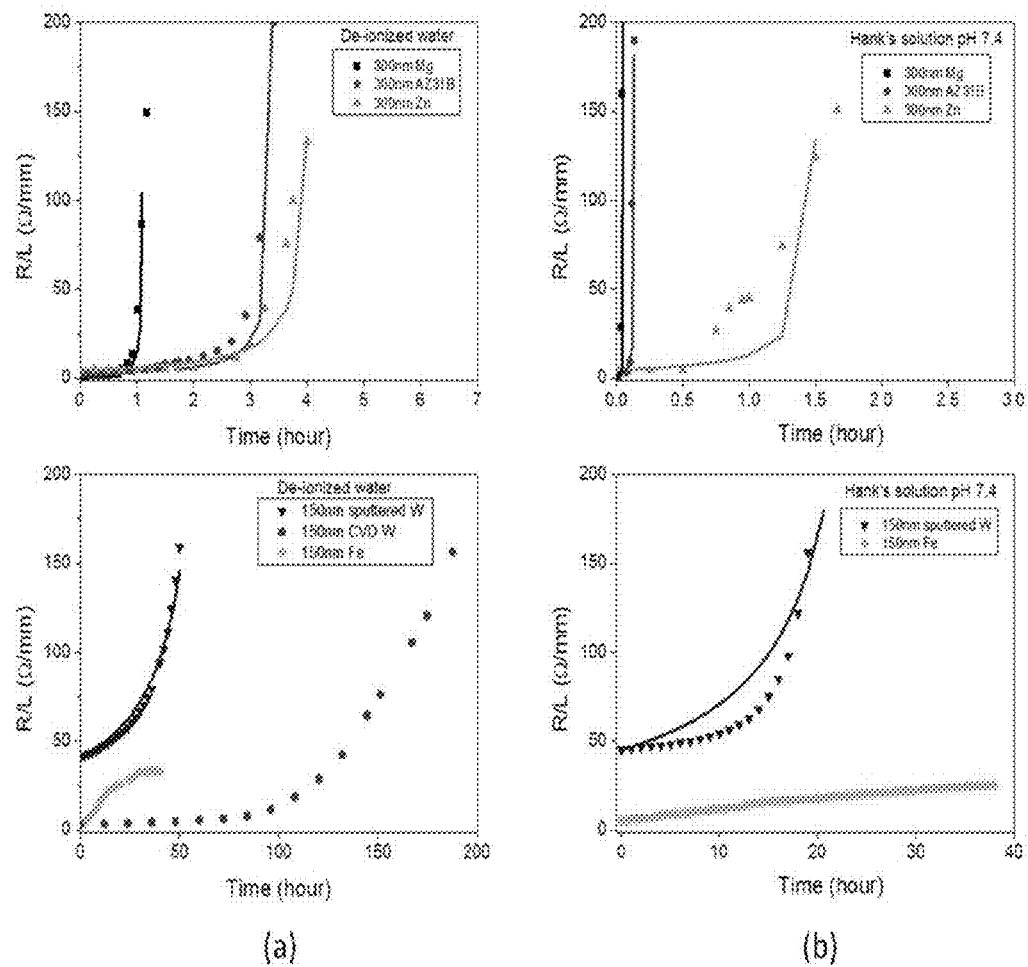
FIG. 4. Change in resistance of test structures of various metals in (a) DI water and (b) pH 7.4 Hank's solution.
Figure 39A:
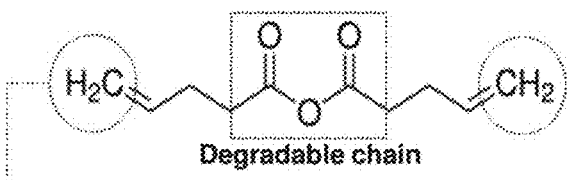
Figure 39A:
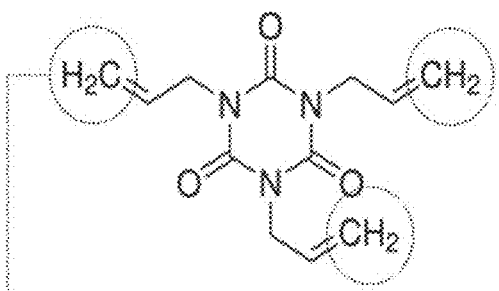
Figure 39A:
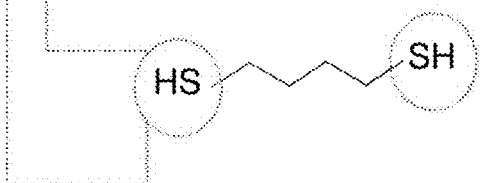

The ratio of anhydride and hydrophobic chain compound (i.e., thiol) in mixture 7A was tuned to optimize transient encapsulation properties. As shown in FIG. 39A, 4-pentanoic anhydride contains a degradable chain and two alkene end groups capable of reacting with 1,4-butane dithiol. 1,3,5-triallyl-1,3,5-triazene-2,4,6(1H, 3H, 5H)-trione contains three alkene groups capable of reacting with 1,4-butane dithiol. FIG. 39B provides the ratios of each component and shows that degradation rate increases as hydrophobicity decreases (hydrophilicity increases). This result is consistent with water permeating a hydrophilic encapsulant more rapidly than a hydrophobic encapsulant.

Figure 39E:
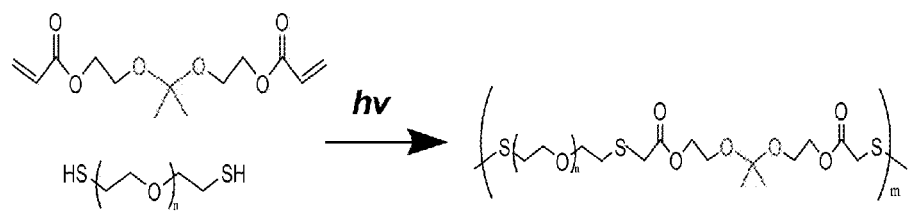

FIGS. 39C-E show additional polyanhydride encapsulant materials formed by photocuring mixtures of one or more anhydride monomers and one or more thiol monomers. FIG. 39C shows a polyanhydride encapsulant material incorporating a phosphodiester group within the polymeric chain. The phosphodiester group increases susceptibility of the polymer to degradation by base and/or enzymes. FIG. 39D shows a polyanhydride encapsulant material incorporating a silyl ether group within the polymeric chain. The silyl ether group increases susceptibility of the polymer material to degradation by acid. FIG. 39E shows a polyanhydride encapsulant material incorporating an ether group within the polymeric chain. The ether group increases susceptibility of the polymer material to degradation by acid. As shown by these examples, suitable polymeric encapsulants may be synthesized and/or selected to achieve a selected programmable transience under a specific environment.

Figure 40:
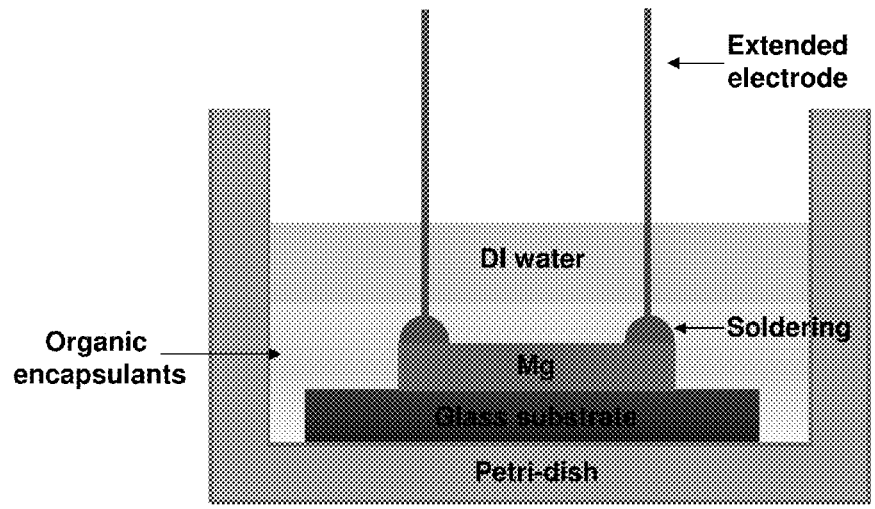
FIG. 40. Schematic of water permeability test set-up.

FIG. 40 shows a schematic of a water permeability test set-up. A magnesium conductor is applied to a glass substrate and two extended electrodes are soldered to ends of the conductor to monitor resistance as a function of time. An organic encapsulant, such as 7A, is applied over the entire device, which is located in a petri dish. DI water is added over the organic encapsulant.

Figure 41:
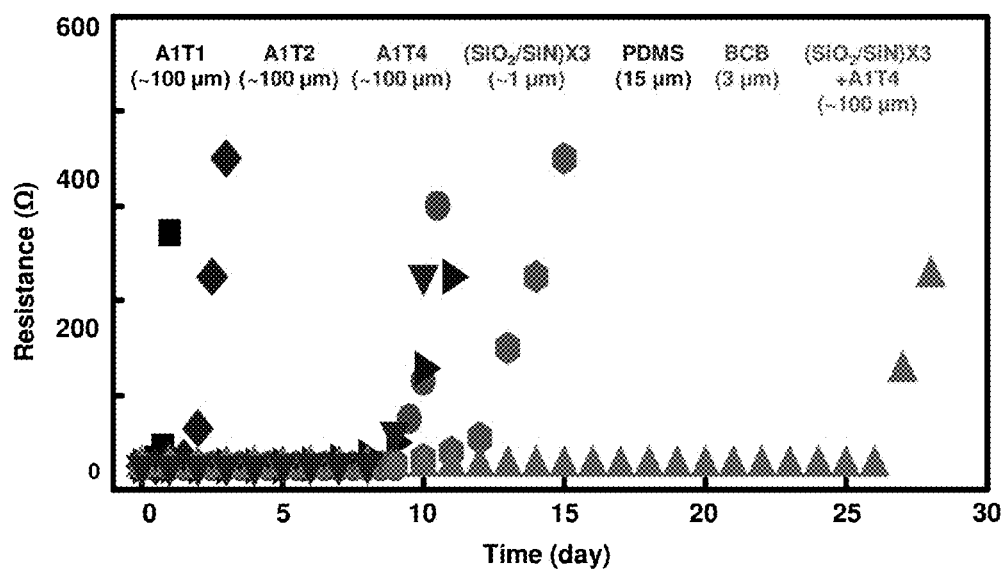
FIG. 41. Performance of the organic encapsulants compared to materials of other classes, such as inorganic encapsulants, as change in conductor resistance over time.

FIG. 41 shows performance of organic encapsulants compared to materials of other classes, such as inorganic encapsulants, as a function of change in conductor resistance over time. A1TX is the polyanhydride synthesized by combining pentanoic anhydride and 1,3,5 triallyl-1,3,5 triazene-2,4,6 (1H, 3H, 5H) trione with a 1:X molar concentration. ($SiO_2$/ SiN)X3 describes a multilayer stack of triple layers of silicon oxide and silicon nitride ($SiO_2$/SiN/$SiO_2$/SiN/$SiO_2$/ SiN). PDMS is poly(dimethyl siloxane). BCB is bisbenzocyclobutene, a non-degradable polymer for comparison with degradable organic and inorganic encapsulants. A1T4 had the lowest water permeation within the polyanhydride class. Combining inorganic and organic encapsulation (($SiO_2$/SiN) X3+A1T4) gave the best results (~27 days). Multiple layers helped to cover defect of previous layers and had better performance against water permeation. In this example, the step of depositing the inorganic layer occurred at 200~350° C., which the organic layer could not withstand without undergoing a chemical and/or physical transformation. Thus, the inorganic layer was applied first, with a top organic layer serving as a mechanical buffer layer because the organic layer is less brittle than the inorganic layer.

In an embodiment, multilayer inorganic-organic encapsulation may include alternating organic and inorganic layers. For example, a first organic layer may cover an electronic device. The organic layer may be conformal and/or may be an electrical insulator. A second encapsulation layer, applied on top of the first organic layer may be an inorganic layer for reducing water permeability. A third encapsulation layer, applied on top of the second encapsulation layer, may be an organic layer, e.g., for filling pinholes or defects in the underlying inorganic layer.

In an embodiment, multilayer inorganic-organic encapsulation may include alternating organic and inorganic devices. For example, an inorganic layer may be applied over an electronic device. The inorganic layer may be conformal and/or may be an electrical insulator. A second encapsulation layer, applied on top of the first inorganic layer, may be an organic layer, e.g., for filling pinholes or defects in the first inorganic layer. A third encapsulation layer, applied on top of the second encapsulation layer, may be an inorganic layer, e.g., for reducing water permeability.

In alternative embodiments, multilayer inorganic-organic encapsulation stacks may include organic layers in direct contact with neighboring organic layers and/or inorganic layers in direct contact with neighboring inorganic layers.

In an embodiment, a multilayer encapsulation stack comprises two, three, four, five, six, seven, eight, nine, ten, twelve, fifteen, twenty or more layers.

Figure 42A:
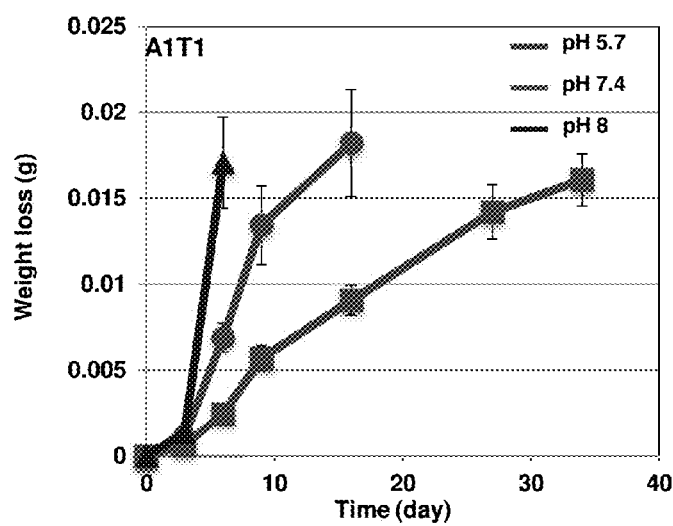
FIG. 42A-C. Dissolution rates of three polyanhydrides (FIG. 42A: A1 T1, FIG. 42B: A1T2, FIG. 42C: A1T4) in buffer solutions with pH 5.7 (squares), pH 7.4 (circles) and pH 8 (triangles).
Figure 42B:
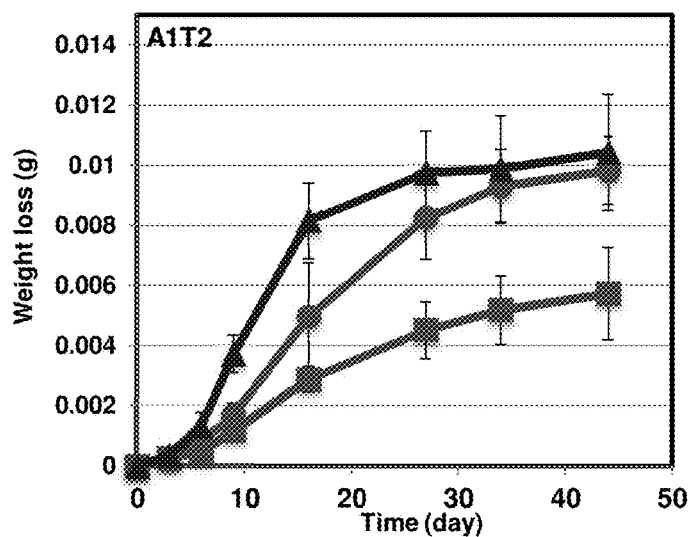
Figure 42C:
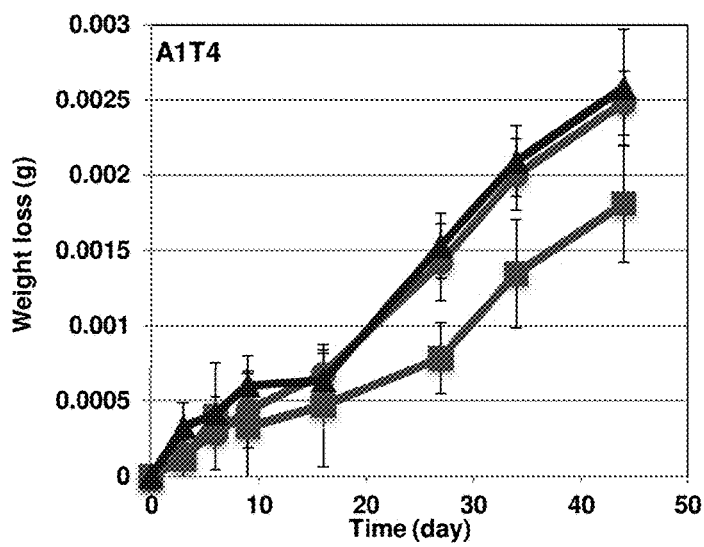

FIGS. 42A-C show the dissolution rates of three polyanhydrides (A1T1, A1T2, A1T4) in buffer solutions with pH 5.7 (squares), pH 7.4 (circles) and pH 8 (triangles). The dissolution rates of the polyanhydrides was highest in acid and lowest in base. A1T4 has low water permeability (FIG. 41) but a slow dissolution rate due to a low concentration of anhydride.

STATEMENTS REGARDING INCORPORATION BY REFERENCE AND VARIATIONS

All references cited throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The following references relate generally to flexible and/or stretchable semiconductor materials and devices. Each is hereby incorporated by reference in its entirety: U.S. patent application Ser. No. 12/778,588, filed on May 12, 2010, PCT International Application No. PCT/US05/19354, filed Jun. 2, 2005 and published under No. WO2005/122285 on Dec. 22, 2005, U.S. Provisional Patent Application No. 61/313, 397, filed Mar. 12, 2010, U.S. patent application Ser. No. 11/851,182, filed Sep. 6, 2007 and published under No. 2008/0157235 on Jul. 3, 2008, and PCT International Application No. PCT/US07/77759, filed Sep. 6, 2007 and published under No. WO2008/030960 on Mar. 13, 2008.

The following references relate generally to bioresorbable substrates and methods of making bioresorbable substrates. Each is hereby incorporated by reference in its entirety: PCT Patent Application PCT/US03/19968 filed Jun. 24, 2003, PCT Patent Application PCT/US04/000255 filed Jan. 7, 2004, PCT Patent Application PCT/US04/11199 filed Apr. 12, 2004, PCT Patent Application PCT/US05/20844 filed Jun. 13, 2005, and PCT Patent Application PCT/US06/029826 filed Jul. 28, 2006.

The following references relate generally to transient electronic devices. Each is hereby incorporated by reference in its entirety: U.S. patent application Ser. No. 13/624,096 and PCT International Application No. PCT/US2012/056538, each filed Sep. 21, 2012.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, and method steps set forth in the present description. As will be obvious to one of skill in the art, methods and devices useful for the present methods can include a large number of optional composition and processing elements and steps.

When a group of substituents is disclosed herein, it is understood that all individual members of that group and all subgroups, including any isomers, enantiomers, and diastereomers of the group members, are disclosed separately. When a Markush group or other grouping is used herein, all individual members of the group and all combinations and subcombinations possible of the group are intended to be individually included in the disclosure. When a compound is described herein such that a particular isomer, enantiomer or diastereomer of the compound is not specified, for example, in a formula or in a chemical name, that description is intended to include each isomers and enantiomer of the compound described individually or in any combination. Additionally, unless otherwise specified, all isotopic variants of compounds disclosed herein are intended to be encompassed by the disclosure. For example, it will be understood that any one or more hydrogens in a molecule disclosed can be replaced with deuterium or tritium. Isotopic variants of a molecule are generally useful as standards in assays for the molecule and in chemical and biological research related to the molecule or its use. Methods for making such isotopic variants are known in the art. Specific names of compounds are intended to be exemplary, as it is known that one of ordinary skill in the art can name the same compounds differently.

The following references relate generally to fabrication methods, structures and systems for making electronic devices, and are hereby incorporated by reference to the extent not inconsistent with the disclosure in this application.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

| Attorney Docket No. | Application No. | Filing Date | Publication No. | Publication Date | Pat. No. | Issue Date |
|---|---|---|---|---|---|---|
| 145-03 US | 11/001,689 | Dec. 1, 2004 | 2006/0286488 | Dec. 21, 2006 | 7,704,684 | Apr. 27, 2010 |
| 18-04 US | 11/115,954 | Apr. 27, 2005 | 2005/0238967 | Oct. 27, 2005 | 7,195,733 | Mar. 27, 2007 |
| 38-04A US | 11/145,574 | Jun. 2, 2005 | 2009/0294803 | Dec. 3, 2009 | 7,622,367 | Nov. 24, 2009 |
| 38-04B US | 11/145,542 | Jun. 2, 2005 | 2006/0038182 | Feb. 23, 2006 | 7,557,367 | Jul. 7, 2009 |
| 43-06 US | 11/421,654 | Jun. 1, 2006 | 2007/0032089 | Feb. 8, 2007 | 7,799,699 | Sep. 21, 2010 |
| 38-04C US | 11/423,287 | Jun. 9, 2006 | 2006/0286785 | Dec. 21, 2006 | 7,521,292 | Apr. 21, 2009 |

-continued

| Attorney Docket No. | Application No. | Filing Date | Publication No. | Publication Date | Pat. No. | Issue Date |
|---|---|---|---|---|---|---|
| 41-06 US | 11/423,192 | Jun. 9, 2006 | 2009/0199960 | Aug. 13, 2009 | 7,943,491 | May 17, 2011 |
| 25-06 US | 11/465,317 | Aug. 17, 2006 | — | — | — | — |
| 137-05 US | 11/675,659 | Feb. 16, 2007 | 2008/0055581 | Mar. 6, 2008 | — | — |
| 90-06 US | 11/782,799 | Jul. 25, 2007 | 2008/0212102 | Sep. 4, 2008 | 7,705,280 | Apr. 27, 2010 |
| 134-06 US | 11/851,182 | Sep. 6, 2007 | 2008/0157235 | Jul. 3, 2008 | 8,217,381 | Jul. 10, 2012 |
| 151-06 US | 11/585,788 | Sep. 20, 2007 | 2008/0108171 | May 8, 2008 | 7,932,123 | Apr. 26, 2011 |
| 216-06 US | 11/981,380 | Oct. 31, 2007 | 2010/0283069 | Nov. 11, 2010 | 7,972,875 | Jul. 5, 2011 |
| 116-07 US | 12/372,605 | Feb. 17, 2009 | — | — | — | — |
| 213-07 US | 12/398,811 | Mar. 5, 2009 | 2010/0002402 | Jan. 7, 2010 | 8,552,299 | Oct. 8, 2013 |
| 38-04D US | 12/405,475 | Mar. 17, 2009 | 2010/0059863 | Mar. 11, 2010 | 8,198,621 | Jun. 12, 2012 |
| 170-07 US | 12/418,071 | Apr. 3, 2009 | 2010/0052112 | Mar. 4, 2010 | 8,470,701 | Jun. 25, 2013 |
| 38-04A1 US | 12/564,566 | Sep. 22, 2009 | 2010/0072577 | Mar. 25, 2010 | 7,982,296 | Jul. 19, 2011 |
| 71-07 US | 12/669,287 | Jan. 15, 2010 | 2011/0187798 | Aug. 4, 2011 | — | — |
| 60-09 US | 12/778,588 | May 12, 2010 | 2010/0317132 | Dec. 16, 2010 | — | — |
| 43-06A US | 12/844,492 | Jul. 27, 2010 | 2010/0289124 | Nov. 18, 2010 | 8,039,847 | Oct. 18, 2011 |
| 15-10 US | 12/892,001 | Sep. 28, 2010 | 2011/0230747 | Sep. 22, 2011 | 8,666,471 | Mar. 4, 2014 |
| 15-10A US | 14/140,299 | Dec. 24, 2013 | — | — | — | — |
| 19-10 US | 12/916,934 | Nov. 1, 2010 | 2012/0105528 | May 3, 2012 | 8,562,095 | Oct. 22, 2013 |
| 3-10 US | 12/947,120 | Nov. 16, 2010 | 2011/0170225 | Jul. 14, 2011 | — | — |
| 118-08 US | 12/996,924 | Dec. 8, 2010 | 2011/0147715 | Jun. 23, 2011 | — | — |
| 126-09 US | 12/968,637 | Dec. 15, 2010 | 2012/0157804 | Jun. 21, 2012 | — | — |
| 50-10 US | 13/046,191 | Mar. 11, 2011 | 2012/0165759 | Jun. 28, 2012 | — | — |
| 151-06A US | 13/071,027 | Mar. 24, 2011 | 2011/0171813 | Jul. 14, 2011 | — | — |
| 137-05A US | 13/095,502 | Apr. 27, 2011 | — | — | — | — |
| 216-06B US | 13/100,774 | May 4, 2011 | 2011/0266561 | Nov. 3, 2011 | — | — |
| 38-04A2 US | 13/113,504 | May 23, 2011 | 2011/0220890 | Sep. 15, 2011 | 8,440,546 | May 14, 2013 |
| 136-08 US | 13/120,486 | Aug. 4, 2011 | 2011/0277621 | Nov. 17, 2011 | — | — |
| 151-06B US | 13/228,041 | Sep. 8, 2011 | 2011/0316120 | Dec. 29, 2011 | — | — |
| 43-06B US | 13/270,954 | Oct. 11, 2011 | 2012/0083099 | Apr. 5, 2012 | 8,394,706 | Mar. 12, 2013 |
| 3-11 US | 13/349,336 | Jan. 12, 2012 | 2012/0261551 | Oct. 18, 2012 | — | — |
| 38-04E US | 13/441,618 | Apr. 6, 2012 | 2013/0100670 | Apr. 25, 2013 | — | — |
| 134-06B US | 13/441,598 | Apr. 6, 2012 | 2012/0327608 | Dec. 27, 2012 | — | — |
| 28-11 US | 13/472,165 | May 15, 2012 | 2012/0320581 | Dec. 20, 2012 | — | — |
| 7-11 US | 13/486,726 | Jun. 1, 2012 | 2013/0072775 | Mar. 21, 2013 | — | — |
| 29-11 US | 13/492,636 | Jun. 8, 2012 | 2013/0041235 | Feb. 14, 2013 | — | — |
| 84-11 US | 13/549,291 | Jul. 13, 2012 | 2013/0036928 | Feb. 14, 2013 | — | — |
| 25-06A US | 13/596,343 | Aug. 28, 2012 | 2012/0321785 | Dec. 20, 2012 | 8,367,035 | Feb. 5, 2013 |
| 150-11 US | 13/624,096 | Sep. 21, 2012 | 2013/0140649 | Jun. 6, 2013 | — | — |
| 38-04A3 US | 13/801,868 | Mar. 13, 2013 | 2013/0320503 | Dec. 5, 2013 | 8,664,699 | Mar. 4, 2014 |
| 38-04A4 US | 14/155,010 | Jan. 14, 2014 | — | — | — | — |
| 125-12 US | 13/835,284 | Mar. 15, 2013 | — | — | — | — |
| 30-13 US | 13/853,770 | Mar. 29, 2013 | — | — | — | — |

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Whenever a range is given in the specification, for example, a range of integers, a temperature range, a time range, a composition range, or concentration range, all intermediate ranges and subranges, as well as all individual values included in the ranges given are intended to be included in the disclosure. As used herein, ranges specifically include the values provided as endpoint values of the range. As used herein, ranges specifically include all the integer values of the range. For example, a range of 1 to 100 specifically includes the end point values of 1 and 100. It will be understood that any subranges or individual values in a range or subrange that are included in the description herein can be excluded from the claims herein.

As used herein, "comprising" is synonymous and can be used interchangeably with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" can be replaced with either of the other two terms. The invention illustratively described herein suitably can be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the invention has been specifically disclosed by preferred embodiments and optional features, modification and variation of the concepts herein disclosed can be resorted to by those skilled in the art, and that such modifications and variations are considered to be within the scope of this invention as defined by the appended claims.

We claim:

1. A method of using a transient electronic device, said method comprising the steps of:
providing the transient electronic device comprising:
a substrate;
one or more active or passive electronic device components supported by said substrate; wherein said active or passive electronic device components independently comprise a selectively transformable material; and
an encapsulant layer at least partially encapsulating said one or more active or passive electronic device components;
wherein said substrate, said encapsulant layer or both independently comprise a selectively removable inorganic material responsive to an external or internal stimulus; wherein at least partial removal of said substrate, said encapsulant layer or both in response to said external or internal stimulus initiates at least partial transformation of said one or more active or passive electronic device components providing a programmable transformation of the transient electronic device in response to said external or internal stimulus at a pre-selected time or at a pre-selected rate, wherein said programmable transformation provides a change in function of the transient electronic device from a first condition to a second condition; and
exposing said transient electronic device to said external or internal stimulus resulting in said at least partial removal of said substrate or encapsulant layer to expose said one or more active or passive electronic device components to said external or internal stimulus, thereby providing said programmable transformation of the transient electronic device;
wherein said removal of said substrate, said encapsulant layer or both in response to said internal or external stimulus occurs via a phase change, dissolution, hydrolysis, bioresorption, etching, corrosion, a photochemical reaction, an electrochemical reaction or any combination of these processes.

2. The method of claim 1, wherein said one or more active or passive electronic device components comprise one or more inorganic semiconductor components, one or more metallic conductor components or one or more inorganic semiconductor components and one or more metallic conductor components.

3. The method of claim 1, wherein said step of exposing said transient electronic device to said external or internal stimulus results in the entire removal of said substrate, said encapsulant layer or both.

4. The method of claim 1, wherein said step of exposing said transient electronic device to said external or internal stimulus results in less than the entire removal of said substrate, said encapsulant layer or both.

5. The method of claim 1, wherein said step of exposing said transient electronic device to said external or internal stimulus exposes at least 1% of an outer surface of said one or more active or passive electronic device components.

6. The method of claim 1, wherein said step of exposing said transient electronic device to said external or internal stimulus exposes 1% to 100% of an outer surface of said one or more active or passive electronic device components.

7. The method of claim 1, wherein said substrate, said encapsulant layer or both independently comprise an entirely inorganic structure or a composite inorganic and organic structure.

8. The method of claim 7, wherein said entirely inorganic structure comprises one or more of $SiO_2$, spin-on-glass, Mg, Mg alloys, Fe, W, Zn, Mo, Si, SiGe, $Si_3N_4$ and MgO.

9. The method of claim 7, wherein said composite inorganic and organic structure comprises an inorganic layer having a first surface adjacent said active or passive electronic device components and a second surface adjacent to an organic layer or an organic layer having a first surface adjacent said active or passive electronic device components and a second surface adjacent said inorganic layer.

10. The method of claim 9, wherein said inorganic layer comprises one or more of $SiO_2$, spin-on-glass, Mg, Mg alloys, Fe, W, Zn, Mo, Si, SiGe, $Si_3N_4$ and MgO and said organic layer comprises one or more of a polyanhydride and poly(dimethyl siloxane) (PDMS).

11. The method of claim 1, wherein said device is an entirely inorganic device, wherein said active or passive electronic device components, said substrate and said encapsulant layer each are independently entirely composed of one or more inorganic materials.

12. The method of claim 1, wherein said substrate, said encapsulant layer or both independently have a preselected transience profile in response to said external or internal stimulus, wherein said preselected transience profile is characterized by a removal of 0.01% to 100% of said substrate or said encapsulant layer over a time interval selected from the range of 1 ms to 5 years or a decrease in average thickness of said substrate or said encapsulant layer at a rate selected over the range of 0.01 nm/day to 100 microns $s^{-1}$.

13. The method of claim 1, wherein said selectively removable inorganic material of said substrate, said encapsulant layer or both independently comprises a metal, a metal oxide, a ceramic or a combination of these, a crystalline material, an amorphous material or a combination thereof, a single crystalline material, polycrystalline material or doped crystalline material, a glass, a thin film, a coating, a foil or any combination of these, or a nanostructured layer or a microstructured layer.

14. The method of claim 1, wherein said selectively removable inorganic material of said substrate, said encapsulant layer or both independently comprises Mg, W, Mo, Fe, Zn, or an alloy thereof, $SiO_2$, MgO, $N_4Si_3$, SiC, a spin-on-glass, a solution processable glass, a biocompatible material, a bioinert material or a combination of biocompatible and bioinert materials.

15. The method of claim 1, wherein said substrate, said encapsulant layer or both independently comprise a multilayer structure comprising one or more thin films, coatings, or foils comprising said selectively removable inorganic material.

16. The method of claim 1, wherein said substrate, said encapsulant layer or both independently comprises a composite inorganic and organic structure having a multilayer geometry.

17. The method of claim 15, wherein said multilayer structure further comprises one or more electrically insulating layers, barrier layers or any combinations thereof; wherein said one or more electrically insulating layers or barrier layers is provided in physical contact, electrical contact or both with said one or more thin films, coatings, or foils; wherein said one or more electrically insulating layers or barrier layers comprises an exterior layer of said multilayer structure or wherein said one or more electrically insulating layers or barrier layers comprises an interior layer of said multilayer structure in physical contact or electrical contact with said one or more active or passive electronic device components; or wherein said one or more electrically insulating layers or barrier layers comprises a polymer, an insulating ceramic, a glass, $SiO_2$, spin-on glass, MgO or any combination of these.

18. The method of claim 17, wherein said multilayer structure comprises a metal foil or thin metal film having a first side in physical contact with a first electronically insulating layer or barrier layer; wherein said first electronically insulating layer or barrier layer is an exterior layer of said multilayer structure or wherein said first electronically insulating layer or barrier layer is an interior layer of said multilayer structure in physical contact or electrical contact with said active or passive electronic device components; wherein said first electronically insulating layer or barrier layer comprises a polymer layer or coating, a metal oxide layer or coating, a glass layer or coating or any combination of these; wherein said multilayer structure comprises said metal foil or thin metal film having a second side coated in contact with a second electronically insulating layer or barrier layer; or wherein said metal foil or thin metal film is provided between said first electronically insulating layer or barrier layer and said second electronically insulating layer or barrier layer.

19. The method of claim 1, wherein said substrate, said encapsulant layer or both independently have a porosity selected from the range of 0.01% to 99.9%, an extent of crystallinity selected from the range of 0.01% to 100%, or a density selected from the range of 0.01% to 100% compared to bulk prior to said at least partial removal of said substrate, said encapsulant layer or both in response to said external or internal stimulus.

20. The method of claim 1, wherein a time for a thickness of said selectively removable inorganic material to reach zero is provided by the expression:

$$t_c = \frac{4\rho_m M(H_2O)}{kw_0 M(m)} \frac{\sqrt{\frac{kh_0^2}{D}}}{\tanh\sqrt{\frac{kh_0^2}{D}}};$$

where $t_c$ is the critical time, $\rho_m$ is the mass density of the material, $M(H_2O)$ is the molar mass of water, $M(m)$ is the molar mass of the material, $h_0$ is the initial thickness of the material, D is the diffusivity of water, k is the reaction constant for the dissolution reaction, and $w_0$ is the initial concentration of water; wherein k has a value selected from the range of $1\times10^5$ $s^{-1}$ to $1\times10^{-10}$ $s^{-1}$.

21. The method of claim 1, wherein said substrate, said encapsulant layer or both are substantially impermeable to water, limit a net leakage current to the surroundings to 0.1 $\mu A/cm^2$ or less, or undergo an increase in volume equal to or less than 10% upon exposure to an aqueous or nonaqueous solvent prior to said at least partial removal of said substrate, said encapsulant layer or both in response to said external or internal stimulus.

22. The method of claim 15, wherein said thin film, coating, or foil has an average thickness over or underneath of said one or more active or passive electronic device components less than or equal to 1000 μm prior to said at least partial removal of said substrate, said encapsulant layer or both in response to said external or internal stimulus.

23. The method of claim 1, wherein said substrate, said encapsulant layer or both independently have a thickness selected from the range of 0.1 μm to 1000 μm, an average modulus selected over the range of 0.5 KPa to 10 TPa, a net flexural rigidity less than or equal to $1\times10^{-4}$ Nm, or a net bending stiffness less than or equal to $1\times10^8$ GPa μm$^4$ prior to said at least partial removal of said substrate, said encapsulant layer or both in response to said external or internal stimulus.

24. The method of claim 1, wherein said substrate, said encapsulant layer or both are at least partially optically transparent in the visible or infrared regions of the electromagnetic spectrum.

25. The method of claim 1, wherein said substrate, said encapsulant layer or both are generated via physical vapor deposition, chemical vapor deposition, sputtering, atomic layer deposition, electrochemical deposition, spin casting, electrohydrodynamic jet printing, screen printing or any combination of these.

26. The method of claim 1, wherein said substrate, said encapsulant layer or both cover or support a percentage of an exterior area or an interior area of said one or more active or passive electronic device components selected from the range of 1% to 100% or wherein said substrate, said encapsulant layer or both cover or support 10% or more of an exterior area or an interior area of said one or more active or passive electronic device components.

27. The method of claim 1, wherein said one or more inorganic semiconductor components comprise a polycrystalline semiconductor material, single crystalline semiconductor material or a doped polycrystalline or single crystalline semiconductor material, Si, Ga, GaAs, ZnO or any combination of these.

28. The method of claim 2, wherein said one or more metallic conductor components comprise Mg, W, Mo, Fe, Zn or an alloy thereof.

29. The method of claim 2, wherein said one or more inorganic semiconductor components, one or more metallic conductor components or both comprise a component of an electronic device selected from the group consisting of a transistor, a diode, an amplifier, a multiplexer, a light emitting diode, a laser, a photodiode, an integrated circuit, a sensor, a temperature sensor, an electrochemical cell, a thermistor, a heater, a resistive heater, an antenna, a battery, an energy storage system, an actuator, a nanoelectromechanical system or a microelectromechanical system, and an actuator and arrays thereof.

30. The method of claim 1, wherein said device is a communication system, a photonic device, a sensor, an optoelectronic device, a biomedical device, a temperature sensor, a photodetector, a photovoltaic device, a strain gauge, an imaging system, a wireless transmitter, an electrochemical cell, an antenna, a battery, an energy storage system, an actuator, a nanoelectromechanical system or a microelectromechanical system.

* * * * *